US011725306B2

(12) United States Patent
Chaudhary et al.

(10) Patent No.: US 11,725,306 B2
(45) Date of Patent: Aug. 15, 2023

(54) ANTIBODY FRAGMENT LIBRARY, AND USES THEREOF

(71) Applicant: UNIVERSITY OF DELHI SOUTH CAMPUS, New Delhi (IN)

(72) Inventors: Vijay Kumar Chaudhary, New Delhi (IN); Amita Gupta, New Delhi (IN); Vaishali Verma, New Delhi (IN)

(73) Assignee: UNIVERSITY OF DELHI SOUTH CAMPUS, New Delhi (IN)

( * ) Notice: Subject to any disclaimer, the term of this patent is extended or adjusted under 35 U.S.C. 154(b) by 392 days.

(21) Appl. No.: 16/768,116

(22) PCT Filed: Nov. 30, 2018

(86) PCT No.: PCT/IN2018/050802
§ 371 (c)(1),
(2) Date: May 29, 2020

(87) PCT Pub. No.: WO2019/106694
PCT Pub. Date: Jun. 6, 2019

(65) Prior Publication Data
US 2020/0318100 A1 Oct. 8, 2020

(30) Foreign Application Priority Data
Nov. 30, 2017 (IN) .............. 201711043081

(51) Int. Cl.
C40B 50/06 (2006.01)
C07K 16/00 (2006.01)
C12N 15/10 (2006.01)

(52) U.S. Cl.
CPC ............ *C40B 50/06* (2013.01); *C07K 16/005* (2013.01); *C12N 15/1037* (2013.01); *C07K 2317/21* (2013.01); *C07K 2317/622* (2013.01)

(58) Field of Classification Search
None
See application file for complete search history.

(56) References Cited

U.S. PATENT DOCUMENTS 5,969,108 A 10/1999 McCafferty et al.
6,794,128 B2 9/2004 Marks et al.
(Continued)

FOREIGN PATENT DOCUMENTS

| EP | 9908856 B2 | 3/2018 |
| WO | 2017109721 A1 | 6/2017 |
| WO | 2018002952 A2 | 1/2018 |

OTHER PUBLICATIONS

De Bruin et al., 1999, "Selection of high-affinity phage antibodies from phage display libraries." Nat Biotechnol 17(4): 397-9.
(Continued)

*Primary Examiner* — Christian C Boesen
(74) *Attorney, Agent, or Firm* — Thomas | Horstemeyer, LLP

(57) ABSTRACT

The present disclosure discloses an antibody fragment library, method for preparing the library and its applications. The essential steps in construction of the library is devoid of any restriction enzyme. Emulsion based PCR has been used as an important tool for the construction and validation of the library. The method as disclosed in the present disclosure leads to construction of a library comprising at least 8 billion clones.

7 Claims, 16 Drawing Sheets
Specification includes a Sequence Listing.

(56) References Cited

U.S. PATENT DOCUMENTS

| | | |
|---|---|---|
| 2002/0102613 A1 | 8/2002 | Hoogenboom |
| 2009/0054254 A1 | 2/2009 | Throsby et al. |

OTHER PUBLICATIONS

Ewert, S., T. Huber, A. Honegger and A. Pluckthun (2003). "Biophysical properties of human antibody variable domains." J Mol Biol 325(3): 531-53).

Glanville et al. (Glanville, J., W. Zhai, J. Berka, D. Telman, G. Huerta, G. R. Mehta, I. Ni, L. Mei, P. D. Sundar, G. M. Day, D. Cox, A. Rajpal and J. Pons (2009).

Kim et al., 2017 (Kim, S., I. Park, S. G. Park, S. Cho, J. H. Kim, N. S. Ipper, S. S. Choi, E. S. Lee and H. J. Hong (2017).

Pasello et al., 2016 (Pasello, M., S. Zamboni, A. Mallano, M. Flego, P. Picci, M. Cianfriglia and K. Scotlandi (2016).

Kugler et al., 2015 (Kugler, J., S. Wilke, D. Meier, F. Tomszak, A. Frenzel, T. Schirrmann, S. Dubel, H. Garritsen, B. Hock, L. Toleikis, M. Schutte and M. Hust (2015).

Schwimmer et al., 2013 (Schwimmer, L. J., B. Huang, H. Giang, R. L. Cotter, D. S. Chemla-Vogel, F. V. Dy, E. M. Tam, F. Zhang, P. Toy, D. J. Bohmann, S. R. Watson, J. W. Beaber, N. Reddy, H. F. Kuan, D. H. Bedinger and I. J. Rondon (2013).

Hust et al., 2011 (Hust, M., T. Meyer, B. Voedisch, T. Rulker, H. Thie, A. El-Ghezal, M. I. Kirsch, M. Schutte, S. Helmsing, D. Meier, T. Schirrmann and S. Dubel (2011). ""A human scFv antibody generation pipeline for proteome research."" J Biotechnol 152(4): 159-70).

Glanville et al., 2009 (Glanville, J., W. Zhai, J. Berka, D. Telman, G. Huerta, G. R. Mehta, I. Ni, L. Mei, P. D. Sundar, G. M. Day, D. Cox, A. Rajpal and J. Pons (2009).

Lloyd et al., 2009 (Lloyd, C., D. Lowe, B. Edwards, F. Welsh, T. Dilks, C. Hardman and T. Vaughan (2009).

Pansri et al., 2009 (Pansri, P., N. Jaruseranee, K. Rangnoi, P. Kristensen and M. Yamabhai (2009).

Michael Hust et al.:Human Antibody GeneLibraries. In: AntibodyEngineering, R. Kontermannand S. Dubel, Springer Verlag,Heidelberg, Germany (2010)pp. 65-84.

Schofield et al., 2007 (Schofield, D. J., A. R. Pope, V. Clementel, J. Buckell, S. Chapple, K. F. Clarke, J. S. Conquer, A. M. Crofts, S. R. Crowther, M. R. Dyson, G. Flack, G. J. Griffin, Y. Hooks, W. J. Howat, A. Kolb-Kokocinski, S. Kunze, C. D. Martin, G. L. Maslen, J. N. Mitchell, M. O'Sullivan, R. L. Perera, W. Roake, S. P. Shadbolt, K. J. Vincent, A. Warford, W. E. Wilson, J. Xie, J. L. Young and J. McCafferty (2007).

Tay, M.Y.F. et al.: Identification of DengueSpecific Human AntibodyFragments Using PhageDisplay, 2014, In: Padmanabhan R., VasudevanS. (eds) Dengue. Methods inMolecular Biology (Methodsand Protocols), vol. 1138. Humana Press, New York,NY.,pp. 161-173.

Loset et al., 2005 (Loset, G. A., I. Lobersli, A. Kavlie, J. E. Stacy, T. Borgen, L. Kausmally, E. Hvattum, B. Simonsen, M. B. Hovda and O. H. Brekke (2005).Construction, evaluation and refinement of a large human antibody phage library based on the IgD and IgM variable gene repertoire. J Immunol Methods 299(1-2): 47-62).

Patrick Chames et al.:Selection of antibodies againstbiotinylated antigens. From:Methods in Molecular Biology,vol. 178: Antibody PhageDisplay: Methods andProtocols, Edited by: P. M O'Brien and R. Aitken (2002),pp. 147-157.

Rojas et al., 2002 (Rojas, G., J. C. Almagro, B. Acevedo and J. V. Gavilondo (2002). Phage antibody fragments library combining a single human light chain variable region with immune mouse heavy chain variable regions.J Biotechnol 94(3): 287-98).

Vijay K Chaudhary et al.:Rapid Restriction Enzyme-FreeCloning of PCR Products: AHigh-Throughput MethodApplicable for LibraryConstruction., Oct. 31, 2014, PLoS ONE 9(10):e111538.

De Haard et al., 1999 (de Haard, H. J., N. van Neer, A. Reurs, S. E. Hufton, R. C. Roovers, P. Henderikx, A. P. de Bruine, J. W. Arends and H. R. Hoogenboom (1999).

Pierre Martineau: Synthetic antibody libraries. In: Antibody Engineering, R. Kontermann and S. Dubel, Springer Verlag, Heidelberg, Germany (2010) pp. 85-97.

Sheets et al., 1998 (Sheets, M. D., P. Amersdorfer, R. Finnem, P. Sargent, E. Lindquist, R. Schier, G. Hemingsen, C. Wong, J. C. Gerhart and J. D. Marks (1998).

Anke Krebber et al.: Reliable cloning of functional antibody variable domains from hybridomas and spleen cell repertoires employing a reengineered phage display system, 1997, Journal of Immunological Methods, 201, 35-55.

Marks et al., 1991 (Marks, J. D., H. R. Hoogenboom, T. P. Bonnert, J. McCafferty, A. D. Griffiths and G. Winter (1991).

Ming-Yan Xu et al.:Production of a human singlechain variable fragmentantibody against esophagealcarcinoma, Sep. 15, 2004, World Journal of Gastroenterology, 10(18):2619-2623.

LeFranc et al. (1999), IMGT, the international ImMunoGeneTics database, Nucleic Acids Research, 1999, vol. 27 No. 1.

SEQUENCE LISTING

<160> NUMBER OF SEQ ID NOS: 110

<210> SEQ ID NO 1
<211> LENGTH: 26
<212> TYPE: DNA
<213> ORGANISM: Artificial Sequence
<220> FEATURE:
<223> OTHER INFORMATION: Primer Sequence - HuVK11-51 (K1)

<400> SEQUENCE: 1
gctgacatcc agatgaccca gtctcc                                    26

<210> SEQ ID NO 2
<211> LENGTH: 26
<212> TYPE: DNA
<213> ORGANISM: Artificial Sequence
<220> FEATURE:
<223> OTHER INFORMATION: Primer sequence - HuVK12-51 (K2)

```
<400> SEQUENCE: 2
gctgmcatcc rgwtgaccca gtctcc                                          26

<210> SEQ ID NO 3
<211> LENGTH: 26
<212> TYPE: DNA
<213> ORGANISM: Artificial Sequence
<220> FEATURE:
<223> OTHER INFORMATION: Primer sequence - HuVK2-51 (K3)

<400> SEQUENCE: 3
gctgatrttg tgatgacyca gwctcc                                          26

<210> SEQ ID NO 4
<211> LENGTH: 26
<212> TYPE: DNA
<213> ORGANISM: Artificial Sequence
<220> FEATURE:
<223> OTHER INFORMATION: Primer sequence - HuVK3-51 (K4)

<400> SEQUENCE: 4
gctgaaatwg tgwtgacrca gtctcc                                          26

<210> SEQ ID NO 5
<211> LENGTH: 26
<212> TYPE: DNA
<213> ORGANISM: Artificial Sequence
<220> FEATURE:
<223> OTHER INFORMATION: Primer sequence - HuVK4-51 (K5)

<400> SEQUENCE: 5
gctgacatcg tgatgaccca gtctcc                                          26

<210> SEQ ID NO 6
<211> LENGTH: 26
<212> TYPE: DNA
<213> ORGANISM: Artificial Sequence
<220> FEATURE:
<223> OTHER INFORMATION: Primer sequence - HuVK5-51 (K6)

<400> SEQUENCE: 6
gctgaaacga cactcacgca gtctcc                                          26

<210> SEQ ID NO 7
<211> LENGTH: 26
<212> TYPE: DNA
<213> ORGANISM: Artificial Sequence
<220> FEATURE:
<223> OTHER INFORMATION: Primer sequence - HuVK6-51 (K7)

<400> SEQUENCE: 7
gctgawrttg tgmtgacwca gtctcc                                          26

<210> SEQ ID NO 8
<211> LENGTH: 46
<212> TYPE: DNA
<213> ORGANISM: Artificial Sequence
<220> FEATURE:
<223> OTHER INFORMATION: Primer sequence - HuVK11-52 (K8)

<400> SEQUENCE: 8
tggcagctca gccagcgatg gctgacatcc agatgaccca gtctcc                    46

<210> SEQ ID NO 9
<211> LENGTH: 46
```

```
<212> TYPE: DNA
<213> ORGANISM: Artificial Sequence
<220> FEATURE:
<223> OTHER INFORMATION: Primer sequence - HuVK12-52 (K9)

<400> SEQUENCE: 9
tggcagctca gccagcgatg gctgmcatcc rgwtgaccca gtctcc          46

<210> SEQ ID NO 10
<211> LENGTH: 46
<212> TYPE: DNA
<213> ORGANISM: Artificial Sequence
<220> FEATURE:
<223> OTHER INFORMATION: Primer sequence - HuVK2-52 (K10)

<400> SEQUENCE: 10
tggcagctca gccagcgatg gctgatrttg tgatgacyca gwctcc          46

<210> SEQ ID NO 11
<211> LENGTH: 46
<212> TYPE: DNA
<213> ORGANISM: Artificial Sequence
<220> FEATURE:
<223> OTHER INFORMATION: Primer sequence - HuVK3-52 (K11)

<400> SEQUENCE: 11
tggcagctca gccagcgatg gctgaaatwg tgwtgacrca gtctcc          46

<210> SEQ ID NO 12
<211> LENGTH: 46
<212> TYPE: DNA
<213> ORGANISM: Artificial Sequence
<220> FEATURE:
<223> OTHER INFORMATION: Primer sequence - HuVK4-52 (K12)

<400> SEQUENCE: 12
tggcagctca gccagcgatg gctgacatcg tgatgaccca gtctcc          46

<210> SEQ ID NO 13
<211> LENGTH: 46
<212> TYPE: DNA
<213> ORGANISM: Artificial Sequence
<220> FEATURE:
<223> OTHER INFORMATION: Primer sequence - HuVK5-52 (K13)

<400> SEQUENCE: 13
tggcagctca gccagcgatg gctgaaacga cactcacgca gtctcc          46

<210> SEQ ID NO 14
<211> LENGTH: 46
<212> TYPE: DNA
<213> ORGANISM: Artificial Sequence
<220> FEATURE:
<223> OTHER INFORMATION: Primer sequence - HuVK6-52 (K14)

<400> SEQUENCE: 14
tggcagctca gccagcgatg gctgawrttg tgmtgacwca gtctcc          46

<210> SEQ ID NO 15
<211> LENGTH: 27
<212> TYPE: DNA
<213> ORGANISM: Artificial Sequence
<220> FEATURE:
<223> OTHER INFORMATION: Primer sequence - HuCk-31 (C1)

<400> SEQUENCE: 15
```

```
gatgaagaca gatggtgcag ccacagt                                    27

<210> SEQ ID NO 16
<211> LENGTH: 26
<212> TYPE: DNA
<213> ORGANISM: Artificial Sequence
<220> FEATURE:
<223> OTHER INFORMATION: Primer sequence - HuVL11-51 (L1)

<400> SEQUENCE: 16
gctcagtctg tgctgactca gccacc                                     26

<210> SEQ ID NO 17
<211> LENGTH: 26
<212> TYPE: DNA
<213> ORGANISM: Artificial Sequence
<220> FEATURE:
<223> OTHER INFORMATION: Primer sequence - HuVL12-51 (L2)

<400> SEQUENCE: 17
gctcagtctg tgytgacgca gccgcc                                     26

<210> SEQ ID NO 18
<211> LENGTH: 24
<212> TYPE: DNA
<213> ORGANISM: Artificial Sequence
<220> FEATURE:
<223> OTHER INFORMATION: Primeer sequence - HuVL2-51 (L3)

<400> SEQUENCE: 18
gctcagtctg ccctgactca gcct                                       24

<210> SEQ ID NO 19
<211> LENGTH: 26
<212> TYPE: DNA
<213> ORGANISM: Artificial Sequence
<220> FEATURE:
<223> OTHER INFORMATION: Primr sequence - HuVL31-51 (L4)

<400> SEQUENCE: 19
gcttcctatg wgctgacwca gccacc                                     26

<210> SEQ ID NO 20
<211> LENGTH: 26
<212> TYPE: DNA
<213> ORGANISM: Artificial Sequence
<220> FEATURE:
<223> OTHER INFORMATION: Primer sequence - HuVL32-51 (L5)

<400> SEQUENCE: 20
gcttcttctg agctgactca ggaccc                                     26

<210> SEQ ID NO 21
<211> LENGTH: 24
<212> TYPE: DNA
<213> ORGANISM: Artificial Sequence
<220> FEATURE:
<223> OTHER INFORMATION: Primer sequence - HuVL41-51 (L6)

<400> SEQUENCE: 21
gctctgcctg tgctgactca gccc                                       24

<210> SEQ ID NO 22
<211> LENGTH: 26
<212> TYPE: DNA
<213> ORGANISM: Artificial Sequence
```

```
<220> FEATURE:
<223> OTHER INFORMATION: Primer sequence - HuVL42-51 (L7)

<400> SEQUENCE: 22
gctcagcytg tgctgactca atcryc                                          26

<210> SEQ ID NO 23
<211> LENGTH: 23
<212> TYPE: DNA
<213> ORGANISM: Artificial Sequence
<220> FEATURE:
<223> OTHER INFORMATION: Primer sequence - HuVL5-51 (L8)

<400> SEQUENCE: 23
gctcagsctg tgctgactca gcc                                             23

<210> SEQ ID NO 24
<211> LENGTH: 26
<212> TYPE: DNA
<213> ORGANISM: Artificial Sequence
<220> FEATURE:
<223> OTHER INFORMATION: Primer sequence - HuVL6-51 (L9)

<400> SEQUENCE: 24 gctaattta tgctgactca gcccca                                           26

<210> SEQ ID NO 25
<211> LENGTH: 26
<212> TYPE: DNA
<213> ORGANISM: Artificial Sequence
<220> FEATURE:
<223> OTHER INFORMATION: Primer sequence - HuVL7/8-51 (L10)

<400> SEQUENCE: 25
gctcagrctg tggtgacyca ggagcc                                          26

<210> SEQ ID NO 26
<211> LENGTH: 26
<212> TYPE: DNA
<213> ORGANISM: Artificial Sequence
<220> FEATURE:
<223> OTHER INFORMATION: Primer sequence - HuVL9/10-51 (L11)

<400> SEQUENCE: 26
gctcagscwg kgctgactca gccacc                                          26

<210> SEQ ID NO 27
<211> LENGTH: 46
<212> TYPE: DNA
<213> ORGANISM: Artificial Sequence
<220> FEATURE:
<223> OTHER INFORMATION: Primer sequence - HuVL11-52 (L12)

<400> SEQUENCE: 27
tggcagctca gccagcgatg gctcagtctg tgctgactca gccacc                    46

<210> SEQ ID NO 28
<211> LENGTH: 46
<212> TYPE: DNA
<213> ORGANISM: Artificial Sequence
<220> FEATURE:
<223> OTHER INFORMATION: Primer sequence - HuVL12-52 (L13)

<400> SEQUENCE: 28
tggcagctca gccagcgatg gctcagtctg tgytgacgca gccgcc                    46
```

<210> SEQ ID NO 29
<211> LENGTH: 44
<212> TYPE: DNA
<213> ORGANISM: Artificial Sequence
<220> FEATURE:
<223> OTHER INFORMATION: Primer sequence - HuVL2-52 (L14)

<400> SEQUENCE: 29
tggcagctca gccagcgatg gctcagtctg ccctgactca gcct          44

<210> SEQ ID NO 30
<211> LENGTH: 46
<212> TYPE: DNA
<213> ORGANISM: Artificial Sequence
<220> FEATURE:
<223> OTHER INFORMATION: Primer sequence - HuVL31-52 (L15)

<400> SEQUENCE: 30
tggcagctca gccagcgatg gcttcctatg wgctgacwca gccacc        46

<210> SEQ ID NO 31
<211> LENGTH: 46
<212> TYPE: DNA
<213> ORGANISM: Artificial Sequence
<220> FEATURE:
<223> OTHER INFORMATION: Primer sequence - HuVL32-52 (L16)

<400> SEQUENCE: 31
tggcagctca gccagcgatg gcttcttctg agctgactca ggaccc        46

<210> SEQ ID NO 32
<211> LENGTH: 44
<212> TYPE: DNA
<213> ORGANISM: Artificial Sequence
<220> FEATURE:
<223> OTHER INFORMATION: Primer sequence - HuVL41-52 (L17)

<400> SEQUENCE: 32
tggcagctca gccagcgatg gctctgcctg tgctgactca gccc          44

<210> SEQ ID NO 33
<211> LENGTH: 46
<212> TYPE: DNA
<213> ORGANISM: Artificial Sequence
<220> FEATURE:
<223> OTHER INFORMATION: Primer sequence - HuVL42-52 (L18)

<400> SEQUENCE: 33
tggcagctca gccagcgatg gctcagcytg tgctgactca atcryc        46

<210> SEQ ID NO 34
<211> LENGTH: 43
<212> TYPE: DNA
<213> ORGANISM: Artificial Sequence
<220> FEATURE:
<223> OTHER INFORMATION: Primer sequence - HuVL5-52 (L19)

<400> SEQUENCE: 34
tggcagctca gccagcgatg gctcagsctg tgctgactca gcc           43

<210> SEQ ID NO 35
<211> LENGTH: 46
<212> TYPE: DNA
<213> ORGANISM: Artificial Sequence
<220> FEATURE:
<223> OTHER INFORMATION: Primer sequence - HuVL6-52 (L20)

```
<400> SEQUENCE: 35
tggcagctca gccagcgatg gctaattttta tgctgactca gcccca          46

<210> SEQ ID NO 36
<211> LENGTH: 46
<212> TYPE: DNA
<213> ORGANISM: Artificial Sequence
<220> FEATURE:
<223> OTHER INFORMATION: Primer sequence - HuVL7/8-52 (L21)

<400> SEQUENCE: 36
tggcagctca gccagcgatg gctcagrctg tggtgacyca ggagcc           46

<210> SEQ ID NO 37
<211> LENGTH: 46
<212> TYPE: DNA
<213> ORGANISM: Artificial Sequence
<220> FEATURE:
<223> OTHER INFORMATION: Primr sequence - HuVL9/10-52 (L22)

<400> SEQUENCE: 37
tggcagctca gccagcgatg gctcagscwg kgctgactca gccacc           46

<210> SEQ ID NO 38
<211> LENGTH: 27
<212> TYPE: DNA
<213> ORGANISM: Artificial Sequence
<220> FEATURE:
<223> OTHER INFORMATION: Primer sequence - HuCL-31 (C2)

<400> SEQUENCE: 38
gaccgagggg gcagccttgg gctgacc                                27

<210> SEQ ID NO 39
<211> LENGTH: 45
<212> TYPE: DNA
<213> ORGANISM: Artificial Sequence
<220> FEATURE:
<223> OTHER INFORMATION: Primer sequence - HuscFvJK140-31 (KS1)

<400> SEQUENCE: 39
accgccaccg gatccacccc cacctttgat ytccaccttg gtccc            45

<210> SEQ ID NO 40
<211> LENGTH: 45
<212> TYPE: DNA
<213> ORGANISM: Artificial Sequence
<220> FEATURE:
<223> OTHER INFORMATION: Primeer sequence - HuscFvJK20-31 (KS2)

<400> SEQUENCE: 40
accgccaccg gatccacccc caccttttgat ctccagcttg gtccc           45

<210> SEQ ID NO 41
<211> LENGTH: 45
<212> TYPE: DNA
<213> ORGANISM: Artificial Sequence
<220> FEATURE:
<223> OTHER INFORMATION: Primer sequence - HuscFvJK30-31 (KS3)

<400> SEQUENCE: 41
accgccaccg gatccacccc cacctttgat atccactttg gtccc            45

<210> SEQ ID NO 42
```

<210> SEQ ID NO 42
<211> LENGTH: 45
<212> TYPE: DNA
<213> ORGANISM: Artificial Sequence
<220> FEATURE:
<223> OTHER INFORMATION: Primer sequence - HuscFvJK50-31 (KS4)

<400> SEQUENCE: 42
accgccaccg gatccacccc cacctttaat ctccagtcgt gtccc         45

<210> SEQ ID NO 43
<211> LENGTH: 45
<212> TYPE: DNA
<213> ORGANISM: Artificial Sequence
<220> FEATURE:
<223> OTHER INFORMATION: Primer sequence - HuscFvJL1236-31 (LS1)

<400> SEQUENCE: 43
accgccaccg gatccacccc cacctaggac ggtcascttg gtscc         45

<210> SEQ ID NO 44
<211> LENGTH: 45
<212> TYPE: DNA
<213> ORGANISM: Artificial Sequence
<220> FEATURE:
<223> OTHER INFORMATION: Primer sequence - HuscFvJL4-31 (LS2)

<400> SEQUENCE: 44
accgccaccg gatccacccc cacctaaaat gatcagctgg gttcc         45

<210> SEQ ID NO 45
<211> LENGTH: 45
<212> TYPE: DNA
<213> ORGANISM: Artificial Sequence
<220> FEATURE:
<223> OTHER INFORMATION: Primer sequence - HuscFvJL57-31 (LS3)

<400> SEQUENCE: 45
accgccaccg gatccacccc caccgaggac ggtcagctsg gtscc         45

<210> SEQ ID NO 46
<211> LENGTH: 29
<212> TYPE: DNA
<213> ORGANISM: Artificial Sequence
<220> FEATURE:
<223> OTHER INFORMATION: Primer sequence - HuscFvVH1-51 (H1)

<400> SEQUENCE: 46
ggaagccagg tbcagctggt gcagtctgg              29

<210> SEQ ID NO 47
<211> LENGTH: 29
<212> TYPE: DNA
<213> ORGANISM: Artificial Sequence
<220> FEATURE:
<223> OTHER INFORMATION: Primer sequence - HuscFvVH1/7-51 (H2)

<400> SEQUENCE: 47
ggaagccarr tscagctggt rcartctgg              29

<210> SEQ ID NO 48
<211> LENGTH: 29
<212> TYPE: DNA
<213> ORGANISM: Artificial Sequence
<220> FEATURE:
<223> OTHER INFORMATION: Primer sequence - HuscFvVH2-51 (H3)

<400> SEQUENCE: 48
ggaagccagr tcaccttgaa ggagtctgg     29

<210> SEQ ID NO 49
<211> LENGTH: 29
<212> TYPE: DNA
<213> ORGANISM: Artificial Sequence
<220> FEATURE:
<223> OTHER INFORMATION: Primer sequence - HuscFvVH31-51 (H4)

<400> SEQUENCE: 49
ggaagcsarg tgcagctggt gcagtctgg     29

<210> SEQ ID NO 50
<211> LENGTH: 29
<212> TYPE: DNA
<213> ORGANISM: Artificial Sequence
<220> FEATURE:
<223> OTHER INFORMATION: Primer sequence - HuscFvVH32-51 (H5)

<400> SEQUENCE: 50
ggaagcgagg tgcagctgkt ggagwcysg     29

<210> SEQ ID NO 51
<211> LENGTH: 29
<212> TYPE: DNA
<213> ORGANISM: Artificial Sequence
<220> FEATURE:
<223> OTHER INFORMATION: Primer sequence - HuscFvVH41-51 (H6)

<400> SEQUENCE: 51
ggaagccagg tgcarctgca ggagtcggg     29

<210> SEQ ID NO 52
<211> LENGTH: 29
<212> TYPE: DNA
<213> ORGANISM: Artificial Sequence
<220> FEATURE:
<223> OTHER INFORMATION: Primer sequence - HuscFvVH42-51 (H7)

<400> SEQUENCE: 52
ggaagccags tgcagctrca gsagtssgg     29

<210> SEQ ID NO 53
<211> LENGTH: 29
<212> TYPE: DNA
<213> ORGANISM: Artificial Sequence
<220> FEATURE:
<223> OTHER INFORMATION: Primer sequence - HuscFvVH5-51 (H8)

<400> SEQUENCE: 53
ggaagcgarg tgcagctggt gcagtctgg     29

<210> SEQ ID NO 54
<211> LENGTH: 29
<212> TYPE: DNA
<213> ORGANISM: Artificial Sequence
<220> FEATURE:
<223> OTHER INFORMATION: Primer sequence - HuscFvVH6-51 (H9)

<400> SEQUENCE: 54
ggaagccagg tacagctgca gcagtcagg     29

<210> SEQ ID NO 55
<211> LENGTH: 68
<212> TYPE: DNA

```
<213> ORGANISM: Artificial Sequence
<220> FEATURE:
<223> OTHER INFORMATION: Primer sequence - HuscFvVH1-52 (H10)

<400> SEQUENCE: 55
ggtgggggtg atccggtgg cggtggctct ggaggcggtg aagccaggt bcagctggtg      60 cagtctgg                                                             68

<210> SEQ ID NO 56
<211> LENGTH: 68
<212> TYPE: DNA
<213> ORGANISM: Artificial Sequence
<220> FEATURE:
<223> OTHER INFORMATION: Primer sequence - HuscFvVH1/7-52 (H11)

<400> SEQUENCE: 56
ggtgggggtg atccggtgg cggtggctct ggaggcggtg aagccarrt scagctggtr      60 cartctgg                                                             68

<210> SEQ ID NO 57
<211> LENGTH: 68
<212> TYPE: DNA
<213> ORGANISM: Artificial Sequence
<220> FEATURE:
<223> OTHER INFORMATION: Primer sequence - HuscFvVH2-52 (H12)

<400> SEQUENCE: 57
ggtgggggtg atccggtgg cggtggctct ggaggcggtg aagccagrt caccttgaag      60 gagtctgg                                                             68

<210> SEQ ID NO 58
<211> LENGTH: 68
<212> TYPE: DNA
<213> ORGANISM: Artificial Sequence
<220> FEATURE:
<223> OTHER INFORMATION: Primer sequence - HuscFvVH31-52 (H13)

<400> SEQUENCE: 58
ggtgggggtg atccggtgg cggtggctct ggaggcggtg aagcsargt gcagctggtg      60 cagtctgg                                                             68

<210> SEQ ID NO 59
<211> LENGTH: 68
<212> TYPE: DNA
<213> ORGANISM: Artificial Sequence
<220> FEATURE:
<223> OTHER INFORMATION: Primer sequence - HuscFvVH32-52 (H14)

<400> SEQUENCE: 59
ggtgggggtg atccggtgg cggtggctct ggaggcggtg aagcgaggt gcagctgktg      60 gagwcysg                                                             68

<210> SEQ ID NO 60
<211> LENGTH: 68
<212> TYPE: DNA
<213> ORGANISM: Artificial Sequence
<220> FEATURE:
<223> OTHER INFORMATION: Primer sequence - HuscFvVH41-52 (H15)

<400> SEQUENCE: 60
ggtgggggtg atccggtgg cggtggctct ggaggcggtg aagccaggt gcarctgcag      60 gagtcggg                                                             68
```

<210> SEQ ID NO 61
<211> LENGTH: 68
<212> TYPE: DNA
<213> ORGANISM: Artificial Sequence
<220> FEATURE:
<223> OTHER INFORMATION: Primer sequence - HuscFvVH42-52 (H16)

<400> SEQUENCE: 61 ggtggggggtg atccggtgg cggtggctct ggaggcggtg aagccagst gcagctrcag    60 sagtssgg                                                             68

<210> SEQ ID NO 62
<211> LENGTH: 68
<212> TYPE: DNA
<213> ORGANISM: Artificial Sequence
<220> FEATURE:
<223> OTHER INFORMATION: Primer sequence - HuscFvVH5-52 (H17)

<400> SEQUENCE: 62 ggtggggggtg atccggtgg cggtggctct ggaggcggtg aagcgargt gcagctggtg    60 cagtctgg                                                             68

<210> SEQ ID NO 63
<211> LENGTH: 68
<212> TYPE: DNA
<213> ORGANISM: Artificial Sequence
<220> FEATURE:
<223> OTHER INFORMATION: Primr sequence - HuscFvVH6-52 (H18)

<400> SEQUENCE: 63 ggtggggggtg atccggtgg cggtggctct ggaggcggtg aagccaggt acagctgcag    60 cagtcagg                                                             68

<210> SEQ ID NO 64
<211> LENGTH: 33
<212> TYPE: DNA
<213> ORGANISM: Artificial Sequence
<220> FEATURE:
<223> OTHER INFORMATION: Primer sequence - HuJM-32

<400> SEQUENCE: 64
ggggcggatg cactccctga ggagacggtg acc                                 33

<210> SEQ ID NO 65
<211> LENGTH: 33
<212> TYPE: DNA
<213> ORGANISM: Artificial Sequence
<220> FEATURE:
<223> OTHER INFORMATION: Primer sequence - HuJG-33

<400> SEQUENCE: 65 gggcccttttg tactcgctga ggagacggtg acc                                33

<210> SEQ ID NO 66
<211> LENGTH: 23
<212> TYPE: DNA
<213> ORGANISM: Artificial Sequence
<220> FEATURE:
<223> OTHER INFORMATION: Primer sequence - PelBclo-51

<400> SEQUENCE: 66
tggcagctca gccagcgatg gct                                            23

<210> SEQ ID NO 67
<211> LENGTH: 31
<212> TYPE: DNA
<213> ORGANISM: Artificial Sequence
<220> FEATURE:
<223> OTHER INFORMATION: Primer sequence - HuJgclo-34

<400> SEQUENCE: 67
cgctagggcc ctttgtactc gctgaggaga c                          31

<210> SEQ ID NO 68
<211> LENGTH: 308
<212> TYPE: PRT
<213> ORGANISM: Artificial Sequence
<220> FEATURE:
<223> OTHER INFORMATION: Amino acid sequence of MTC28 protein

<400> SEQUENCE: 68

Gly Ala Ser Gly Ser Asp Pro Leu Leu Pro Pro Pro Ile Pro Ala
1               5                   10                  15

Pro Val Ser Ala Pro Ala Thr Val Pro Pro Val Gln Asn Leu Thr Ala
                20                  25                  30

Leu Pro Gly Gly Ser Ser Asn Arg Phe Ser Pro Ala Pro Ala Pro Ala
            35                  40                  45

Pro Ile Ala Ser Pro Ile Pro Val Gly Ala Pro Gly Ser Thr Ala Val
        50                  55                  60

Pro Pro Leu Pro Pro Pro Val Thr Pro Ala Ile Ser Gly Thr Leu Arg
65                  70                  75                  80

Asp His Leu Arg Glu Lys Gly Val Lys Leu Glu Ala Gln Arg Pro His
                85                  90                  95

Gly Phe Lys Ala Leu Asp Ile Thr Leu Pro Met Pro Pro Arg Trp Thr
            100                 105                 110

Gln Val Pro Asp Pro Asn Val Pro Asp Ala Phe Val Val Ile Ala Asp
        115                 120                 125

Arg Leu Gly Asn Ser Val Tyr Thr Ser Asn Ala Gln Leu Val Val Tyr
    130                 135                 140

Arg Leu Ile Gly Asp Phe Asp Pro Ala Glu Ala Ile Thr His Gly Tyr
145                 150                 155                 160

Ile Asp Ser Gln Lys Leu Leu Ala Trp Gln Thr Thr Asn Ala Ser Met
                165                 170                 175

Ala Asn Phe Asp Gly Phe Pro Ser Ser Ile Ile Glu Gly Thr Tyr Arg
            180                 185                 190

Glu Asn Asp Met Thr Leu Asn Thr Ser Arg Arg His Val Ile Ala Thr
        195                 200                 205

Ser Gly Ala Asp Lys Tyr Leu Val Ser Leu Ser Val Thr Thr Ala Leu
    210                 215                 220

Ser Gln Ala Val Thr Asp Gly Pro Ala Thr Asp Ala Ile Val Asn Gly
225                 230                 235                 240

Phe Gln Val Val Ala His Ala Ala Pro Ala Gln Ala Pro Ala Pro Ala
                245                 250                 255

Pro Gly Ser Ala Pro Val Gly Leu Pro Gly Gln Ala Pro Gly Tyr Pro
            260                 265                 270

Pro Ala Gly Thr Leu Thr Pro Val Pro Pro Arg Gly Gly Gly Ala Ser
        275                 280                 285

Gly Gly Ala Pro Gly Gly Leu Asn Asp Ile Phe Glu Ala Gln Lys Ile
    290                 295                 300

-continued

```
Glu Trp His Glu
305

<210> SEQ ID NO 69
<211> LENGTH: 924
<212> TYPE: PRT
<213> ORGANISM: Artificial Sequence
<220> FEATURE:
<223> OTHER INFORMATION: Nucleic acid sequence of MTC28-DNA

<400> SEQUENCE: 69

Gly Gly Thr Gly Cys Thr Ala Gly Cys Gly Gly Cys Ala Gly Cys Gly
1               5                   10                  15

Ala Thr Cys Cys Cys Cys Thr Gly Cys Thr Gly Cys Cys Ala Cys Cys
            20                  25                  30

Gly Cys Cys Gly Cys Cys Thr Ala Thr Cys Cys Cys Thr Gly Cys Cys
        35                  40                  45

Cys Cys Ala Gly Thr Cys Thr Cys Gly Gly Cys Gly Cys Cys Gly Gly
    50                  55                  60

Cys Ala Ala Cys Ala Gly Thr Cys Cys Cys Gly Cys Cys Cys Gly Thr
65                  70                  75                  80

Gly Cys Ala Gly Ala Ala Cys Cys Thr Cys Ala Cys Gly Gly Cys Gly
                85                  90                  95

Cys Thr Thr Cys Cys Gly Gly Gly Cys Gly Gly Gly Ala Gly Cys Ala
            100                 105                 110

Gly Cys Ala Ala Cys Ala Gly Gly Thr Thr Cys Thr Cys Ala Cys Cys
        115                 120                 125

Gly Gly Cys Gly Cys Cys Ala Gly Cys Ala Cys Cys Cys Gly Cys Ala
    130                 135                 140

Cys Cys Gly Ala Thr Cys Gly Cys Gly Thr Cys Gly Cys Cys Gly Ala
145                 150                 155                 160

Thr Thr Cys Cys Gly Gly Thr Cys Gly Gly Ala Gly Cys Ala Cys Cys
                165                 170                 175

Cys Gly Gly Gly Thr Cys Cys Ala Cys Cys Gly Cys Thr Gly Thr Gly
            180                 185                 190

Cys Cys Cys Cys Cys Gly Cys Thr Gly Cys Cys Gly Cys Cys Gly Cys
        195                 200                 205

Cys Ala Gly Thr Gly Ala Cys Thr Cys Cys Cys Gly Cys Gly Ala Thr
    210                 215                 220

Cys Ala Gly Cys Gly Gly Cys Ala Cys Ala Cys Thr Thr Cys Gly Gly
225                 230                 235                 240

Gly Ala Cys Cys Ala Cys Cys Thr Cys Cys Gly Gly Gly Ala Gly Ala
                245                 250                 255

Ala Gly Gly Gly Cys Gly Thr Cys Ala Ala Gly Cys Thr Gly Gly Ala
            260                 265                 270

Gly Gly Cys Ala Cys Ala Gly Cys Gly Ala Cys Cys Gly Cys Ala Cys
        275                 280                 285

Gly Gly Ala Thr Thr Cys Ala Ala Gly Gly Cys Gly Cys Thr Cys Gly
    290                 295                 300

Ala Cys Ala Thr Cys Ala Cys Ala Cys Thr Gly Cys Cys Cys Ala Thr
305                 310                 315                 320

Gly Cys Cys Gly Cys Cys Gly Cys Gly Cys Thr Gly Gly Ala Cys Thr
                325                 330                 335

Cys Ala Gly Gly Thr Gly Cys Cys Cys Gly Ala Cys Cys Cys Cys Ala
            340                 345                 350
```

-continued

```
Ala Cys Gly Thr Gly Cys Cys Gly Ala Cys Cys Gly Thr Thr
            355                 360                 365

Cys Gly Thr Gly Gly Thr Gly Ala Thr Cys Gly Cys Gly Ala Cys
            370                 375                 380

Cys Gly Gly Thr Thr Gly Gly Gly Cys Ala Ala Cys Ala Gly Cys Gly
385                 390                 395                 400

Thr Cys Thr Ala Cys Ala Cys Gly Thr Cys Gly Ala Ala Thr Gly Cys
                405                 410                 415

Gly Cys Ala Gly Cys Thr Gly Gly Thr Ala Gly Thr Gly Thr Ala Thr
                420                 425                 430

Ala Gly Gly Cys Thr Gly Ala Thr Cys Gly Gly Thr Gly Ala Cys Thr
                435                 440                 445

Thr Cys Gly Ala Thr Cys Cys Gly Cys Thr Gly Ala Gly Gly Cys
            450                 455                 460

Cys Ala Thr Cys Ala Cys Ala Cys Gly Gly Cys Thr Ala Cys
465                 470                 475                 480

Ala Thr Thr Gly Ala Cys Ala Gly Cys Cys Ala Gly Ala Ala Ala Thr
                485                 490                 495

Thr Gly Cys Thr Cys Gly Cys Ala Thr Gly Gly Cys Ala Gly Ala Cys
            500                 505                 510

Cys Ala Cys Ala Ala Ala Cys Gly Cys Cys Thr Cys Gly Ala Thr Gly
515                 520                 525

Gly Cys Cys Ala Ala Thr Thr Thr Cys Gly Ala Cys Gly Gly Cys Thr
            530                 535                 540

Thr Thr Cys Cys Gly Thr Cys Ala Thr Cys Ala Ala Thr Cys Ala Thr
545                 550                 555                 560

Cys Gly Ala Gly Gly Gly Cys Ala Cys Cys Thr Ala Cys Cys Gly Cys
            565                 570                 575

Gly Ala Ala Ala Cys Gly Ala Cys Ala Thr Gly Ala Cys Cys Cys
            580                 585                 590

Thr Cys Ala Ala Cys Ala Cys Cys Thr Cys Cys Gly Gly Cys Gly
            595                 600                 605

Cys Cys Ala Cys Gly Thr Cys Ala Thr Cys Gly Cys Ala Cys Cys
610                 615                 620

Thr Cys Cys Gly Gly Ala Gly Cys Cys Gly Ala Cys Ala Ala Gly Thr
625                 630                 635                 640

Ala Cys Cys Thr Gly Gly Thr Thr Thr Cys Gly Cys Thr Gly Thr Cys
            645                 650                 655

Gly Gly Thr Gly Ala Cys Cys Ala Cys Cys Gly Cys Gly Cys Thr Gly
            660                 665                 670

Thr Cys Gly Cys Ala Gly Gly Cys Gly Gly Thr Cys Ala Cys Cys Gly
            675                 680                 685

Ala Cys Gly Gly Gly Cys Cys Gly Gly Cys Cys Ala Cys Cys Gly Ala
            690                 695                 700

Thr Gly Cys Gly Ala Thr Thr Gly Thr Cys Ala Ala Cys Gly Gly Ala
705                 710                 715                 720

Thr Thr Cys Cys Ala Ala Gly Thr Gly Gly Thr Thr Gly Cys Gly Cys
            725                 730                 735

Ala Thr Gly Cys Gly Gly Gly Cys Gly Cys Cys Gly Cys Thr Cys Ala
            740                 745                 750

Gly Gly Cys Gly Cys Cys Thr Gly Cys Cys Cys Gly Gly Cys Ala
            755                 760                 765

Cys Cys Cys Gly Gly Thr Thr Cys Gly Gly Cys Ala Cys Cys Gly Gly
```

```
                    770                 775                 780
Thr Gly Gly Gly Ala Cys Thr Ala Cys Cys Cys Gly Gly Cys Ala
785                 790                 795                 800

Gly Gly Cys Gly Cys Cys Thr Gly Gly Thr Ala Thr Cys Cys Gly
                    805                 810                 815

Cys Cys Cys Gly Cys Gly Gly Cys Ala Cys Cys Thr Gly Ala
                    820                 825                 830

Cys Ala Cys Cys Ala Gly Thr Cys Cys Gly Cys Cys Gly Cys Gly
                    835                 840                 845

Cys Gly Gly Thr Gly Gly Ala Gly Gly Cys Gly Cys Thr Cys Ala
                    850                 855                 860

Gly Gly Cys Gly Gly Cys Gly Cys Gly Cys Cys Thr Gly Gly Ala Gly
865                 870                 875                 880

Gly Thr Cys Thr Gly Ala Ala Cys Gly Ala Cys Ala Thr Cys Thr Thr
                    885                 890                 895

Cys Gly Ala Gly Gly Cys Thr Cys Ala Gly Ala Ala Ala Ala Thr Cys
                    900                 905                 910

Gly Ala Ala Thr Gly Gly Cys Ala Cys Gly Ala Gly
        915                 920
```

<210> SEQ ID NO 70
<211> LENGTH: 160
<212> TYPE: PRT
<213> ORGANISM: Artificial Sequence
<220> FEATURE:
<223> OTHER INFORMATION: Amino acid sequence of MPT63 protein

<400> SEQUENCE: 70

```
Gly Ala Ser Gly Ser Ala Tyr Pro Ile Thr Gly Lys Leu Gly Ser Glu
1               5                   10                  15

Leu Thr Met Thr Asp Thr Val Gly Gln Val Leu Gly Trp Lys Val
                20                  25                  30

Ser Asp Leu Lys Ser Ser Thr Ala Val Ile Pro Gly Tyr Pro Val Ala
            35                  40                  45

Gly Gln Val Trp Glu Ala Thr Ala Thr Val Asn Ala Ile Arg Gly Ser
        50                  55                  60

Val Thr Pro Ala Val Ser Gln Phe Asn Ala Arg Thr Ala Asp Gly Ile
65                  70                  75                  80

Asn Tyr Arg Val Leu Trp Gln Ala Ala Gly Pro Asp Thr Ile Ser Gly
                85                  90                  95

Ala Thr Ile Pro Gln Gly Glu Gln Ser Thr Gly Lys Ile Tyr Phe Asp
            100                 105                 110

Val Thr Gly Pro Ser Pro Thr Ile Val Ala Met Asn Asn Gly Met Glu
        115                 120                 125

Asp Leu Leu Ile Trp Glu Pro Gly Gly Gly Ala Ser Gly Gly Ala Pro
130                 135                 140

Gly Gly Leu Asn Asp Ile Phe Glu Ala Gln Lys Ile Glu Trp His Glu
145                 150                 155                 160
```

<210> SEQ ID NO 71
<211> LENGTH: 480
<212> TYPE: DNA
<213> ORGANISM: Artificial Sequence
<220> FEATURE:
<223> OTHER INFORMATION: Nucleic acid sequence of MPT63-DNA

<400> SEQUENCE: 71

```
ggtgctagcg gcagcgccta tcccatcacc ggaaaacttg gcagtgagct aacgatgacc    60
gacaccgttg gccaagtcgt gctcggctgg aaggtcagtg atctcaaatc cagcacggca   120 gtcatcccg  gctatccggt ggccggccag gtctgggagg ccactgccac ggtcaatgcg   180
attcgcggca gcgtcacgcc cgcggtctcg cagttcaatg cccgcaccgc cgacggcatc   240
aactaccggg tgctgtggca agccgcgggc cccgacacca ttagcggagc cactatcccc   300
caaggcgaac aatcgaccgg caaaatctac ttcgatgtca ccggcccatc gccaaccatc   360
gtcgcgatga caacggcat  ggaggatctg ctgatttggg agccgggtgg aggcgcctca   420
ggcggcgcgc ctggaggtct gaacgacatc ttcgaggctc agaaaatcga atggcacgag   480
```

<210> SEQ ID NO 72
<211> LENGTH: 235
<212> TYPE: PRT
<213> ORGANISM: Artificial Sequence
<220> FEATURE:
<223> OTHER INFORMATION: Amino acid sequence of MPT64 protein

<400> SEQUENCE: 72

```
Gly Ala Ser Gly Ser Ala Pro Lys Thr Tyr Cys Glu Glu Leu Lys Gly
1               5                  10                  15

Thr Asp Thr Gly Gln Ala Cys Gln Ile Gln Met Ser Asp Pro Ala Tyr
            20                  25                  30

Asn Ile Asn Ile Ser Leu Pro Ser Tyr Tyr Pro Asp Gln Lys Ser Leu
        35                  40                  45

Glu Asn Tyr Ile Ala Gln Thr Arg Asp Lys Phe Leu Ser Ala Ala Thr
    50                  55                  60

Ser Ser Thr Pro Arg Glu Ala Pro Tyr Glu Leu Asn Ile Thr Ser Ala
65                  70                  75                  80

Thr Tyr Gln Ser Ala Ile Pro Pro Arg Gly Thr Gln Ala Val Val Leu
                85                  90                  95

Lys Val Tyr Gln Asn Ala Gly Gly Thr His Pro Thr Thr Thr Tyr Lys
            100                 105                 110

Ala Phe Asp Trp Asp Gln Ala Tyr Arg Lys Pro Ile Thr Tyr Asp Thr
        115                 120                 125

Leu Trp Gln Ala Asp Thr Asp Pro Leu Pro Val Val Phe Pro Ile Val
    130                 135                 140

Gln Gly Glu Leu Ser Lys Gln Thr Gly Gln Gln Val Ser Ile Ala Pro
145                 150                 155                 160

Asn Ala Gly Leu Asp Pro Val Asn Tyr Gln Asn Phe Ala Val Thr Asn
                165                 170                 175

Asp Gly Val Ile Phe Phe Phe Asn Pro Gly Glu Leu Leu Pro Glu Ala
            180                 185                 190

Ala Gly Pro Thr Gln Val Leu Val Pro Arg Ser Ala Ile Asp Ser Met
        195                 200                 205

Leu Ala Gly Gly Ala Ser Gly Gly Ala Pro Gly Gly Leu Asn Asp
    210                 215                 220

Ile Phe Glu Ala Gln Lys Ile Glu Trp His Glu
225                 230                 235
```

<210> SEQ ID NO 73
<211> LENGTH: 705
<212> TYPE: DNA
<213> ORGANISM: Artificial Sequence
<220> FEATURE:
<223> OTHER INFORMATION: Nucleic acid sequence of MPT64-DNA

<400> SEQUENCE: 73

```
ggtgctagcg gcagcgcgcc caagacctac tgcgaggagt tgaaaggcac cgataccggc      60
caggcgtgcc agattcaaat gtccgacccg gcctacaaca tcaacatcag cctgcccagt     120
tactaccccg accagaagtc gctggaaaat tacatcgccc agacgcgcga caagttcctc     180
agcgcggcca catcgtccac tccacgcgaa gcccctacg aattgaatat cacctcggcc      240
acataccagt ccgcgatacc gccgcgtggt acgcaggccg tggtgctcaa ggtctaccag     300
aacgccggcg gcacgcaccc aacgaccacg tacaaggcct tcgattggga ccaggcctat     360
cgcaagccaa tcacctatga cacgctgtgg caggctgaca ccgatccgct gccagtcgtc     420
ttccccattg tgcaaggtga actgagcaag cagaccggac aacaggtatc gatagcgccg     480
aatgccggct tggaccccggt gaattatcag aacttcgcag tcacgaacga cggggtgatt     540
ttcttcttca acccggggga gttgctgccc gaagcagccg gcccaaccca ggtattggtc     600
ccacgttccg cgatcgactc gatgctggcc ggtggaggcg cctcaggcgg cgcgcctgga     660
ggtctgaacg acatcttcga ggctcagaaa atcgaatggc acgag                     705
```

<210> SEQ ID NO 74
<211> LENGTH: 325
<212> TYPE: PRT
<213> ORGANISM: Artificial Sequence
<220> FEATURE:
<223> OTHER INFORMATION: Amino acid sequence of Ag85A-protein

<400> SEQUENCE: 74

```
Gly Ala Ser Gly Ser Phe Ser Arg Pro Gly Leu Pro Val Glu Tyr Leu
1               5                   10                  15

Gln Val Pro Ser Pro Ser Met Gly Arg Asp Ile Lys Val Gln Phe Gln
            20                  25                  30

Ser Gly Gly Ala Asn Ser Pro Ala Leu Tyr Leu Leu Asp Gly Leu Arg
        35                  40                  45

Ala Gln Asp Asp Phe Ser Gly Trp Asp Ile Asn Thr Pro Ala Phe Glu
    50                  55                  60

Trp Tyr Asp Gln Ser Gly Leu Ser Val Val Met Pro Val Gly Gly Gln
65                  70                  75                  80

Ser Ser Phe Tyr Ser Asp Trp Tyr Gln Pro Ala Cys Gly Lys Ala Gly
                85                  90                  95

Cys Gln Thr Tyr Lys Trp Glu Thr Phe Leu Thr Ser Glu Leu Pro Gly
            100                 105                 110

Trp Leu Gln Ala Asn Arg His Val Lys Pro Thr Gly Ser Ala Val Val
        115                 120                 125

Gly Leu Ser Met Ala Ala Ser Ser Ala Leu Thr Leu Ala Ile Tyr His
    130                 135                 140

Pro Gln Gln Phe Val Tyr Ala Gly Ala Met Ser Gly Leu Leu Asp Pro
145                 150                 155                 160

Ser Gln Ala Met Gly Pro Thr Leu Ile Gly Leu Ala Met Gly Asp Ala
                165                 170                 175

Gly Gly Tyr Lys Ala Ser Asp Met Trp Gly Pro Lys Glu Asp Pro Ala
            180                 185                 190

Trp Gln Arg Asn Asp Pro Leu Leu Asn Val Gly Lys Leu Ile Ala Asn
        195                 200                 205

Asn Thr Arg Val Trp Val Tyr Cys Gly Asn Gly Lys Pro Ser Asp Leu
    210                 215                 220

Gly Gly Asn Asn Leu Pro Ala Lys Phe Leu Glu Gly Phe Val Arg Thr
```

```
                225                 230                 235                 240
Ser Asn Ile Lys Phe Gln Asp Ala Tyr Asn Ala Gly Gly His Asn
                    245                 250                 255

Gly Val Phe Asp Phe Pro Asp Ser Gly Thr His Ser Trp Glu Tyr Trp
                260                 265                 270

Gly Ala Gln Leu Asn Ala Met Lys Pro Asp Leu Gln Arg Ala Leu Gly
                275                 280                 285

Ala Thr Pro Asn Thr Gly Pro Ala Pro Gln Gly Ala Gly Gly Ala
                290                 295                 300

Ser Gly Gly Ala Pro Gly Gly Leu Asn Asp Ile Phe Glu Ala Gln Lys
305                 310                 315                 320

Ile Glu Trp His Glu
                325

<210> SEQ ID NO 75
<211> LENGTH: 975
<212> TYPE: DNA
<213> ORGANISM: Artificial Sequence
<220> FEATURE:
<223> OTHER INFORMATION: Nucleic acid seqeunce of Ag85A-DNA

<400> SEQUENCE: 75
ggtgctagcg gcagctttc ccggccgggc ttgccggtgg agtacctgca ggtgccgtcg      60
ccgtcgatgg gccgtgacat caaggtccaa ttccaaagtg gtggtgccaa ctcgcccgcc     120
ctgtacctgc tcgacggcct gcgcgcgcag gacgacttca gcggctggga catcaacacc     180
ccggcgttcg agtggtacga ccagtcgggc ctgtcggtgg tcatgccggt gggtggccag     240
tcaagcttct actccgactg gtaccagccc gcctgcggca aggccggttg ccagacttac     300
aagtgggaga ccttcctgac cagcgagctg ccggggtggc tgcaggccaa caggcacgtc     360
aagcccaccg gaagcgccgt cgtcggtctt tcgatggctg cttcttcggc gctgacgctg     420
gcgatctatc acccccagca gttcgtctac gcgggagcga tgtcgggcct gttgacccc      480 tcccaggcga tgggtcccac cctgatcggc ctggcgatgg gtgacgctgg cggctacaag     540
gcctccgaca tgtggggccc gaaggaggac ccggcgtggc agcgcaacga cccgctgttg     600
aacgtcggga agctgatcgc caacaacacc cgcgtctggg tgtactgcgg caacggcaag     660
ccgtcggatc tgggtggcaa caacctgccg gccaagttcc tcgagggctt cgtgcggacc     720
agcaacatca gttccaaga cgcctacaac gccggtggcg gccacaacgg cgtgttcgac     780
ttcccggaca gcggtacgca cagctgggag tactgggggcg cgcagctcaa cgctatgaag     840
cccgacctgc aacgggcact gggtgccacg cccaacaccg gcccgcgcc ccagggcgcc     900 ggtggaggcg cctcaggcgg cgcgcctgga ggtctgaacg acatcttcga ggctcagaaa     960
atcgaatggc acgag                                                      975

<210> SEQ ID NO 76
<211> LENGTH: 315
<212> TYPE: PRT
<213> ORGANISM: Artificial Sequence
<220> FEATURE:
<223> OTHER INFORMATION: Amino acid sequence of Ag85B-protein

<400> SEQUENCE: 76

Gly Ala Ser Gly Ser Phe Ser Arg Pro Gly Leu Pro Val Glu Tyr Leu
1               5                   10                  15

Gln Val Pro Ser Pro Ser Met Gly Arg Asp Ile Lys Val Gln Phe Gln
                20                  25                  30
```

```
Ser Gly Gly Asn Asn Ser Pro Ala Val Tyr Leu Leu Asp Gly Leu Arg
        35                  40                  45

Ala Gln Asp Asp Tyr Asn Gly Trp Asp Ile Asn Thr Pro Ala Phe Glu
    50                  55                  60

Trp Tyr Tyr Gln Ser Gly Leu Ser Ile Val Met Pro Val Gly Gly Gln
65                  70                  75                  80

Ser Ser Phe Tyr Ser Asp Trp Tyr Ser Pro Ala Cys Gly Lys Ala Gly
                85                  90                  95

Cys Gln Thr Tyr Lys Trp Glu Thr Phe Leu Thr Ser Glu Leu Pro Gln
            100                 105                 110

Trp Leu Ser Ala Asn Arg Ala Val Lys Pro Thr Gly Ser Ala Ala Ile
        115                 120                 125

Gly Leu Ser Met Ala Gly Ser Ser Ala Met Ile Leu Ala Ala Tyr His
    130                 135                 140

Pro Gln Gln Phe Ile Tyr Ala Gly Ser Leu Ser Ala Leu Leu Asp Pro
145                 150                 155                 160

Ser Gln Gly Met Gly Pro Ser Leu Ile Gly Leu Ala Met Gly Asp Ala
                165                 170                 175

Gly Gly Tyr Lys Ala Ala Asp Met Trp Gly Pro Ser Ser Asp Pro Ala
            180                 185                 190

Trp Glu Arg Asn Asp Pro Thr Gln Gln Ile Pro Lys Leu Val Ala Asn
        195                 200                 205

Asn Thr Arg Leu Trp Val Tyr Cys Gly Asn Gly Thr Pro Asn Glu Leu
    210                 215                 220

Gly Gly Ala Asn Ile Pro Ala Glu Phe Leu Glu Asn Phe Val Arg Ser
225                 230                 235                 240

Ser Asn Leu Lys Phe Gln Asp Ala Tyr Asn Ala Ala Gly Gly His Asn
                245                 250                 255

Ala Val Phe Asn Phe Pro Pro Asn Gly Thr His Ser Trp Glu Tyr Trp
            260                 265                 270

Gly Ala Gln Leu Asn Ala Met Lys Gly Asp Leu Gln Ser Ser Leu Gly
        275                 280                 285

Ala Gly Gly Gly Gly Ala Ser Gly Gly Ala Pro Gly Leu Asn Asp
    290                 295                 300

Ile Phe Glu Ala Gln Lys Ile Glu Trp His Glu
305                 310                 315

<210> SEQ ID NO 77
<211> LENGTH: 945
<212> TYPE: DNA
<213> ORGANISM: Artificial Sequence
<220> FEATURE:
<223> OTHER INFORMATION: Nucleic acid sequence of Ag85B-DNA

<400> SEQUENCE: 77
ggtgctagcg gcagcttctc ccggccgggg ctgccggtcg agtacctgca ggtgccgtcg     60
ccgtcgatgg gccgcgacat caaggttcag ttccagagcg gtgggaacaa ctcacctgcg    120
gtttatctgc tcgacggcct gcgcgcccaa gacgactaca acggctggga tatcaacacc    180
ccggcgttcg agtggtacta ccagtcggga ctgtcgatag tcatgccggt cggcgggcag    240
tccagcttct acagcgactg gtacagcccg gcctgcggta aggctggctg ccagacttac    300
aagtgggaaa ccttcctgac cagcgagctg ccgcaatggt tgtccgccaa cagggccgtg    360
aagcccaccg gcagcgctgc aatcggcttg tcgatggccg gctcgtcggc aatgatcttg    420
```

```
gccgcctacc accccagca gttcatctac gccggctcgc tgtcggccct gctggacccc    480
tctcagggga tggggcctag cctgatcggc ctcgcgatgg gtgacgccgg cggttacaag    540
gccgcagaca tgtggggtcc ctcgagtgac ccggcatggg agcgcaacga ccctacgcag    600
cagatcccca agctggtcgc aaacaacacc cggctatggg tttattgcgg gaacggcacc    660
ccgaacgagt tgggcggtgc caacataccc gccgagttct tggagaactt cgttcgtagc    720
agcaacctga agttccagga tgcgtacaac gccgcgggcg gcacaacgc cgtgttcaac    780 ttcccgccca acggcacgca cagctgggag tactggggcg ctcagctcaa cgccatgaag    840
ggtgacctgc agagttcgtt aggcgccggc ggtggaggcg cctcaggcgg cgcgcctgga    900
ggtctgaacg acatcttcga ggctcagaaa atcgaatggc acgag                    945
```

<210> SEQ ID NO 78
<211> LENGTH: 296
<212> TYPE: PRT
<213> ORGANISM: Artificial Sequence
<220> FEATURE:
<223> OTHER INFORMATION: Amino acid sequence of MPT-51-protein

<400> SEQUENCE: 78

```
Gly Ala Ser Gly Ser Ala Pro Tyr Glu Asn Leu Met Val Pro Ser Pro
1               5                   10                  15

Ser Met Gly Arg Asp Ile Pro Val Ala Phe Leu Ala Gly Gly Pro His
            20                  25                  30

Ala Val Tyr Leu Leu Asp Ala Phe Asn Ala Gly Pro Asp Val Ser Asn
        35                  40                  45

Trp Val Thr Ala Gly Asn Ala Met Asn Thr Leu Ala Gly Lys Gly Ile
    50                  55                  60

Ser Val Val Ala Pro Ala Gly Gly Ala Tyr Ser Met Tyr Thr Asn Trp
65                  70                  75                  80

Glu Gln Asp Gly Ser Lys Gln Trp Asp Thr Phe Leu Ser Ala Glu Leu
                85                  90                  95

Pro Asp Trp Leu Ala Ala Asn Arg Gly Leu Ala Pro Gly Gly His Ala
            100                 105                 110

Ala Val Gly Ala Ala Gln Gly Gly Tyr Gly Ala Met Ala Leu Ala Ala
        115                 120                 125

Phe His Pro Asp Arg Phe Gly Phe Ala Gly Ser Met Ser Gly Phe Leu
    130                 135                 140

Tyr Pro Ser Asn Thr Thr Thr Asn Gly Ala Ile Ala Ala Gly Met Gln
145                 150                 155                 160

Gln Phe Gly Gly Val Asp Thr Asn Gly Met Trp Gly Ala Pro Gln Leu
                165                 170                 175

Gly Arg Trp Lys Trp His Asp Pro Trp Val His Ala Ser Leu Leu Ala
            180                 185                 190

Gln Asn Asn Thr Arg Val Trp Val Trp Ser Pro Thr Asn Pro Gly Ala
        195                 200                 205

Ser Asp Pro Ala Ala Met Ile Gly Gln Ala Ala Glu Met Gly Asn
    210                 215                 220

Ser Arg Met Phe Tyr Asn Gln Tyr Arg Ser Val Gly Gly His Asn Gly
225                 230                 235                 240

His Phe Asp Phe Pro Ala Ser Gly Asp Asn Gly Trp Gly Ser Trp Ala
                245                 250                 255

Pro Gln Leu Gly Ala Met Ser Gly Asp Ile Val Gly Ala Ile Arg Gly
            260                 265                 270
```

Gly Gly Ala Ser Gly Gly Ala Pro Gly Gly Leu Asn Asp Ile Phe Glu
            275                 280                 285

Ala Gln Lys Ile Glu Trp His Glu
        290                 295

<210> SEQ ID NO 79
<211> LENGTH: 888
<212> TYPE: DNA
<213> ORGANISM: Artificial Sequence
<220> FEATURE:
<223> OTHER INFORMATION: Nucleic acid sequence of MPT-51-DNA

<400> SEQUENCE: 79
ggtgctagcg gcagcgcccc atacgagaac ctgatggtgc cgtcgccctc gatgggccgg     60
gacatcccgg tggccttcct agccggtggg ccgcacgcgg tgtatctgct ggacgccttc    120
aacgccggcc cggatgtcag taactgggtc accgcgggta acgcgatgaa cacgttggcg    180
ggcaagggga tttcggtggt ggcaccggcc ggtggtgcgt acagcatgta caccaactgg    240
gagcaggatg gcagcaagca gtgggacacc ttcttgtccg ctgagctgcc cgactggctg    300
gccgctaacc ggggcttggc ccccggtggc catgcggccg ttggcgccgc tcagggcggt    360
tacggggcga tggcgctggc ggccttccac cccgaccgct tcggcttcgc tggctcgatg    420
tcgggctttt tgtacccgtc gaacaccacc accaacggtg cgatcgcggc gggcatgcag    480
caattcggcg gtgtggacac caacggaatg tggggagcac cacagctggg tcggtggaag    540
tggcacgacc cgtgggtgca tgccagcctg ctggcgcaaa acaacacccg ggtgtgggtg    600
tggagcccga ccaacccggg agccagcgat cccgccgcca tgatcggcca agccgccgag    660
gcgatgggta acagccgcat gttctacaac cagtatcgca gcgtcggcgg cacaacggga    720
cacttcgact tcccagccag cggtgacaac ggctggggct cgtgggcgcc ccagctgggc    780
gctatgtcgg gcgatatcgt cggtgcgatc cgcggtggag gcgcctcagg cggcgcgcct    840
ggaggtctga cgacatcttc gaggctcag aaaatcgaat ggcacgag                 888

<210> SEQ ID NO 80
<211> LENGTH: 94
<212> TYPE: PRT
<213> ORGANISM: Artificial Sequence
<220> FEATURE:
<223> OTHER INFORMATION: Amino acid sequence of MTBL1B42C02-F1-Protein

<400> SEQUENCE: 80

Gly Ala Ser Asp Pro Leu Leu Pro Pro Pro Ile Pro Ala Pro Val
1               5                   10                  15

Ser Ala Pro Ala Thr Val Pro Pro Val Gln Asn Leu Thr Ala Leu Pro
                20                  25                  30

Gly Gly Ser Ser Asn Arg Phe Ser Pro Ala Pro Ala Pro Ala Pro Ile
            35                  40                  45

Ala Ser Pro Ile Pro Val Gly Ala Pro Ser Thr Ala Val Pro Pro
        50                  55                  60

Leu Pro Pro Pro Val Ser Gly Ala Ser Gly Gly Ala Gly Gly Gly Gly
65                  70                  75                  80

Leu Asn Asp Ile Phe Glu Ala Gln Lys Ile Glu Trp His Glu
                85                  90

<210> SEQ ID NO 81
<211> LENGTH: 282
<212> TYPE: DNA
<213> ORGANISM: Artificial Sequence

```
<220> FEATURE:
<223> OTHER INFORMATION: Nucleic acid sequence of MTBLIB42C02-F1-DNA

<400> SEQUENCE: 81
ggagcatctg atccctgct tcctccaccg cctatccctg ccccagtctc ggcgccggca    60
acagtcccgc cgtgcagaa cctcacggcg cttccgggcg ggagcagcaa caggttctca   120
ccggcgccag cacccgcacc gatcgcgtcg ccgattccgg tcggagcacc cgggtccacc   180
gctgtgcccc cgctgccgcc gccagtgagt ggtgcttcag gaggtgctgg cggtggaggt   240
ctgaacgaca tcttcgaggc tcagaaaatc gaatggcacg ag                      282

<210> SEQ ID NO 82
<211> LENGTH: 110
<212> TYPE: PRT
<213> ORGANISM: Artificial Sequence
<220> FEATURE:
<223> OTHER INFORMATION: Amino acid sequence of MTBLIB42C02-F2 Protein

<400> SEQUENCE: 82

Gly Ala Ser Gly Asp Leu Val Gly Pro Gly Cys Ala Glu Tyr Ala Ala
1               5                   10                  15

Ala Asn Pro Thr Gly Pro Ala Ser Val Gln Gly Met Ser Gln Asp Pro
            20                  25                  30

Val Ala Val Ala Ala Ser Asn Asn Pro Glu Leu Thr Thr Leu Thr Ala
        35                  40                  45

Ala Leu Ser Gly Gln Leu Asn Pro Gln Val Asn Leu Val Asp Thr Leu
    50                  55                  60

Asn Ser Gly Gln Tyr Thr Val Phe Ala Pro Thr Asn Ala Ala Phe Ser
65                  70                  75                  80

Lys Leu Pro Ala Ser Ser Gly Ala Ser Gly Gly Ala Gly Gly Gly Gly
                85                  90                  95

Leu Asn Asp Ile Phe Glu Ala Gln Lys Ile Glu Trp His Glu
            100                 105                 110

<210> SEQ ID NO 83
<211> LENGTH: 330
<212> TYPE: DNA
<213> ORGANISM: Artificial Sequence
<220> FEATURE:
<223> OTHER INFORMATION: Nucleic acid sequence of B41C02-F2-DNA

<400> SEQUENCE: 83
ggagcatctg gcgatctggt gggtcctggc tgcgcggaat acgcggcagc caatcccact    60
gggccggcct cggtgcaggg aatgtcgcag gacccggtcg cggtggcggc ctcgaacaat   120
ccggagttga caacgctgac ggctgcactg tcgggccagc tcaatccgca agtaaacctg   180
gtggacaccc tcaacagcgg tcagtacacg gtgttcgcac cgaccaacgc ggcatttagc   240
aagctgccgg catccagtgg tgcttcagga ggtgctggcg gtggaggtct gaacgacatc   300
ttcgaggctc agaaaatcga atggcacgag                                    330

<210> SEQ ID NO 84
<211> LENGTH: 97
<212> TYPE: PRT
<213> ORGANISM: Artificial Sequence
<220> FEATURE:
<223> OTHER INFORMATION: Amino acid sequence of MTBLIB42C02-F4 protein

<400> SEQUENCE: 84

Gly Ala Ser Ala Pro Tyr Glu Asn Leu Met Val Pro Ser Pro Ser Met
```

```
                1               5                   10                  15
            Gly Arg Asp Ile Pro Val Ala Phe Leu Ala Gly Gly Pro His Ala Val
                            20                  25                  30

Tyr Leu Leu Asp Ala Phe Asn Ala Gly Pro Asp Val Ser Asn Trp Val
                        35                  40                  45

Thr Ala Gly Asn Ala Met Asn Thr Leu Ala Gly Lys Gly Ile Ser Val
                    50                  55                  60

Val Ala Pro Ala Gly Gly Ala Tyr Ser Gly Ala Ser Gly Gly Ala Gly
            65                  70                  75                  80

Gly Gly Gly Leu Asn Asp Ile Phe Glu Ala Gln Lys Ile Glu Trp His
                            85                  90                  95

Glu

<210> SEQ ID NO 85
            <211> LENGTH: 291
            <212> TYPE: DNA
            <213> ORGANISM: Artificial Sequence
            <220> FEATURE:
            <223> OTHER INFORMATION: Nucleic acid sequence of MTBLIB42C02-F4-DNA

<400> SEQUENCE: 85
ggagcatctg cccccttacga gaacctgatg gtgccgtcgc cctcgatggg ccgggacatc      60
ccggtggcct tcctagccgg tgggccgcac gcggtgtatc tgctggacgc cttcaacgcc     120
ggcccggatg tcagtaactg ggtcaccgcg ggtaacgcga tgaacacgtt ggcgggcaag     180
gggatttcgg tggtggcacc ggccggtggt gcgtacagtg gtgcttcagg aggtgctggc     240
ggtggaggtc tgaacgacat cttcgaggct cagaaaatcg aatggcacga g               291

<210> SEQ ID NO 86
            <211> LENGTH: 88
            <212> TYPE: PRT
            <213> ORGANISM: Artificial Sequence
            <220> FEATURE:
            <223> OTHER INFORMATION: Amino acid sequence of MTBLIB42C02-F6-Protein

<400> SEQUENCE: 86

Gly Ala Ser Met Thr Gln Ser Gln Thr Val Thr Val Asp Gln Gln Glu
            1               5                   10                  15

Ile Leu Asn Arg Ala Asn Glu Val Glu Ala Pro Met Ala Asp Pro Pro
                            20                  25                  30

Thr Asp Val Pro Ile Thr Pro Cys Glu Leu Thr Ala Ala Lys Asn Ala
                        35                  40                  45

Ala Gln Gln Leu Val Leu Ser Ala Asp Asn Met Arg Glu Tyr Leu Ser
                    50                  55                  60

Gly Ala Ser Gly Gly Ala Gly Gly Gly Leu Asn Asp Ile Phe Glu
            65                  70                  75                  80

Ala Gln Lys Ile Glu Trp His Glu
                            85

<210> SEQ ID NO 87
            <211> LENGTH: 264
            <212> TYPE: DNA
            <213> ORGANISM: Artificial Sequence
            <220> FEATURE:
            <223> OTHER INFORMATION: Nucleic acid sequence of MTBLIB42C02-F6-DNA

<400> SEQUENCE: 87
ggagcatcta tgacgcaatc gcagaccgtg acggtggatc agcaagagat tttgaacagg      60
```

```
gccaacgagg tggaggcccc gatggcggac ccaccgactg atgtccccat cacaccgtgc    120
gaactcacgg cggctaaaaa cgccgcccaa cagctggtat tgtccgccga caacatgcgg    180
gaatacctga gtggtgcttc aggaggtgct ggcggtggag gtctgaacga catcttcgag    240
gctcagaaaa tcgaatggca cgag                                          264
```

<210> SEQ ID NO 88
<211> LENGTH: 79
<212> TYPE: PRT
<213> ORGANISM: Artificial Sequence
<220> FEATURE:
<223> OTHER INFORMATION: Amino acid sequence of MTBLIB42C02-F7 protein

<400> SEQUENCE: 88

```
Gly Ala Ser Met Pro Leu Thr Pro Ala Asp Val His Asn Val Ala Phe
 1               5                  10                  15

Ser Lys Pro Pro Ile Gly Lys Arg Gly Tyr Asn Glu Asp Glu Val Asp
                20                  25                  30

Ala Phe Leu Asp Leu Val Glu Asn Glu Pro Thr Arg Leu Ile Glu Glu
            35                  40                  45

Asn Ser Asp Leu Arg Gln Ser Gly Ala Ser Gly Gly Ala Gly Gly Gly
        50                  55                  60

Gly Leu Asn Asp Ile Phe Glu Ala Gln Lys Ile Glu Trp His Glu
    65                  70                  75
```

<210> SEQ ID NO 89
<211> LENGTH: 237
<212> TYPE: DNA
<213> ORGANISM: Artificial Sequence
<220> FEATURE:
<223> OTHER INFORMATION: Nucliec acid sequence of MTBLIB42C02-F7-DNA

<400> SEQUENCE: 89

```
ggagcatcta tgccgcttac acctgccgac gtccacaatg tggcgttcag taagccgcct     60
atcggcaaac gtgggtacaa cgaagatgag gtcgacgcct tcctcgacct ggtggaaaac    120
gagccgaccc gcctgatcga agagaactcc gatctgcgtc agagtggtgc ttcaggaggt    180
gctggcggtg gaggtctgaa cgacatcttc gaggctcaga aaatcgaatg gcacgag       237
```

<210> SEQ ID NO 90
<211> LENGTH: 95
<212> TYPE: PRT
<213> ORGANISM: Artificial Sequence
<220> FEATURE:
<223> OTHER INFORMATION: Amino acid sequence of MTBLIB42C02-F8 protein

<400> SEQUENCE: 90

```
Gly Ala Ser Gln Leu Val Ser Ala Gln Gly Ser Gln Gly Met Gly Gly
 1               5                  10                  15

Pro Val Gly Met Gly Gly Met His Pro Ser Ser Gly Ala Ser Lys Gly
                20                  25                  30

Thr Thr Thr Lys Lys Tyr Ser Glu Gly Ala Ala Ala Gly Thr Glu Asp
            35                  40                  45

Ala Glu Arg Ala Pro Val Glu Ala Asp Ala Gly Gly Gly Gln Lys Val
        50                  55                  60

Leu Val Arg Asn Val Val Ser Gly Ala Ser Gly Gly Ala Gly Gly Gly
    65                  70                  75                  80

Gly Leu Asn Asp Ile Phe Glu Ala Gln Lys Ile Glu Trp His Glu
                85                  90                  95
```

<210> SEQ ID NO 91
<211> LENGTH: 285
<212> TYPE: DNA
<213> ORGANISM: Artificial Sequence
<220> FEATURE:
<223> OTHER INFORMATION: Nucleic acid sequence of MTBLIB42C02-F8-DNA

<400> SEQUENCE: 91

```
ggagcatctc agctggtctc cgcgcagggt tcccaaggta tgggcggacc cgtaggcatg      60
ggcggcatgc acccctcttc gggggcgtcg aaagggacga cgacgaagaa gtactcggaa     120
ggcgcggcgg cgggcactga agacgccgag cgcgcgccag tcgaagctga cgcgggcggt     180
gggcaaaagg tgctggtacg aaacgtggtc agtggtgctt caggaggtgc tggcggtgga     240
ggtctgaacg acatcttcga ggctcagaaa atcgaatggc acgag                     285
```

<210> SEQ ID NO 92
<211> LENGTH: 91
<212> TYPE: PRT
<213> ORGANISM: Artificial Sequence
<220> FEATURE:
<223> OTHER INFORMATION: Amino acid sequence of MTBLIB42C02-F10 protein

<400> SEQUENCE: 92

```
Gly Ala Ser Val Ile Ala Gly Gln Ala Ser Pro Ser Arg Ile Asp Gly
1               5                   10                  15

Thr His Gln Thr Leu Gln Gly Ala Asp Leu Thr Val Ile Gly Ala Arg
            20                  25                  30

Asp Asp Leu Met Val Asn Asn Ala Gly Leu Val Cys Gly Gly Val His
        35                  40                  45

Thr Ala Asn Ala Thr Val Tyr Met Ile Asp Thr Val Leu Met Pro Pro
    50                  55                  60

Ala Gln Ser Gly Ala Ser Gly Gly Ala Gly Gly Gly Gly Leu Asn Asp
65                  70                  75                  80

Ile Phe Glu Ala Gln Lys Ile Glu Trp His Glu
            85                  90
```

<210> SEQ ID NO 93
<211> LENGTH: 273
<212> TYPE: DNA
<213> ORGANISM: Artificial Sequence
<220> FEATURE:
<223> OTHER INFORMATION: Nucleic acid sequence of MTBLIB42C02-F10-DNA

<400> SEQUENCE: 93

```
ggagcatctg tgatagccgg ccaggcgagt ccgagcagga tcgacggcac ccatcagacc      60
ctgcaaggtg ccgacctgac ggtgataggc gcccgcgacg acctcatggt caacaacgcc     120
ggtttggtat gtggcggagt tcacaccgcc aacgcgacgg tgtacatgat cgatacggtg     180
ctgatgcccc ccgcgcagag tggtgcttca ggaggtgctg gcggtggagg tctgaacgac     240
atcttcgagg ctcagaaaat cgaatggcac gag                                 273
```

<210> SEQ ID NO 94
<211> LENGTH: 114
<212> TYPE: PRT
<213> ORGANISM: Artificial Sequence
<220> FEATURE:
<223> OTHER INFORMATION: Amino acid sequence of MTBLIB42C02-F11 protein

<400> SEQUENCE: 94

```
Gly Ala Ser Asp Pro Leu Leu Pro Pro Pro Ile Pro Ala Pro Val
```

```
                1               5                    10                  15
Ser Ala Pro Ala Thr Pro Pro Val Gln Asn Leu Thr Ala Leu Pro
                20                   25                  30
Gly Gly Ser Ser Asn Arg Phe Ser Pro Thr Pro Ala Pro Ala Pro Ile
                35                   40                  45
Ala Ser Pro Ile Pro Val Gly Ala Pro Gly Ser Thr Ala Val Pro Pro
        50                   55                  60
Leu Pro Pro Val Thr Pro Ala Ile Ser Gly Thr Leu Arg Asp His
65                   70                  75                  80
Leu Arg Glu Lys Gly Val Lys Leu Glu Ser Gly Ala Ser Gly Ala
                    85                  90                  95
Gly Gly Gly Gly Leu Asn Asp Ile Phe Glu Ala Gln Lys Ile Glu Trp
            100                 105                 110
His Glu
```

<210> SEQ ID NO 95
<211> LENGTH: 342
<212> TYPE: DNA
<213> ORGANISM: Artificial Sequence
<220> FEATURE:
<223> OTHER INFORMATION: Nucleic acid sequence of MTBLIB42C02-F11-DNA

<400> SEQUENCE: 95

```
ggagcatctg atcccctgct tcctccaccg cctatccctg ccccagtctc ggcgccggca    60
acagtcccgc ccgtgcagaa cctcacggcg cttccgggcg ggagcagcaa caggttctca   120
ccgacgccag cacccgcacc gatcgcgtcg ccgattccgg tcggagcacc cgggtccacc   180
gctgtgcccc cgctgccgcc gccagtgact cccgcgatca gcggcacact tcgggaccac   240
ctccgggaga agggcgtcaa gctggagagt ggtgcttcag gaggtgctgg cggtggaggt   300
ctgaacgaca tcttcgaggc tcagaaaatc gaatggcacg ag                      342
```

<210> SEQ ID NO 96
<211> LENGTH: 75
<212> TYPE: PRT
<213> ORGANISM: Artificial Sequence
<220> FEATURE:
<223> OTHER INFORMATION: Amino acid sequence of MTBLIB42C02-F12 protein

<400> SEQUENCE: 96

```
                1               5                    10                  15
Gly Ala Ser Pro Asn Gly Thr Tyr Val Asn Arg Glu Pro Val Asp Ser
                20                  25                  30
Ala Val Leu Ala Asn Gly Asp Glu Val Gln Ile Gly Gln Phe Arg Leu
                35                  40                  45
Val Phe Leu Thr Gly Pro Lys Gln Gly Glu Asp Asp Gly Ser Thr Gly
        50                  55                  60
Gly Pro Ser Gly Ala Ser Gly Gly Ala Gly Gly Gly Leu Asn Asp
65                  70                  75
Ile Phe Glu Ala Gln Lys Ile Glu Trp His Glu
```

<210> SEQ ID NO 97
<211> LENGTH: 225
<212> TYPE: DNA
<213> ORGANISM: Artificial Sequence
<220> FEATURE:
<223> OTHER INFORMATION: Nucleic acid sequence of MTBLIB42C02-F12 DNA

<400> SEQUENCE: 97

```
ggagcatctc caacggcac ctacgtcaac cgcgagcccg tggattcggc ggtgctggcg    60
aacggcgacg aggtccagat cggccagttc cggttggtgt tcttgaccgg acccaagcaa   120
ggcgaggatg acgggagtac gggaggacca agtggtgctt caggaggtgc tggcggtgga   180
ggtctgaacg acatcttcga ggctcagaaa atcgaatggc acgag                   225
```

<210> SEQ ID NO 98
<211> LENGTH: 15
<212> TYPE: PRT
<213> ORGANISM: Artificial Sequence
<220> FEATURE:
<223> OTHER INFORMATION: Amino acid sequence of BAP tag

<400> SEQUENCE: 98

```
Gly Leu Asn Asp Ile Phe Glu Ala Gln Lys Ile Glu Trp His Glu
1               5                  10                  15
```

<210> SEQ ID NO 99
<211> LENGTH: 24
<212> TYPE: DNA
<213> ORGANISM: Artificial Sequence
<220> FEATURE:
<223> OTHER INFORMATION: Primer sequence of 5' Primers M13R

<400> SEQUENCE: 99

```
agcggataac aatttcacac agga                                           24
```

<210> SEQ ID NO 100
<211> LENGTH: 23
<212> TYPE: DNA
<213> ORGANISM: Artificial Sequence
<220> FEATURE:
<223> OTHER INFORMATION: Primer sequence of 3' Primer U251CO

<400> SEQUENCE: 100

```
ggttttatca tctttccaca cgt                                            23
```

<210> SEQ ID NO 101
<211> LENGTH: 1209
<212> TYPE: DNA
<213> ORGANISM: Artificial Sequence
<220> FEATURE:
<223> OTHER INFORMATION: Nucleiac acid sequence of E. coli codon
      optimized gIII

<400> SEQUENCE: 101

```
gttgaaagct gtctcgcgaa accgcataca gaaaattcat tcaccaacgt gtggaaagat    60
gataaaaccc tggatcgcta tgccaattat gaaggttgtc tgtggaatgc aacaggtgtt   120
gttgtttgca caggtgatga aacccagtgt tatggcacct gggttccgat tggtctggca   180
atcccggaaa atgaaggtgg tggtagcgaa ggcggtggtt cagaaggcgg aggcagcgaa   240
ggtggcggaa ccaaaccgcc tgaatatggt gataccccga ttccgggtta tacctatatt   300
aacccgctgg atggtacata tccgcctggc accgaacaga tccggcaaa tccgaatccg   360 agcctggaag aaagccagcc gctgaatacc tttatgtttc agaataatcg ttttcgcaat   420
cgtcagggtg ccctgaccgt ttataccggc accgttaccc agggcaccga tcctgttaaa   480
acctattatc agtataccccc tgttagcagc aaagcaatgt atgatgccta ttggaatggt   540
aaatttcgtg attgtgcatt tcacagcggc tttaatgaag atccgtttgt ttgtgaatat   600
cagggtcaga gcagcgatct gccgcagcct ccagttaatg ccggtggtgg cagtggtggc   660
ggttctgggg gtggtagtga gggtgggga agcgagggtg gaggctcaga gggaggcgga   720
```

```
tcagagggcg gtggaagtgg cggaggtagt ggcagcggtg attttgatta tgagaaaatg    780
gccaatgcca acaaggtgc aatgaccgaa atgcagatg aaatgccct gcaaagtgat       840 gcaaaaggta aactggatag cgttgcaacc gattatggtg cagccattga tggttttatt    900
ggtgatgtta gcggtctggc taatggtaat ggtgccacag gcgattttgc aggtagcaat    960
agccagatgg cacaggtagg tgatggcgat aatagtccgc tgatgaataa ctttcgtcag   1020
tatctgccga gtctgcctca gagcgttgaa tgtcgtcctt tgtttttgg tgcaggtaaa    1080 ccgtatgaat ttagcatcga ctgcgataaa atcaacctgt tcgtggtgt ttttgccttt    1140 ctgctgtatg ttgccacatt catgtatgtg tttagcacct tgcaaacat cctgcgtaat    1200 aaagaaagc                                                           1209
```

<210> SEQ ID NO 102
<211> LENGTH: 403
<212> TYPE: PRT
<213> ORGANISM: Artificial Sequence
<220> FEATURE:
<223> OTHER INFORMATION: Amino acid sequence of codon optiized E. coli gIII

<400> SEQUENCE: 102

```
Val Glu Ser Cys Leu Ala Lys Pro His Thr Glu Asn Ser Phe Thr Asn
1               5                   10                  15

Val Trp Lys Asp Asp Lys Thr Leu Asp Arg Tyr Ala Asn Tyr Glu Gly
            20                  25                  30

Cys Leu Trp Asn Ala Thr Gly Val Val Cys Thr Gly Asp Glu Thr
        35                  40                  45

Gln Cys Tyr Gly Thr Trp Val Pro Ile Gly Leu Ala Ile Pro Glu Asn
    50                  55                  60

Glu Gly Gly Gly Ser Glu Gly Gly Ser Glu Gly Gly Ser Glu
65                  70                  75                  80

Gly Gly Gly Thr Lys Pro Pro Glu Tyr Gly Asp Thr Pro Ile Pro Gly
                85                  90                  95

Tyr Thr Tyr Ile Asn Pro Leu Asp Gly Thr Tyr Pro Pro Gly Thr Glu
            100                 105                 110

Gln Asn Pro Ala Asn Pro Asn Pro Ser Leu Glu Glu Ser Gln Pro Leu
        115                 120                 125

Asn Thr Phe Met Phe Gln Asn Asn Arg Phe Arg Asn Arg Gln Gly Ala
    130                 135                 140

Leu Thr Val Tyr Thr Gly Thr Val Thr Gln Gly Thr Asp Pro Val Lys
145                 150                 155                 160

Thr Tyr Tyr Gln Tyr Thr Pro Val Ser Ser Lys Ala Met Tyr Asp Ala
                165                 170                 175

Tyr Trp Asn Gly Lys Phe Arg Asp Cys Ala Phe His Ser Gly Phe Asn
            180                 185                 190

Glu Asp Pro Phe Val Cys Glu Tyr Gln Gly Gln Ser Ser Asp Leu Pro
        195                 200                 205

Gln Pro Pro Val Asn Ala Gly Gly Gly Ser Gly Gly Gly Ser Gly Gly
    210                 215                 220

Gly Ser Glu Gly Gly Gly Ser Glu Gly Gly Ser Glu Gly Gly
225                 230                 235                 240

Ser Glu Gly Gly Gly Ser Gly Gly Gly Ser Gly Ser Gly Asp Phe Asp
                245                 250                 255

Tyr Glu Lys Met Ala Asn Ala Asn Lys Gly Ala Met Thr Glu Asn Ala
```

```
                    260                 265                 270
Asp Glu Asn Ala Leu Gln Ser Asp Ala Lys Gly Lys Leu Asp Ser Val
                275                 280                 285

Ala Thr Asp Tyr Gly Ala Ala Ile Asp Gly Phe Ile Gly Asp Val Ser
                290                 295                 300

Gly Leu Ala Asn Gly Asn Gly Ala Thr Gly Asp Phe Ala Gly Ser Asn
305                 310                 315                 320

Ser Gln Met Ala Gln Val Gly Asp Gly Asp Asn Ser Pro Leu Met Asn
                325                 330                 335

Asn Phe Arg Gln Tyr Leu Pro Ser Leu Pro Gln Ser Val Glu Cys Arg
                340                 345                 350

Pro Phe Val Phe Gly Ala Gly Lys Pro Tyr Glu Phe Ser Ile Asp Cys
                355                 360                 365

Asp Lys Ile Asn Leu Phe Arg Gly Val Phe Ala Phe Leu Leu Tyr Val
                370                 375                 380

Ala Thr Phe Met Tyr Val Phe Ser Thr Phe Ala Asn Ile Leu Arg Asn
385                 390                 395                 400

Lys Glu Ser

<210> SEQ ID NO 103
<211> LENGTH: 58
<212> TYPE: DNA
<213> ORGANISM: Artificial Sequence
<220> FEATURE:
<223> OTHER INFORMATION: Primer sequence - HuPelBNextThio-52

<400> SEQUENCE: 103
tcgtcggcag cgtcagatgt gtataagaga caggctactg atgacagctc agccagcg      58

<210> SEQ ID NO 104
<211> LENGTH: 59
<212> TYPE: DNA
<213> ORGANISM: Artificial Sequence
<220> FEATURE:
<223> OTHER INFORMATION: Primer sequence of HuG4SNextThio-31

<400> SEQUENCE: 104
gtctcgtggg ctcggagatg tgtataagag acaggcctcc agagccaccg ccaccggat     59

<210> SEQ ID NO 105
<211> LENGTH: 57
<212> TYPE: DNA
<213> ORGANISM: Artificial Sequence
<220> FEATURE:
<223> OTHER INFORMATION: Primer sequence HuG4SNextThio-51

<400> SEQUENCE: 105
tcgtcggcag cgtcagatgt gtataagaga caggcggtgg ctctggaggc ggtggaa       57

<210> SEQ ID NO 106
<211> LENGTH: 58
<212> TYPE: DNA
<213> ORGANISM: Artificial Sequence
<220> FEATURE:
<223> OTHER INFORMATION: Primer sequence - HuCH1NextThio-31

<400> SEQUENCE: 106
gtctcgtggg ctcggagatg tgtataagag acagctttgt actcgctgag gagacggt      58

<210> SEQ ID NO 107
<211> LENGTH: 58
```

```
<212> TYPE: DNA
<213> ORGANISM: Artificial Sequence
<220> FEATURE:
<223> OTHER INFORMATION: Primer sequence P5N502NextE-51

<400> SEQUENCE: 107
aatgatacgg cgaccaccga gatctacacc tctctattcg tcggcagcgt cagatgtg      58

<210> SEQ ID NO 108
<211> LENGTH: 55
<212> TYPE: DNA
<213> ORGANISM: Artificial Sequence
<220> FEATURE:
<223> OTHER INFORMATION: Primer sequence - P7N702NextE-31

<400> SEQUENCE: 108
caagcagaag acggcatacg agatctagta cggtctcgtg ggctcggaga tgtgt         55

<210> SEQ ID NO 109
<211> LENGTH: 58
<212> TYPE: DNA
<213> ORGANISM: Artificial Sequence
<220> FEATURE:
<223> OTHER INFORMATION: Primer sequence P5N503NextEThio-51

<400> SEQUENCE: 109
aatgatacgg cgaccaccga gatctacact atcctcttcg tcggcagcgt cagatgtg      58

<210> SEQ ID NO 110
<211> LENGTH: 55
<212> TYPE: DNA
<213> ORGANISM: Artificial Sequence
<220> FEATURE:
<223> OTHER INFORMATION: Primer sequence P7N703NextEThio-31

<400> SEQUENCE: 110
caagcagaag acggcatacg agatttctgc ctgtctcgtg ggctcggaga tgtgt         55
```

ANTIBODY FRAGMENT LIBRARY, AND USES THEREOF

CROSS-REFERENCE TO RELATED APPLICATIONS

This application is the 35 U.S.C. § 371 national stage of PCT application having serial number PCT/IN2018/050802, filed on Nov. 30, 2018.

FIELD OF INVENTION

The present disclosure broadly relates to the field of antibody cloning technology and particularly discloses construction of antibody fragment library, and uses thereof.

BACKGROUND OF THE INVENTION

The conventional hybridoma technology introduced more than thirty years ago, is still widely used for the production of monoclonal antibodies against a protein of interest (POI). However, this technology, apart from being time and labor intensive, suffers from other limitations including inability to generate antibodies against proteins conserved across species (as they tend to be recognized as self) and hence, may not be suitable for generating antibodies against every antigen in a high-throughput format.

Over past 2-3 decades, serious efforts have led to the development of cutting-edge antibody cloning technologies and powerful surface display technologies including phage display, which have allowed the generation of large and diverse human antibody libraries in vitro and have emerged as an alternative to the hybridoma technology. The structural organization and the sequence of rearranged human antibody variable gene families are available, and strategies have been developed for PCR-based rescue of rearranged variable antibody genes using set of degenerate primers based on the relatively conserved framework regions (de Haard et al., 1999; Lefranc et al., 1999; Schwimmer et al., 2013). This, combined with availability of phage-based display systems have led to the recreation of the entire human antibody repertoire in a single tube, where pools of billions of unique antibodies can be used to select for antibodies against POI and the sequence of corresponding antibody can be decoded by sequencing the DNA encapsulated in the phage.

Marks et al., 1991 (Marks, J. D., H. R. Hoogenboom, T. P. Bonnert, J. McCafferty, A. D. Griffiths and G. Winter (1991). "By-passing immunization. Human antibodies from V-gene libraries displayed on phage." J Mol Biol 222(3): 581-597) reported the construction of a combinatorial naïve human antibody library in scFv format, comprising of $2.9 \times 10^7$ clones and $1.6 \times 10^8$ clones, encoding genes amplified from the IgM and IgG mRNA, respectively, isolated from PBMCs from 2 donors. The variable antibody genes were amplified from cDNA using a set of degenerate primers and were linked in $V_H$-Linker-$V_L$ format using a three-fragment splice PCR, followed by addition of restriction enzyme sites.

Sheets et al., 1998 (Sheets, M. D., P. Amersdorfer, R. Finnern, P. Sargent, E. Lindquist, R. Schier, G. Hemingsen, C. Wong, J. C. Gerhart and J. D. Marks (1998). "Efficient construction of a large nonimmune phage antibody library: the production of high-affinity human single-chain antibodies to protein antigens." Proc Natl Acad Sci USA 95(11): 6157-62) reported the construction of a combinatorial naïve human antibody library in scFv format comprising of $6.7 \times 10^9$ clones, encoding $V_H$ genes amplified from the IgM RNA isolated from PBMCs from 2 donors and spleen from 3 donors and $V_L$ genes isolated from the pre-existing scFv library of (Marks et al., 1991). The variable heavy antibody genes were amplified from cDNA using a set of degenerate primers and were cloned individually into pCITE3A vector to yield a pCITE-$V_H$ library of $2.3 \times 10^8$ $V_H$ genes. Following this, the $V_H$ genes were PCR amplified from pCITE-$V_H$ library and the $V_L$ genes were amplified from the plasmid DNA of previously described naïve human scFv library of Marks et al. Finally, the amplified genes were linked in $V_H$-Linker-$V_L$ format using a two-fragment splice PCR. The assembled scFv was digested using NcoI and NotI restriction enzymes and ligated into pHEN1 vector. Analysis of 36 randomly selected clones revealed 36 unique sequences. The library yielded specific binders against all the 14 targets employed in the study. Using ELISA, 9-95% of clones were found to be positive against different targets after 3-4 rounds of selection.

de Haard et al., 1999 (de Haard, H. J., N. van Neer, A. Reurs, S. E. Hufton, R. C. Roovers, P. Henderikx, A. P. de Bruine, J. W. Arends and H. R. Hoogenboom (1999). "A large non-immunized human Fab fragment phage library that permits rapid isolation and kinetic analysis of high affinity antibodies." J Biol Chem 274(26): 18218-18230) reported the construction of a combinatorial naïve human antibody library in Fab format comprising of $4.3 \times 10^{10}$ clones, encoding antibody genes amplified from the RNA isolated from PBMCs of 4 donors and spleen from 1 donor. The variable heavy and light antibody genes were separately amplified from cDNA derived from PBMCs or spleen using a set of degenerate primers. The $V_L$ genes were PCR amplified with the corresponding CL and the $V_L$-$C_L$ cassettes were cloned into pCES1 vector using ApaLI and AscI restriction enzymes. The $V_H$ genes were PCR amplified and cloned separately into pUC119-CES1 vector using SfiI-BstEII restriction enzymes. Finally, the $V_H$ genes were digested from pUC119-CES1 vector and cloned into pCES1 vector containing the light chain genes to obtain Fab libraries of $1.95 \times 10^{10}$ (PBMCs) and $2.35 \times 10^{10}$ (Spleen) clones amounting to a total diversity of $4.3 \times 10^{10}$ clones. Overall, only 86% of the clones were found to encode full-length Fab insert. The library yielded specific binders against all the 7 targets employed in the study. Using ELISA, 33-88% of clones were found to be positive against different targets after third round of selection.

Sblattero and Bradbury 2000 (Sblattero, D. and A. Bradbury (2000). "Exploiting recombination in single bacteria to make large phage antibody libraries." Nat Biotechnol 18(1): 75-80.) reported the construction of a combinatorial human antibody library in scFv format comprising of $3 \times 10^{10}$ clones, encoding antibody genes amplified from the RNA isolated from PBMCs of 40 donors. The variable heavy and light antibody genes were separately amplified from cDNA derived from PBMCs using a set of degenerate primers. Finally, the $V_H$ and $V_L$ genes were assembled using PCR to a primary scFv library of $7 \times 10^7$ clones in pDAN5 vector. In this, the $V_L$ and $V_H$ genes were separated by two non-homologous lox sites oriented in a manner to allow recombination between different $V_L$ and $V_H$ sequences for increased diversity. Therefore, using lox-cre recombination, a secondary library of $3 \times 10^{10}$ clones was generated. About 94% clones (90/96) in the secondary library were found to encode full-length scFv insert. The library was reported to yield specific binders against all the 15 targets employed in the study.

Rojas et al., 2002 (Rojas, G., J. C. Almagro, B. Acevedo and J. V. Gavilondo (2002). "Phage antibody fragments library combining a single human light chain variable region with immune mouse heavy chain variable regions." J Biotechnol 94(3): 287-98) reported the construction of a combinatorial naïve human antibody library in scFv format comprising of $5\times10^8$ clones, encoding antibody genes amplified from the RNA isolated from PBMCs of 17 donors, tonsils from 5 donors, bone marrow from 9 donors, and spleen from 1 donor. The variable heavy and light antibody genes were separately amplified from cDNA using a set of degenerate primers using PCR. The $V_L$ and $V_H$ genes were cloned separately into pHG-1m vector using SalI-NotI and ApaLI-SfiI restriction enzymes, respectively.

Loset et al., 2005 (Loset, G. A., I. Lobersli, A. Kavlie, J. E. Stacy, T. Borgen, L. Kausmally, E. Hvattum, B. Simonsen, M. B. Hovda and O. H. Brekke (2005). "Construction, evaluation and refinement of a large human antibody phage library based on the IgD and IgM variable gene repertoire." J Immunol Methods 299(1-2): 47-62) reported the construction of a combinatorial naïve human antibody library in scFv format comprising of $6.4\times10^9$ clones, encoding antibody genes amplified from the IgM and IgD RNA isolated from PBMCs of 6 donors. The variable heavy and light antibody genes were separately amplified from cDNA using a set of degenerate primers using PCR. The $V_L$ genes were cloned separately into pHOG21 vector using MluI-NotI restriction enzymes.

Schofield et al., 2007 (Schofield, D. J., A. R. Pope, V. Clementel, J. Buckell, S. Chapple, K. F. Clarke, J. S. Conquer, A. M. Crofts, S. R. Crowther, M. R. Dyson, G. Flack, G. J. Griffin, Y. Hooks, W. J. Howat, A. Kolb-Kokocinski, S. Kunze, C. D. Martin, G. L. Maslen, J. N. Mitchell, M. O'Sullivan, R. L. Perera, W. Roake, S. P. Shadbolt, K. J. Vincent, A. Warford, W. E. Wilson, J. Xie, J. L. Young and J. McCafferty (2007). "Application of phage display to high throughput antibody generation and characterization." Genome Biol 8(11): R254) reported the construction of a combinatorial naïve human antibody library in scFv format comprising of $1.1\times10^{10}$ clones, encoding antibody genes amplified from the RNA isolated from PBMCs of 42 donors, and Tonsils from 1 donor. The variable heavy and light antibody genes were separately amplified from cDNA using a set of degenerate primers using PCR. The $V_L$ genes were cloned separately into pSANG vector using NheI-NotI restriction enzymes followed by cloning of $V_H$ gene repertoire in $V_L$ containing vector using NcoI-XhoI restriction enzymes to obtain 16 sub-libraries amounting to a total of $1.3\times10^{10}$ clones. Overall, 73-100% clones in different sub-libraries were found to encode full-length scFv insert leading to an approximate scFv library size of $1.1\times10^{10}$ clones. The library was evaluated against 404 targets and was found to yield antibodies against 292 targets (72%). In this, the analysis of 38,164 antibodies against 404 targets revealed that only 9,384 antibodies (24.6%) were positive in the primary screen after two rounds of selection.

Pansri et al., 2009 (Pansri, P., N. Jaruseranee, K. Rangnoi, P. Kristensen and M. Yamabhai (2009). "A compact phage display human scFv library for selection of antibodies to a wide variety of antigens." BMC Biotechnol 9: 6) reported the construction of a combinatorial naïve human antibody library in scFv format comprising of $1.5\times10^8$ clones, encoding genes amplified from RNA isolated from PBMCs of 140 non-immunized donors. The variable antibody genes were amplified from cDNA using a set of degenerate primers and linked in $V_H$-Linker-$V_L$ format using a two-fragment splice PCR. The assembled scFv was digested using SfiI and NotI restriction enzymes and ligated to pMOD1 vector. The library yielded specific binders against 7/8 targets employed in this study. Using ELISA, 1-21% of clones were found to be positive against different targets after 1 round of selection.

Lloyd et al., 2009 (Lloyd, C., D. Lowe, B. Edwards, F. Welsh, T. Dilks, C. Hardman and T. Vaughan (2009). "Modelling the human immune response: performance of a 1011 human antibody repertoire against a broad panel of therapeutically relevant antigens." Protein Eng Des Sel 22(3): 159-68) reported the construction of a combinatorial naïve human antibody libraries in scFv format comprising of $8.5\times10^{10}$ clones encoding genes amplified from RNA isolated from spleen of 20 donors and $3.3\times10^{10}$ clones encoding fetal liver of 97 donors. The variable antibody genes were amplified from cDNA using a set of degenerate primers and were cloned into modified pCANTAB6 vector using XhoI and ApaLI restriction enzymes. This library in combination with previously described library from the same group (Vaughan et al., 1996) amounted to approximately $1.2\times10^{11}$ clones. The library yielded specific binders against all the 28 targets employed in the study.

Glanville et al., 2009 (Glanville, J., W. Zhai, J. Berka, D. Telman, G. Huerta, G. R. Mehta, I. Ni, L. Mei, P. D. Sundar, G. M. Day, D. Cox, A. Rajpal and J. Pons (2009). "Precise determination of the diversity of a combinatorial antibody library gives insight into the human immunoglobulin repertoire." Proc Natl Acad Sci USA 106(48): 20216-21) reported the construction of a combinatorial naïve human antibody libraries in scFv format comprising of $3.1\times10^{10}$ clones, encoding genes amplified from RNA isolated from PBMCs of 637 donors and spleen of 17 donors. The variable antibody genes were amplified from the cDNA using a set of degenerate primers and assembled in $V_H$-L-$V_L$ format, digested with SfiI restriction enzyme and ligated to a phage display vector. The library yielded specific binders against all the 16 targets employed in the study after 3-4 rounds of panning.

Hust et al., 2011 (Hust, M., T. Meyer, B. Voedisch, T. Rulker, H. Thie, A. El-Ghezal, M. I. Kirsch, M. Schutte, S. Helmsing, D. Meier, T. Schirrmann and S. Dubel (2011). "A human scFv antibody generation pipeline for proteome research." J Biotechnol 152(4): 159-70) reported the construction of three combinatorial naïve human antibody libraries in scFv format comprising of $2.2\times10^9$ (HAL4), $2.8\times10^9$ (HAL7), and $2.4\times10^9$ (HAL8) clones, encoding antibody genes amplified from the RNA isolated from PBMCs of 44 donors. The variable heavy and light antibody genes were separately amplified from cDNA using a set of degenerate primers using PCR. The $V_L$ genes were cloned separately into pHAL14 vector using NheI-NotI restriction enzymes to obtain libraries amounting to a total of $2-8\times10^8$ $V_L$ clones followed by cloning of $V_H$ gene repertoire in $V_L$ containing vector using NcoI-HindIII restriction enzymes. Overall, 86-89% clones in different libraries were found to encode full-length scFv insert. The library was evaluated against 91 targets and was found to yield antibodies against all of them after 2-3 rounds of selection.

Schwimmer et al., 2013 (Schwimmer, L. J., B. Huang, H. Giang, R. L. Cotter, D. S. Chemla-Vogel, F. V. Dy, E. M. Tam, F. Zhang, P. Toy, D. J. Bohmann, S. R. Watson, J. W. Beaber, N. Reddy, H. F. Kuan, D. H. Bedinger and I. J. Rondon (2013). "Discovery of diverse and functional antibodies from large human repertoire antibody libraries." J Immunol Methods 391(1-2): 60-71) reported the construction of two combinatorial naïve human antibody libraries in scFv and Fab format comprising of $3.6\times10^{11}$ and $2.5\times10^{11}$ clones, respectively. The antibody genes encoded in scFv library were derived from the RNA isolated from PBMCs of 20 donors, bone marrow samples of 8 donors, lymph nodes of 1 donor, and spleen of 1 donor. The antibody genes encoded in Fab library were derived from the RNA isolated from PBMCs of 15 donors, and bone marrow samples of 15 donors. For the construction of scFv library, the variable heavy and light antibody genes were amplified from cDNA using a set of degenerate primers using PCR and linked in $V_H$-Linker-$V_L$ format using a two-fragment splice PCR. The assembled scFv genes were cloned in pXHMV-scFv vector using SfiI restriction enzyme. For the construction of Fab library, the variable heavy and light antibody genes were amplified from cDNA using a set of degenerate primers to amplify the $V_H$, Vλ and Vκ genes from IgM, IgG, IgD, IgA and IgE RNA. In first step, the $V_L$ were cloned into pXHMV-US2-L-Fab and pXHMV-US2-K-Fab vectors using SfiI-AvrII for $V_\lambda$ and SfiI-BsiWI for $V_k$ genes, respectively. In second step, the $V_H$ genes were cloned in vector containing $V_L$ using NcoI-NheI restriction enzymes to obtain final Fab library. About 66%-85% clones were found to encode full-length in-frame clones in different libraries. The library was evaluated against 7 targets and was found to yield antibodies against all of them. After three rounds of selection, 16-88% (scFv library) and 10-48% (Fab library) of the clones were found to be positive against the different targets.

Kugler el al., 2015 (Kugler, J., S. Wilke, D. Meier, F. Tomszak, A. Frenzel, T. Schirrmann, S. Dubel, H. Garritsen, B. Hock, L. Toleikis, M. Schutte and M. Hust (2015). "Generation and analysis of the improved human HAL9/10 antibody phage display libraries." BMC Biotechnol 15: 10) reported construction of two combinatorial naïve human antibody libraries in scFv format comprising of total 1.5× $10^{10}$ clones, encoding $V_k$ and $V_\lambda$ antibody genes amplified from the RNA isolated from PBMCs of 54 and 98 donors, respectively and $V_H$ antibody genes amplified from the RNA isolated from PBMCs of 98 donors. The variable heavy and light antibody genes were separately amplified from cDNA using a set of degenerate primers using PCR. The $V_L$ genes were cloned separately into pHAL30 vector using MluI-NotI restriction enzymes to obtain 1×$10^9$ clones each for $V_k$ and $V_\lambda$ library followed by cloning of $V_H$ gene repertoire in $V_L$ containing vector using NcoI-HindIII restriction enzymes.

Pasello el al., 2016 (Pasello, M., S. Zamboni, A. Mallano, M. Flego, P. Picci, M. Cianfriglia and K. Scotlandi (2016). "Design and construction of a new human naïve single-chain fragment variable antibody library, IORISS1." J Biotechnol 224: 1-11) reported construction of a combinatorial naïve human antibody library in scFv format comprising of 1.2× $10^9$ clones, encoding antibody genes amplified from the RNA isolated from PBMCs of 15 donors. The variable heavy and light antibody genes were separately amplified from cDNA using a set of degenerate primers using PCR. The $V_L$ and $V_H$ genes were assembled using two fragment splicing PCR and digested with NcoI-NotI and cloned in similarly digested pDNS vector. The library was evaluated against 6 targets and was reported to yield antibodies against all of them after 3-4 rounds of selection.

Kim et al., 2017 (Kim, S., I. Park, S. G. Park, S. Cho, J. H. Kim, N. S. Ipper, S. S. Choi, E. S. Lee and H. J. Hong (2017). "Generation, Diversity Determination, and Application to Antibody Selection of a Human Naïve Fab Library." Mol Cells 40(9): 655-666) reported construction of a combinatorial naïve human antibody library in Fab format comprising of 3×$10^{10}$ clones, encoding $V_k$ antibody genes amplified from the RNA isolated from PBMCs of 33 donors and $V_H$ antibody genes amplified from the RNA isolated from PBMCs of 803 donors, spleen of 2 donors, bone marrow of 2 donors, and lymph node of 2 donors. The variable heavy and light antibody genes were separately amplified from cDNA using a set of degenerate primers. The $V_L$ genes were cloned into pKRIBB-FabD vector using BstXI restriction enzyme to create pKFabD-$V_L$ library. The $V_H$ genes were then cloned into pKFabD-$V_L$ library using SfiI restriction enzyme to obtain pKFabD-$V_L$-$V_H$ Fab library. Using IMGT, 94% of $V_H$ and 97% of $V_K$ sequences were found to encode functional genes without stop codons. The library yielded specific binders against all the 10 targets employed in the study after 3-4 rounds of selection.

Nelson and Valadon 2017 (Nelson, R. S. and P. Valadon (2017). "A universal phage display system for the seamless construction of Fab libraries." J Immunol Methods 450: 41-49) have demonstrated the use of Type IIs enzymes for the seamless cloning of antibodies in Fab format useful for creation of human, mouse and rabbit Fab antibody libraries. The strategy involves the digestion of both vector and inserts with Type IIs enzymes to create overhangs for directional gene cloning.

US2009/0054254 A1 discloses a method for generation of scFv antibody libraries from memory B cells of naïve and convalescent/vaccinated donors. The $V_L$ and $V_H$ genes were amplified using PCR with a set of degenerate primers. The $V_L$ genes were cloned in PDV-C06 vector using SalI and NotI restriction enzymes.

WO 2018/002952 A2 discloses a method for construction of a large human antibody library in Fab format and isolation of specific binders against different targets comprising of 8.86×$10^{10}$ to 9.13×$10^{11}$ (3.06×$10^{11}$) clones encoding antibody genes from PBMCs of 15 donors, and bone marrow, tonsils and spleen from 1 donor each. However, only 80% clones in the library encode full-length translatable Fabs. Rest are short clones that persist even after phage rescue, which necessitates the use of elaborate screening steps to obtain binders during selections.

WO 2017/109721 A1 discloses a method for the creation of naïve phage-displayed library in Fab format to pan specific binders followed by further sorting using yeast display system. The antibody genes have been amplified using a set of degenerate primers and cloned into phagemid vector using HindIII-AscI and NcoI-XbaI restriction enzymes for light and heavy chains, respectively. About 90% clones have been reported to carry full-length Fab genes.

PCT/EP99/08856 discloses a method for the construction of large combinatorial scFv library that involves creation of a small primary library of 7×$10^7$ clones, which is diversified using an in vivo recombination protocol to obtain a large secondary library. However, the process for construction of small primary library involves the use of restriction enzymes for cloning $V_L$ and $V_H$ genes.

U.S. Pat. No. 6,794,128 B2 discloses a method for generation of naïve scFv library of 7×$10^9$ binders. The $V_L$ and $V_H$ genes were amplified using a set of degenerate primers and assembled as scFv using splice PCR. The scFv genes were cloned into phage vector using NcoI-NotI restriction enzymes.

US2002/0102613 A1 discloses a method for construction and use of Fab antibody libraries. A library of 4.3×$10^{10}$ was generated from the antibody genes were derived from PBMCs of 4 donors and spleen from 1 donor. The variable light and heavy chain genes were amplified using a set of degenerate primers and cloned as $V_{k/\lambda}$-$C_{k/\lambda}$ and $V_H$-$C_H$ using ApaL1-AscI and SfiI-BstEII restriction enzymes, respectively. In addition, the cloning of $V_H$-$C_H$ with Vλ-$C_\lambda$ as also done using SfiI-NotI enzymes to make a less restrictionbiased library. About 86% clones carried full-length Fab genes leading to an actual library size of $3.7 \times 10^{10}$ U.S. Pat. No. 5,969,108 discloses a method for one-step cloning of human antibody libraries in Fab format. This cloning technique is based on assembly of variable and constant domains using PCR followed by cloning into vectors using Sfi-NotI or NcoI-NotI restriction enzymes. The analysis of clones from the library revealed that about 90% of clones carried inserts.

Different methods of variable gene splicing, restriction enzyme (RE) digestion may lead to significant loss of some antibody gene families. Also, poor insert qualities lead to such libraries that make selection of specific binders an arduous task.

SUMMARY OF INVENTION

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

In an aspect of the present disclosure, there is provided a method for generating an antibody fragment library, said method comprising: (a) obtaining a sample from a subject for isolating nucleic acid; (b) amplifying the nucleic acid to yield amplicons covering all antibody gene fragments, wherein the amplification is performed using specific primers for antibody fragments; (c) assembling antibody gene fragments from the amplicons using emulsion-based splicing by Overlap Extension PCR (SOE-ePCR) to obtain antibody fragments, wherein the SOE-ePCR is performed using common primers; and (d) inserting the antibody fragments in a display vector to obtain recombinant clones, wherein the recombinant clones are used to transform E. coli to obtain the antibody fragment library.

In an aspect of the present disclosure, there is provided an antibody fragment library obtained by a method, said method comprising: (a) obtaining a sample from a subject for isolating nucleic acid; (b) amplifying the nucleic acid to yield amplicons covering all antibody gene fragments, wherein the amplification is performed using specific primers for antibody fragments; (c) assembling antibody gene fragments from the amplicons using emulsion-based splicing by Overlap Extension PCR (SOE-ePCR) to obtain antibody fragments, wherein the SOE-ePCR is performed using common primers; and (d) inserting the antibody fragments in a display vector to obtain recombinant clones, wherein the recombinant clones are used to transform E. coli to obtain the antibody fragment library.

In an aspect of the present disclosure, there is provided a method for selecting specific binders against a target molecule using an antibody fragment library, wherein the antibody fragment library is obtained by a method comprising: (a) obtaining a sample from a subject for isolating nucleic acid; (b) amplifying the nucleic acid to yield amplicons covering all antibody gene fragments, wherein the amplification is performed using specific primers for antibody fragments; (c) assembling antibody gene fragments from the amplicons using emulsion-based splicing by Overlap Extension PCR (SOE-ePCR) to obtain antibody fragments, wherein the SOE-ePCR is performed using common primers; and (d) inserting the antibody fragments in a display vector to obtain recombinant clones, wherein the recombinant clones are used to transform E. coli to obtain the antibody fragment library, said method comprising: (i) obtaining an antibody fragment library as described herein above; (ii) performing phage rescue from the antibody fragment library using a helper phage to yield phage libraries, wherein the phage libraries represent entire antibody fragment library; (iii) contacting the phage libraries to the target molecule; and (iv) selecting the specific binders against the target molecule.

In an aspect of the present disclosure, there is provided a method for generating a naïve human antibody fragment library, said method comprising: (a) obtaining a RNA sample from PBMCs of a human subject; (b) obtaining a first strand of cDNA from the RNA sample; (c) amplifying the first strand of cDNA using primers K1-K7 with C1 to yield amplicons comprising Signal sequence*-$V_\kappa$-$C_\kappa$* (*denotes partial sequence of gene encoding Signal sequence or Ck) fragments, and purifying the amplicons using non-ethidium bromide based stained gel for visualizing the amplicons using a blue light; (d) amplifying the first strand of cDNA using primers L1-L11 with C2 to yield amplicons comprising Signal sequence*-$V_L$-$C_L$* (*denotes partial sequence of gene encoding Signal sequence or $C_L$) fragments, and purifying the amplicons using non-ethidium bromide based stained gel for visualizing the amplicons using a blue light; (e) amplifying the first strand of cDNA using primers H1-H9 with HuJM32 to yield amplicons comprising L*-$V_H$-$C_{H1}$* (*denotes partial sequence of gene encoding Linker or CH1 gene of IgM isotype) fragments, and purifying the amplicons using non-ethidium bromide based stained gel for visualizing the amplicons using a blue light; (f) amplifying the amplicons of step (c) using primers K8-K13 with KS1-KS4 to yield amplicons comprising Signal sequence#-$V_\kappa$-Linker (L)* (#denotes partial sequence of gene encoding Signal sequence longer than step (c) and *denotes partial sequence of gene encoding Linker) fragments, pooling of the 24 amplicons obtained from 28 reactions and purifying the pool of amplicons using non-ethidium bromide based stained gel for visualizing the amplicons using a blue light; (g) amplifying the amplicons of step (d) using primers L12-L22 with LS1-LS3 to yield amplicons comprising Signal sequence#-$V_L$-Linker (L)* (#denotes partial sequence of gene encoding Signal sequence longer than step (d) and *denotes partial sequence of gene encoding Linker) fragments, pooling of all the 33 amplicons, and purifying the pool of amplicons using non-ethidium bromide based stained gel for visualizing the amplicons using a blue light; (h) amplifying the amplicons of step (e) using primers H10-H18 with HuJG-33 to yield amplicons comprising L-L-L-$V_H$-G-$C_{H1}$* (*denotes partial sequence of CH1 gene of IgG isotype) fragments, pooling of all the 9 amplicons, and purifying the pool of amplicons using non-ethidium bromide based stained gel for visualizing the amplicons using a blue light; (i) pooling equimolar concentrations of the amplicons of steps (f) and (h), and performing emulsion-based splicing by Overlap Extension PCR (SOE-ePCR) using primers PelBclo-51 and HuJGclo-34 to obtain spliced scFv comprising #Signal sequence-$V_\kappa$-L-L-L-$V_H$-G-$C_{H1}$* [#denotes partial sequence of gene encoding Signal sequence as in step (f) and *denotes partial sequence of CH1 gene of IgG isotype as in step (h)] fragments, and purifying amplicons using non-ethidium bromide based stained gel for visualizing the amplicons using a blue light; (j) pooling equimolar concentrations of the amplicons of steps (g) and (h), and performing emulsion-based splicing by Overlap Extension PCR (SOE-ePCR) using primers PelBclo-51 and HuJGclo-34 to obtain spliced scFv comprising #Signal sequence-$V_L$-L-L-L-$V_H$-$GC_{H1}$* [*denotes partial sequence of gene encoding Signal sequence as in step (g) and *denotes partial sequence of CH1 gene of IgG isotype as in step (h)] fragments, and purifying amplicons using non-ethidium bromide based stained gel for visualizing the amplicons using a blue light; (k) treatment of spliced scFv of step (i) and (j) with T4 DNA polymerase in the presence of dTTP to generate 4 base 5' overhangs, TGGC at the 5' end and CGCT at the 3' end; (1) digesting pVCHuscFvSacBclo36006 phagemid vector with BsaI restriction enzyme to produce linearized vector with 4 base 5' overhangs, GCCA at the 5' end and AGCG at the 3' end; (m) ligating the scFv products of step (k) individually to BsaI linearized phagemid vector of step (1) to obtain recombinant vector and transforming the recombinant vector in a E. coli cell to obtain the naïve human antibody fragment library, wherein the naïve human antibody fragment library comprises two libraries, and wherein the two libraries consists of a first library comprising scFv of $V_\kappa$-L-L-L-$V_H$ products and a second library comprising scFv of $V_L$-L-L-L-$V_H$ products; and (n) storage of antibody libraries as 16 mini-libraries comprising scFv in $V_\kappa$-L-L-L-$V_H$ format and 20 mini-libraries comprising scFv in $V_L$-L-L-L-$V_H$ format, wherein the signal sequence is PelB, and wherein the method leads to generation of the naïve human antibody fragment library and the library comprises at least 8 billion clones.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

FIG. 1 depicts a strategy for PCR based amplification and assembly of antibody variable genes in scFv format and preparation of inserts for cloning, in accordance with an embodiment of the present disclosure. # represents partial PelB sequence (last 23 bases of PelB), * Denotes partial IgM or IgG CH1 sequence, $ Denotes partial PelB sequence in the vector (First 48 bases, including 5 bases that are common in the vector and the insert).

Figure 4:
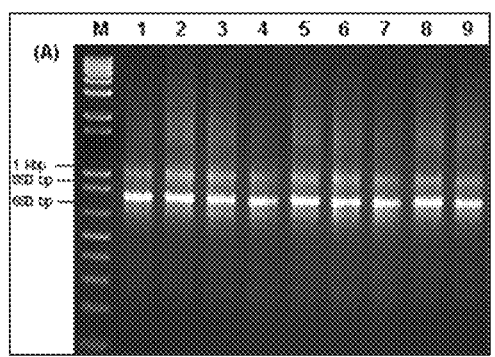
Figure 4:
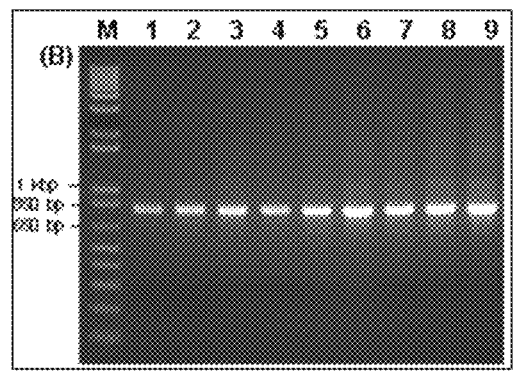
Figure 4:
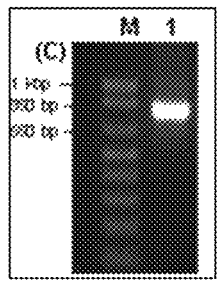
Figure 4:
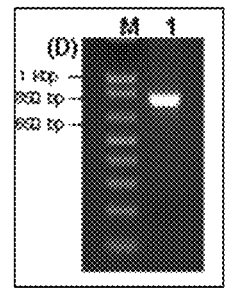

FIG. 4 depicts assembly of antibody variable genes using Splicing by Overlap Extension-emulsion PCR (SOE-ePCR), in accordance with an embodiment of the present disclosure. (A). Conventional SOE-PCR (SOE-cPCR) of variable antibody genes. Lane M; 1 kb plus DNA marker. Lane 1-3; SOE-cPCR product with 2 ng template for 25, 30, 35 cycles of amplification respectively, Lane 4-6; SOE-cPCR product with 3 ng template for 25, 30, 35 cycles of amplification, Lane 7-9; SOE-cPCR product with 4 ng template for 25, 30, 35 cycles of amplification. (B). Emulsion based SOE-PCR (SOE-ePCR) of variable antibody genes. Lane M; 1 kb plus DNA marker. Lane 1-3; SOE-ePCR product with 2 ng template for 25, 30, 35 cycles of amplification respectively, Lane 4-6; SOE-ePCR product with 3 ng template for 25, 30, 35 cycles of amplification, Lane 7-9; SOE-ePCR product with 4 ng template for 25, 30, 35 cycles of amplification. (C). Preparative scale assembly of variable kappa light chain gene with variable heavy chain gene using SOE-ePCR with 2 ng template for 35 cycles of amplification. Lane M; 1 kb plus DNA marker. Lane 1; VK-Linker-VH SOE-ePCR product. (D). Preparative scale assembly of variable lambda light chain gene with variable heavy chain gene using SOE-ePCR with 2 ng template for 35 cycles of amplification. Lane M; 1 kb plus DNA marker. Lane 1; VL-Linker-VH SOE-ePCR product.

Figure 5:
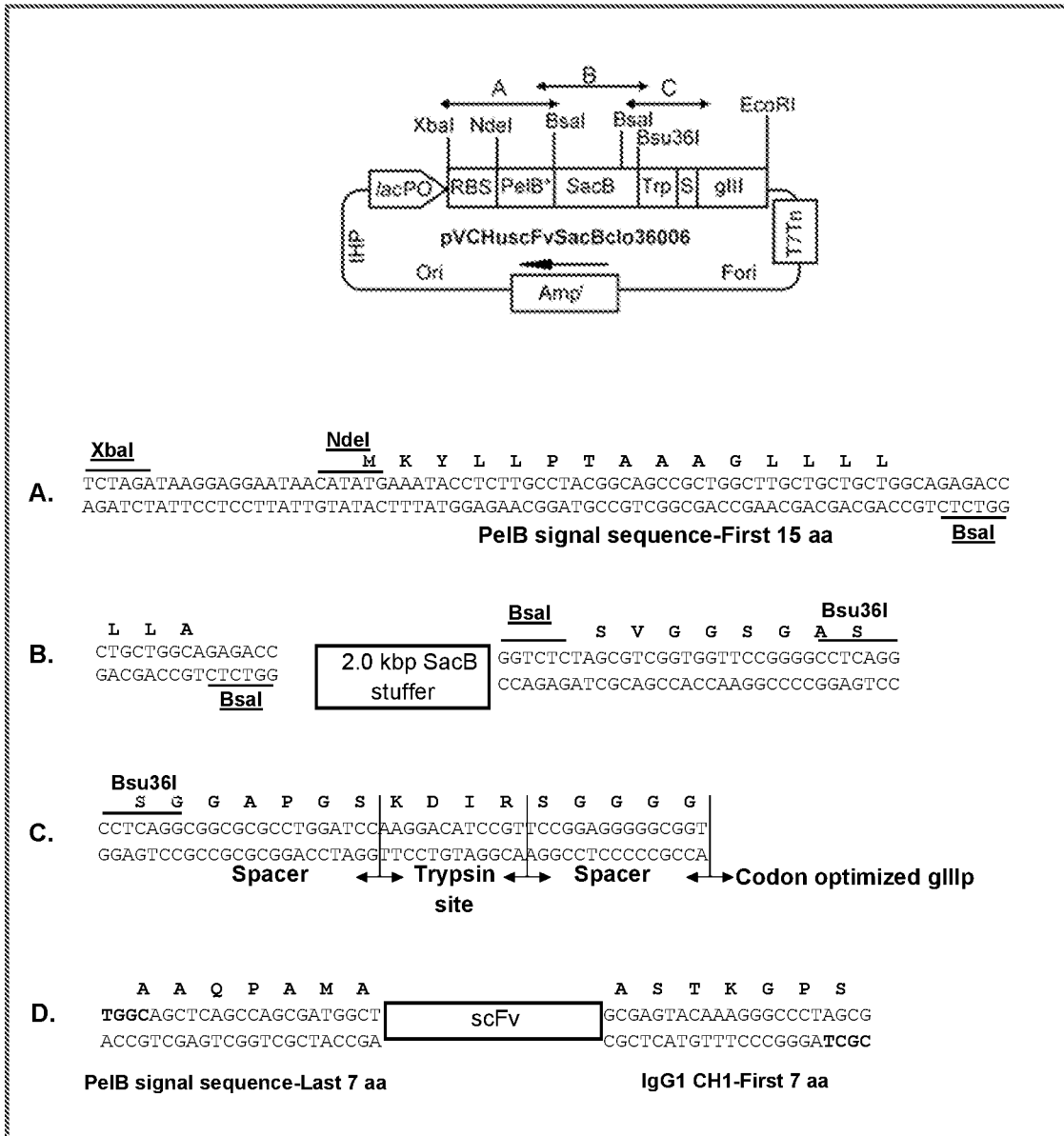

FIG. 5 depicts a representation of phagemid based phage display vector for cloning antibody variable genes in scFv format, in accordance with an embodiment of the present disclosure. The encoded amino acids are shown in single letter code (bold) above the nucleotide sequence (A-D). A-C Sequences of important components of the vector including cloning sites. D. Sequences flanking the variable scFv genes, encoding last 7 amino acid residues of PelB signal sequence at 5' end and first 7 amino acid residues of IgG1 CH1 at 3' end.

Figure 6:
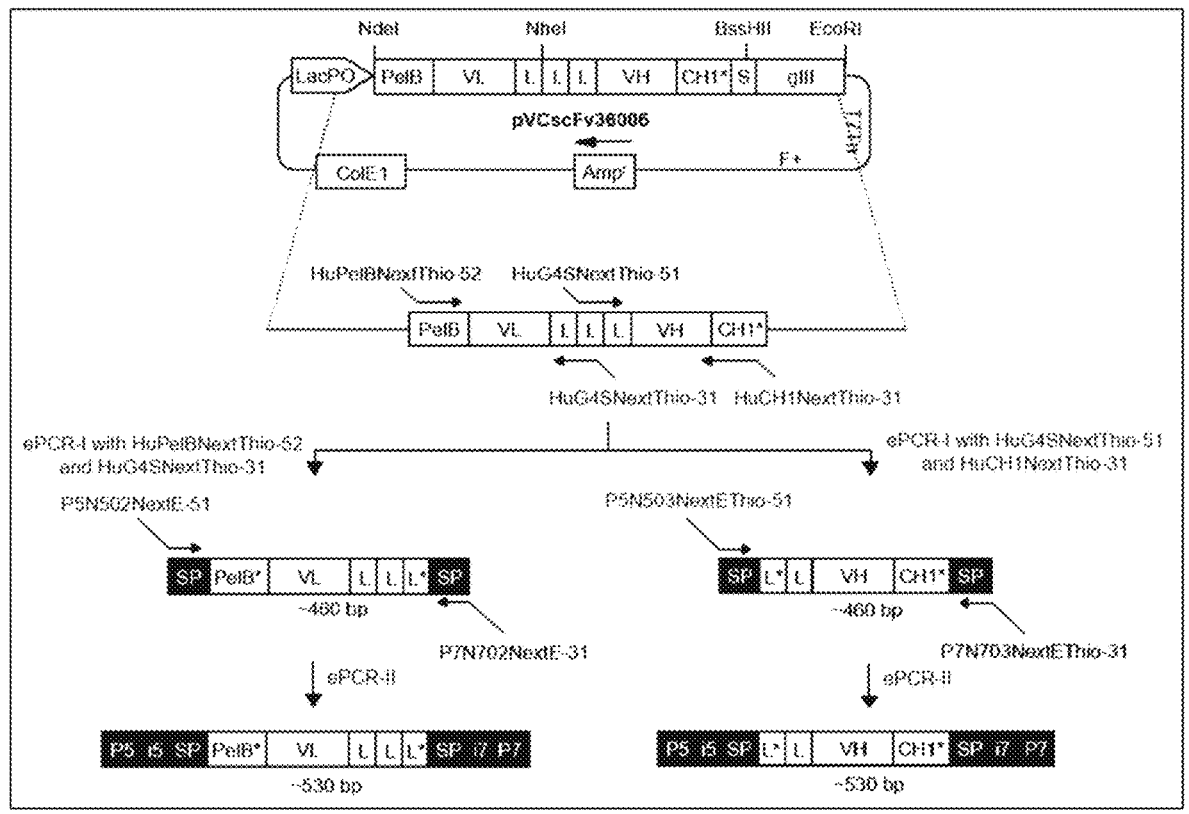

FIG. 6 depicts a strategy for preparation of dual-indexed human variable light and heavy chain libraries for NGS using Illumina MiSeq platform, in accordance with an embodiment of the present disclosure.

Figure 7:
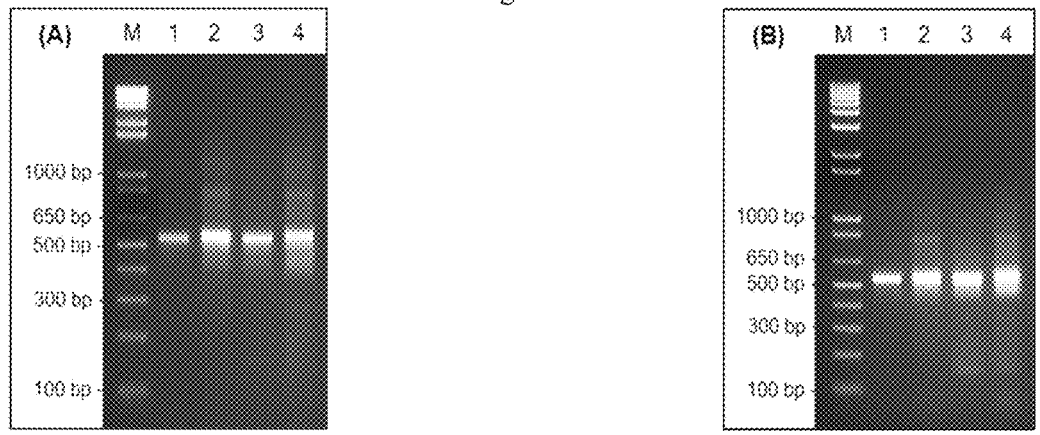

FIG. 7 depicts the amplification results of dual-indexed Human variable light and heavy chain libraries employed for NGS using Illumina MiSeq platform, in accordance with an embodiment of the present disclosure. (A) Analysis of 2-step ePCR amplified dual-indexed variable domain libraries derived from Human Kappa 015 mini-library. Lane M, 1 kb DNA ladder; Lane 1, Dual-indexed Human Variable Kappa chain library, ePCR-II; Lane 2, Dual-indexed Human Variable Kappa chain library, cPCR-II; Lane 3, Dual-indexed Human Variable Heavy chain library, ePCR-II; Lane 4, Dual-indexed Human Variable Heavy chain library; cPCR-II. (B) Analysis of 2-step ePCR amplified dual-indexed variable domain libraries derived from Human Lambda 010 mini-library. Lane M, 1 kb DNA ladder; Lane 1, Dual-indexed Human Variable Lambda chain library, ePCR-II; Lane 2, Dual-indexed Human Variable Lambda chain library, cPCR-II; Lane 3, Dual-indexed Human Variable Heavy chain library, ePCR-II; Lane 4, Dual-indexed Human Variable Heavy chain library; cPCR-II.

Figure 8:
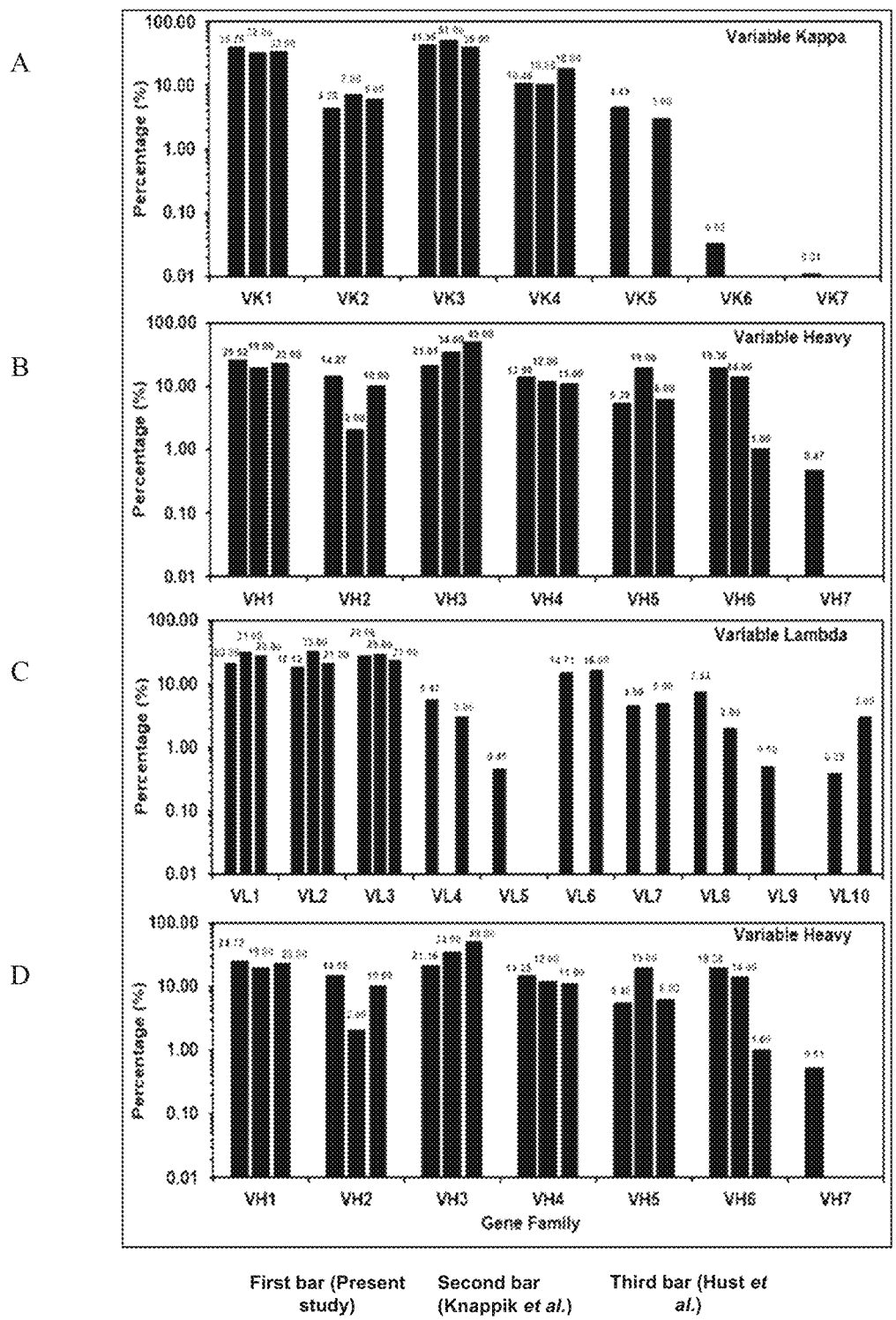

FIG. 8 depicts representation of variable gene families in the naïve human antibody library, in accordance with an embodiment of the present disclosure.

Figure 9:
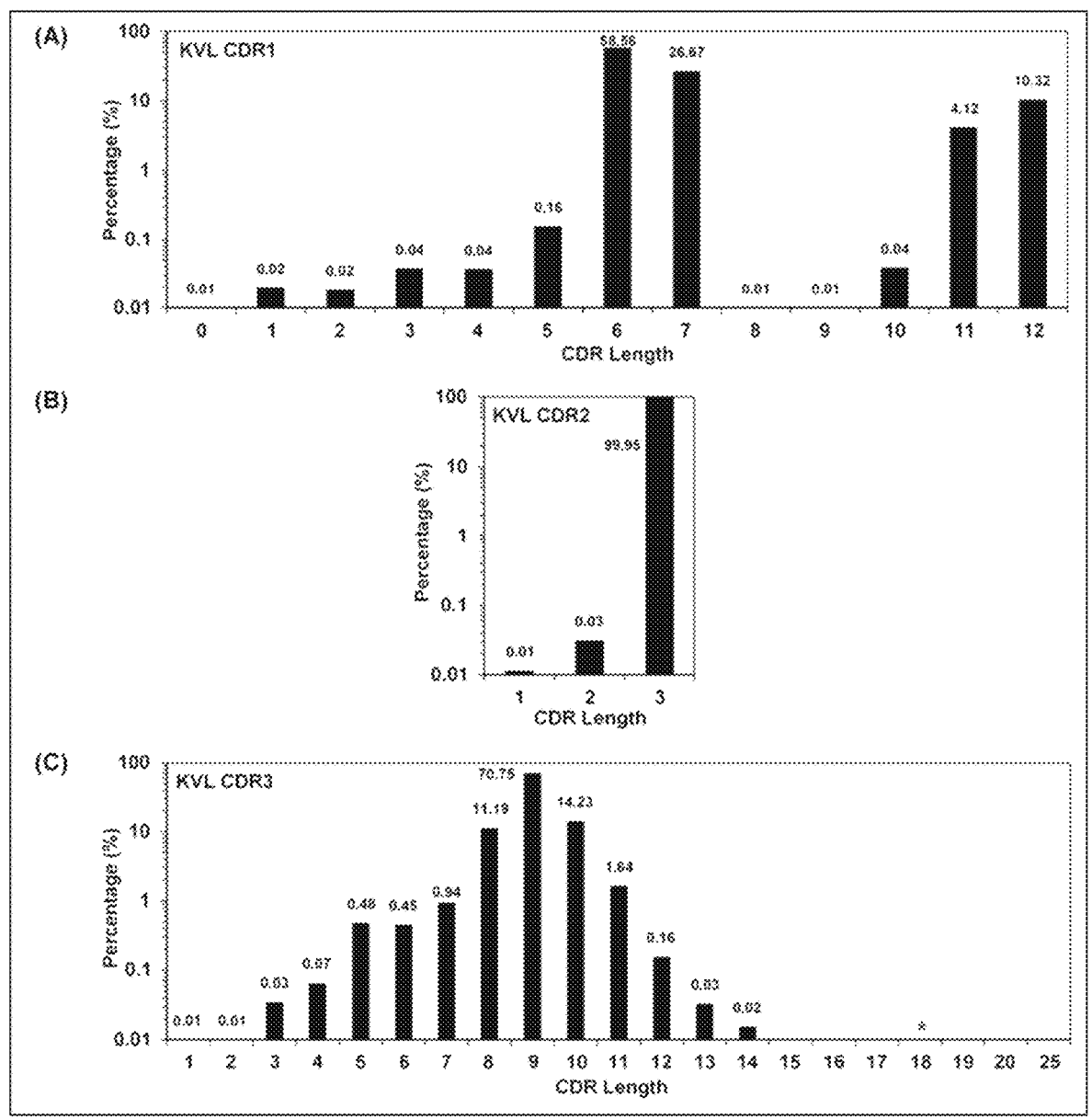

FIG. 9 depicts CDR length representation of variable kappa antibody domains encoded in Human Kappa 015 mini-library, in accordance with an embodiment of the present disclosure. * denotes that the number of sequences carrying CDR3 length in the range of 15-25 was less than 0.01%, but was not zero.

Figure 10:
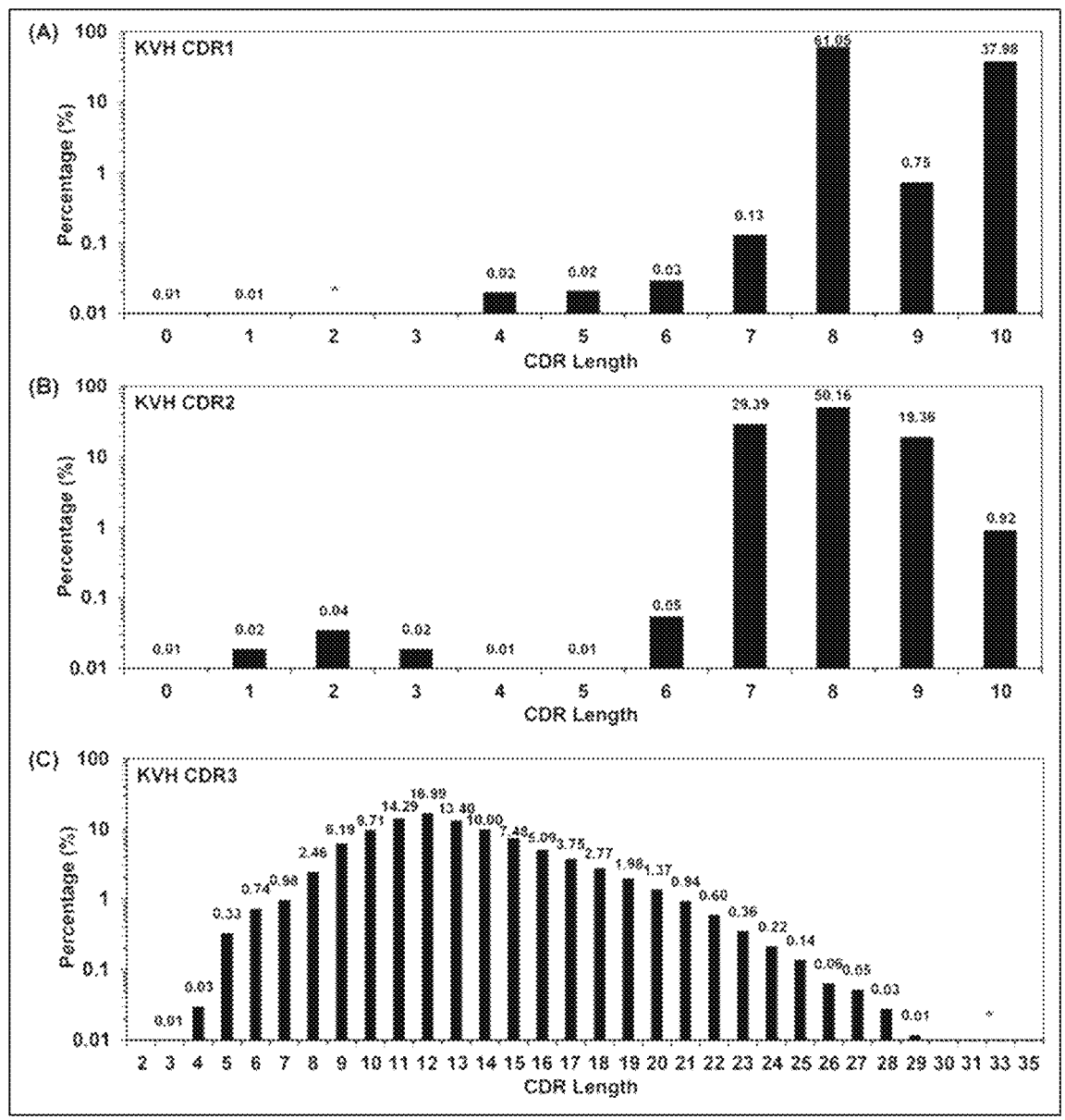

FIG. 10 depicts CDR length representation of variable heavy chain antibody domains encoded in Human Kappa 015 mini-library, in accordance with an embodiment of the present disclosure. * denotes that the number of sequences carrying CDR1 length in the range of 2-3 and CDR3 length in the range of 30-35 was less than 0.01%, but was not zero.

Figure 11:
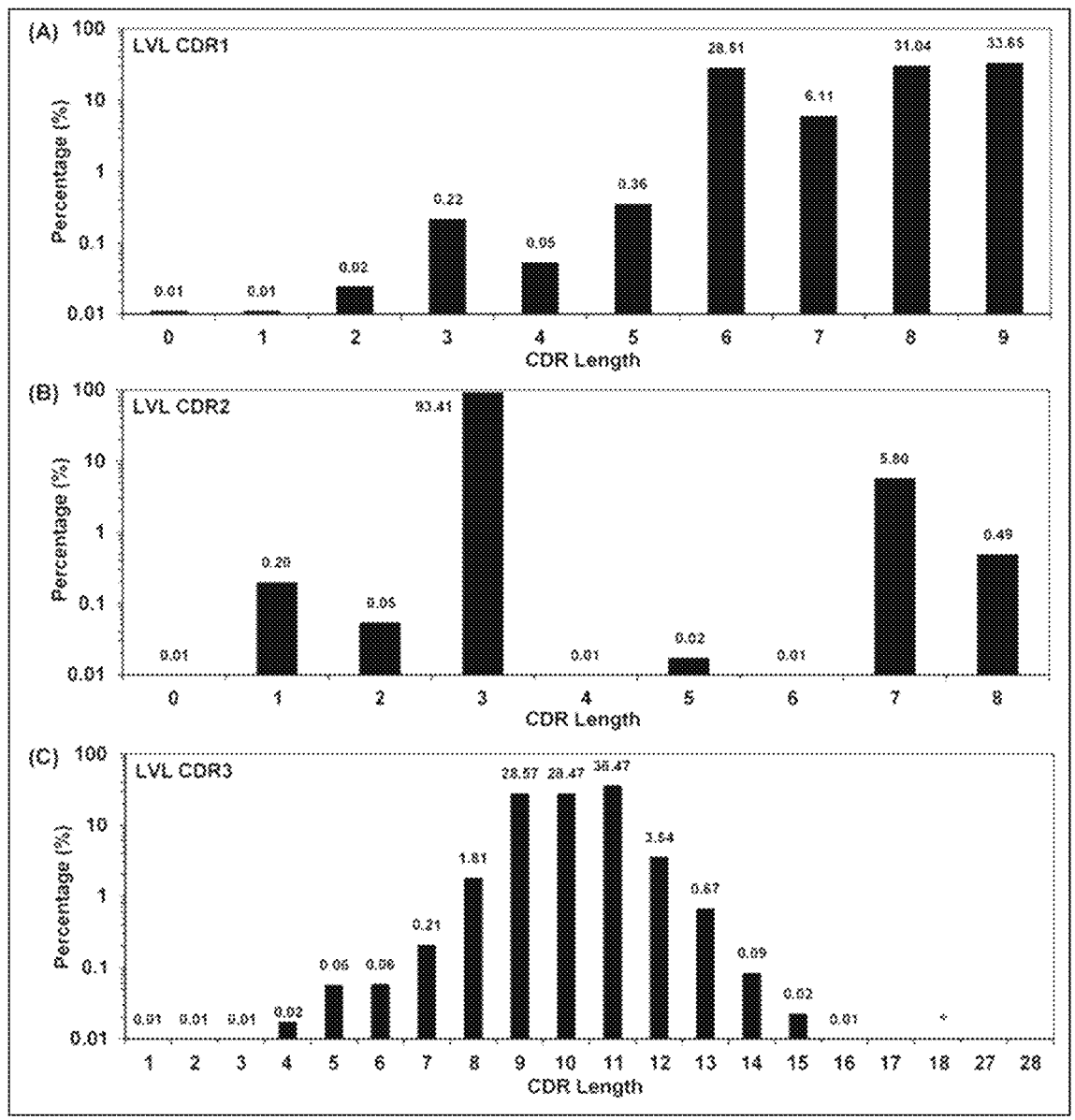

FIG. 11 depicts CDR length representation of variable lambda chain antibody domains encoded in Human Lambda 010 mini-library, in accordance with an embodiment of the present disclosure. * denotes that the number of sequences carrying CDR3 length in the range of 17, 18, 27 and 28 was less than 0.01%, but was not zero.

Figure 12:
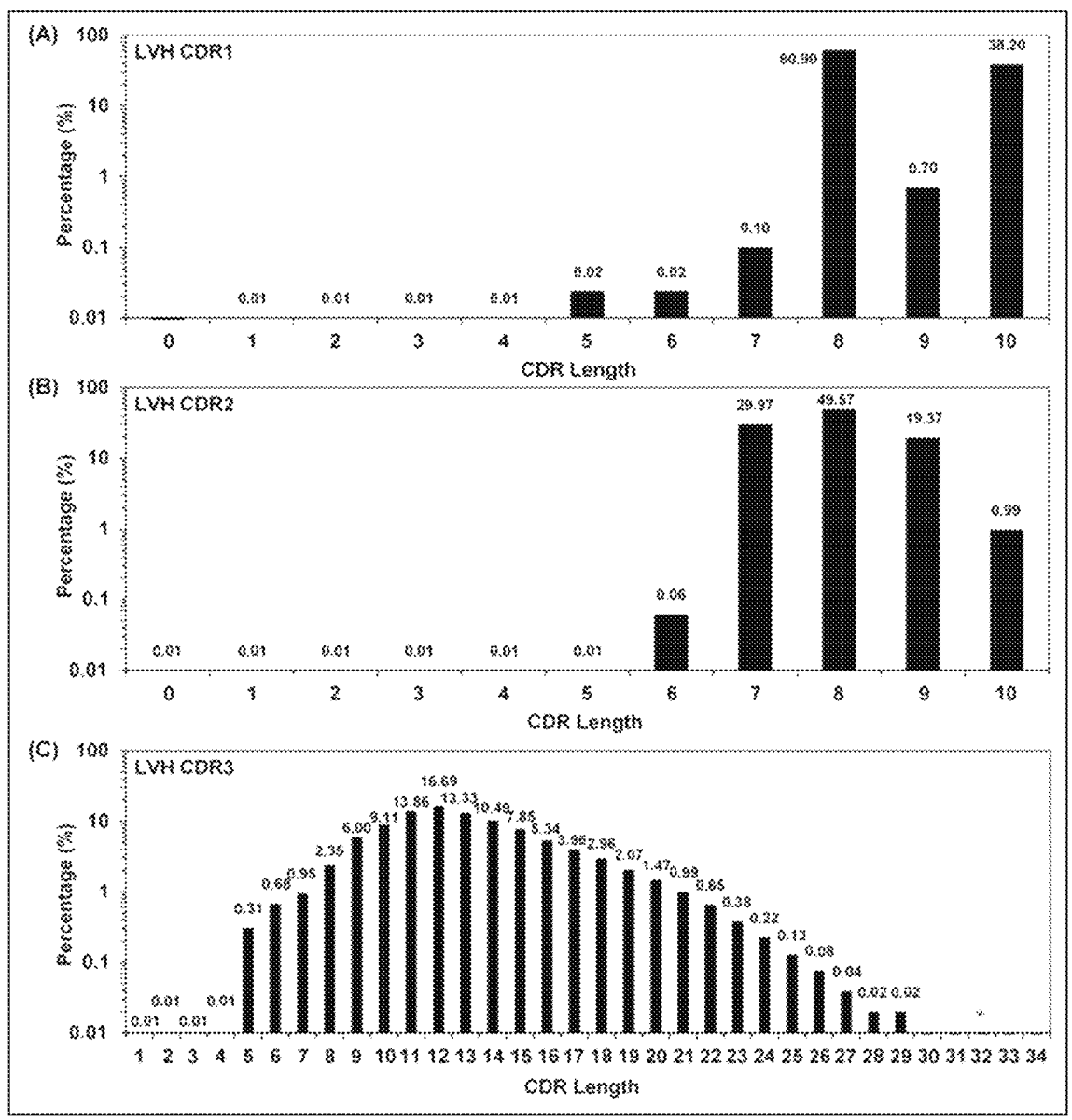

FIG. 12 depicts CDR length representation of variable heavy chain antibody domains encoded in Human Lambda 010 mini-library, in accordance with an embodiment of the present disclosure. * denotes that the number of sequences carrying CDR3 length in the range of 30-34 was less than 0.01%, but was not zero.

Figure 13:
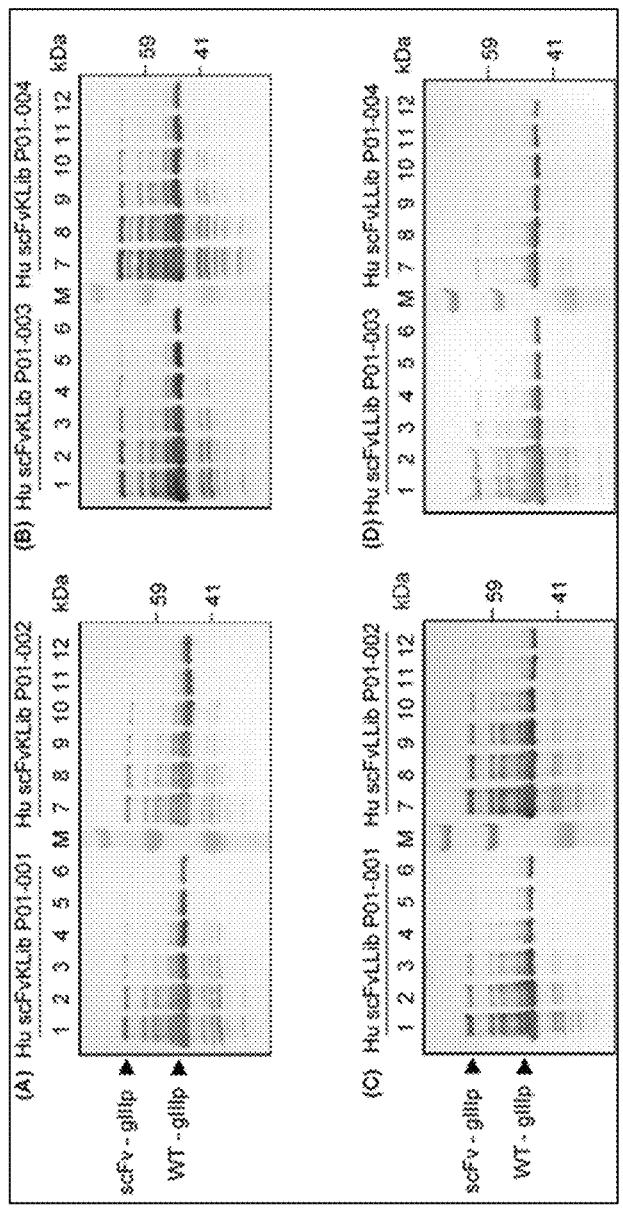

FIG. 13 depicts analysis of scFv-gIIIp fusion display in AGM13 helper phage rescued human kappa and lambda antibody phage display libraries, in accordance with an embodiment of the present disclosure. (A-B). Display in Hu scFv kappa phage library 001-004. (C-D). Display in Hu scFv lambda phage library 001-004.

Figure 14:
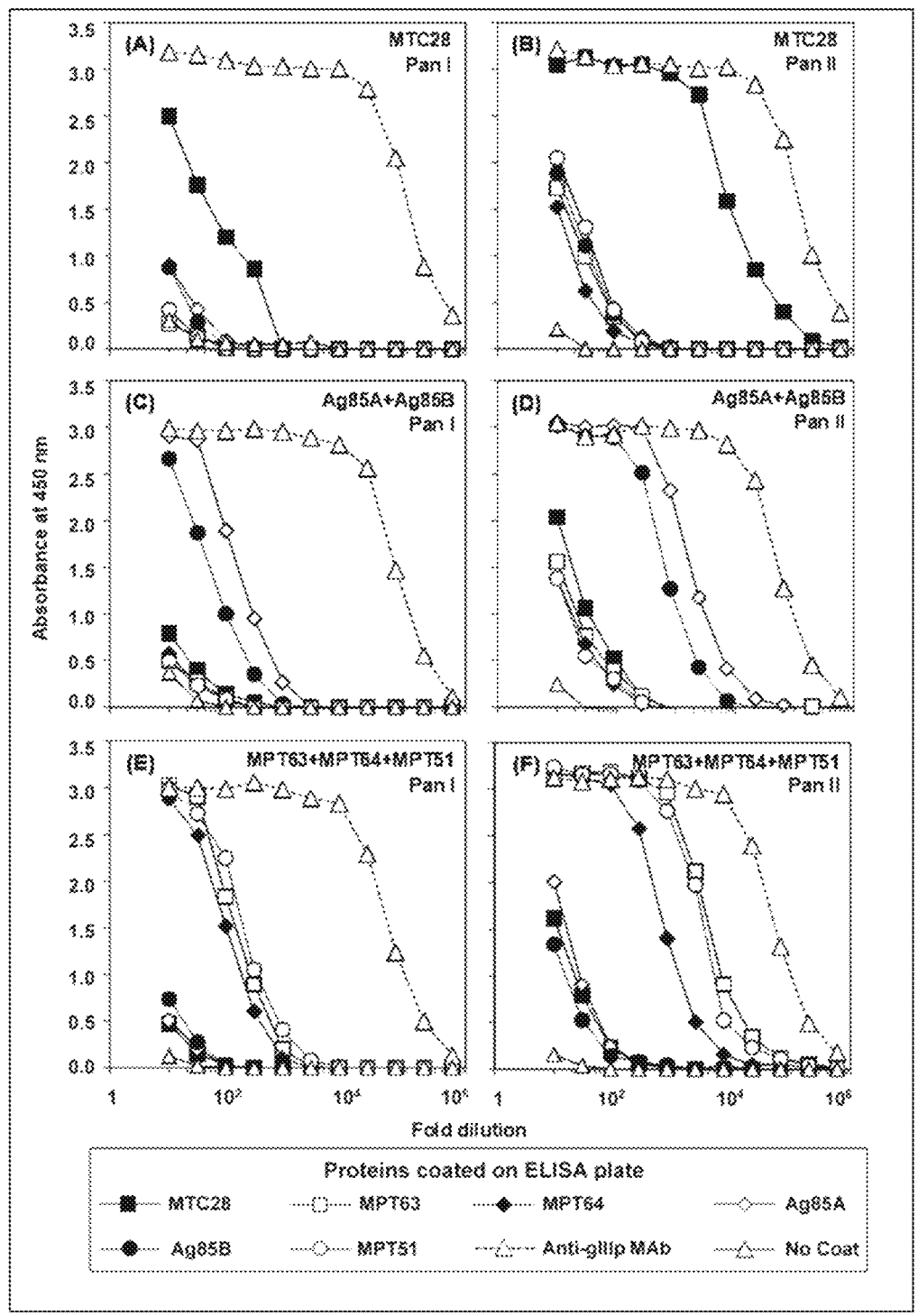

FIG. 14 depicts Phage ELISA reactivity of amplified phage pools obtained after first and second round of affinity selection against 3 sets of biotin-tagged mycobacterial proteins, in accordance with an embodiment of the present disclosure.

Figure 15:
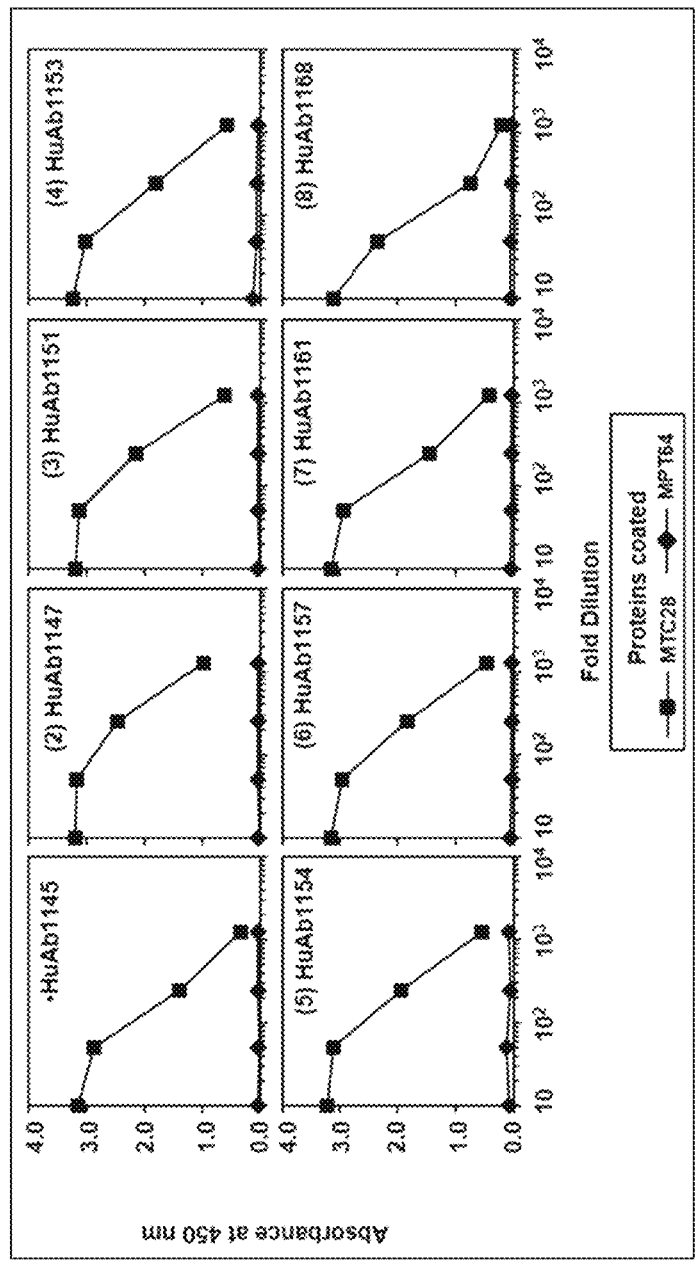

FIG. 15 depicts Phage ELISA reactivity of representative clones obtained after three rounds of affinity selection on MTC28-Bio protein, in accordance with an embodiment of the present disclosure.

Figure 16:
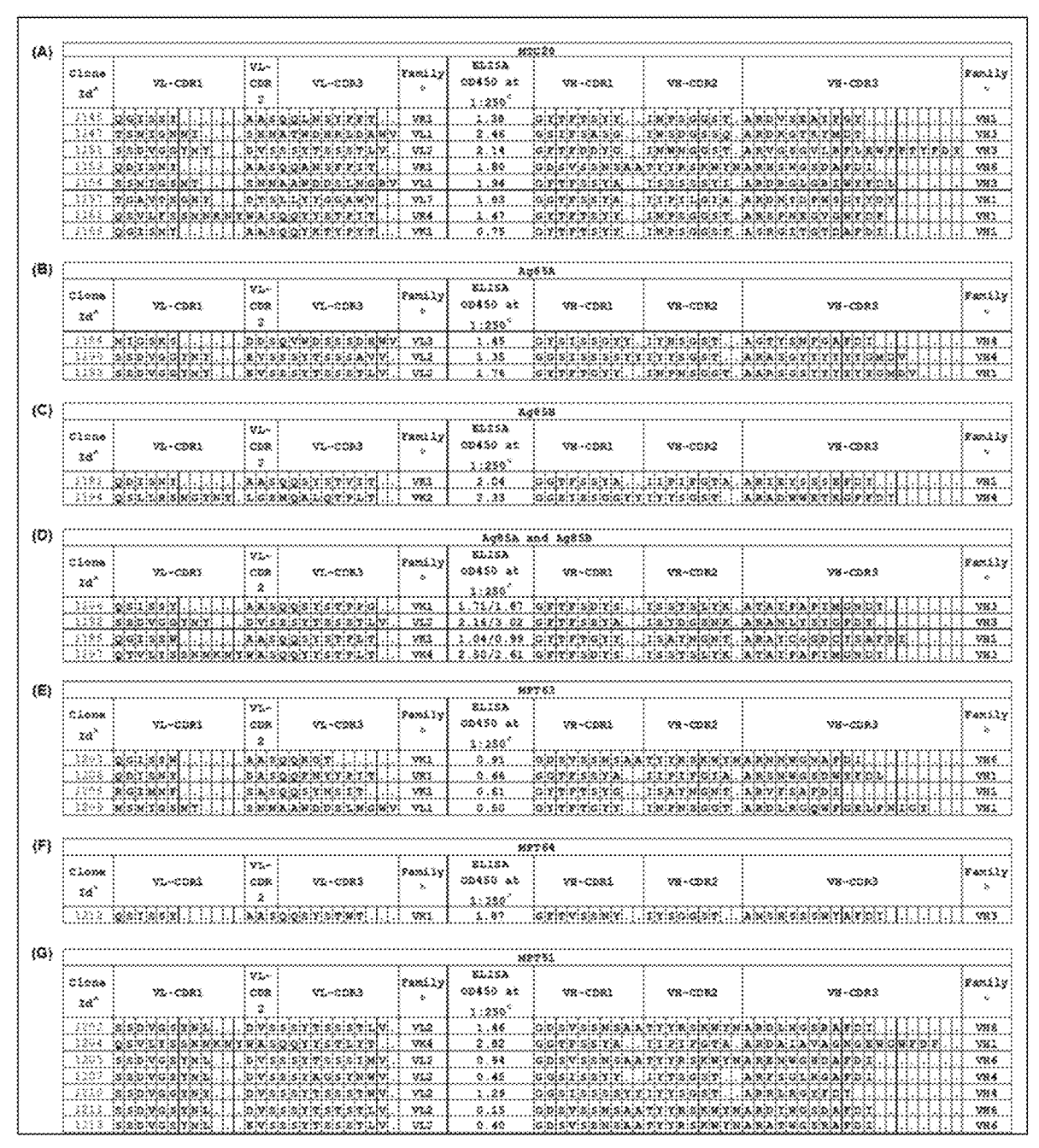

FIG. 16 depicts sequences of Complementarity Determining Regions (CDRs) of target protein specific representative scFvs selected from human naïve scFv library, in accordance with an embodiment of the present disclosure. a denotes the Clone Id given to each specific scFv. $^b$ denotes the variable gene family as determined using IMGT. C denotes the phage ELISA reactivity of the crude phage supernatant at 250-fold dilution against the specific antigen.

Figure 17:
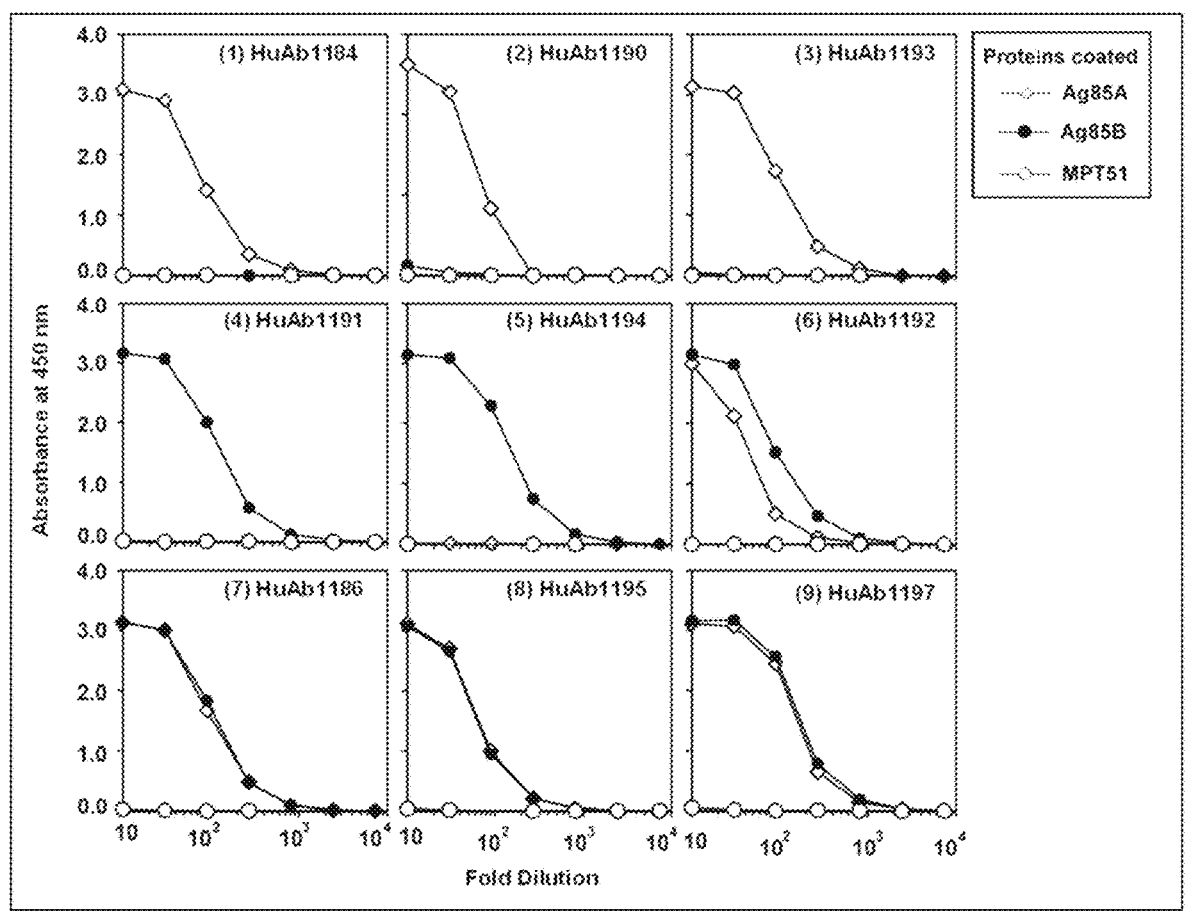

FIG. 17 depicts Phage ELISA reactivity of individual representative clones obtained after three rounds of affinity selection on a mixture of Ag85A-Bio, Ag85B-Bio proteins and MPT51-Bio, in accordance with an embodiment of the present disclosure.

Figure 18:
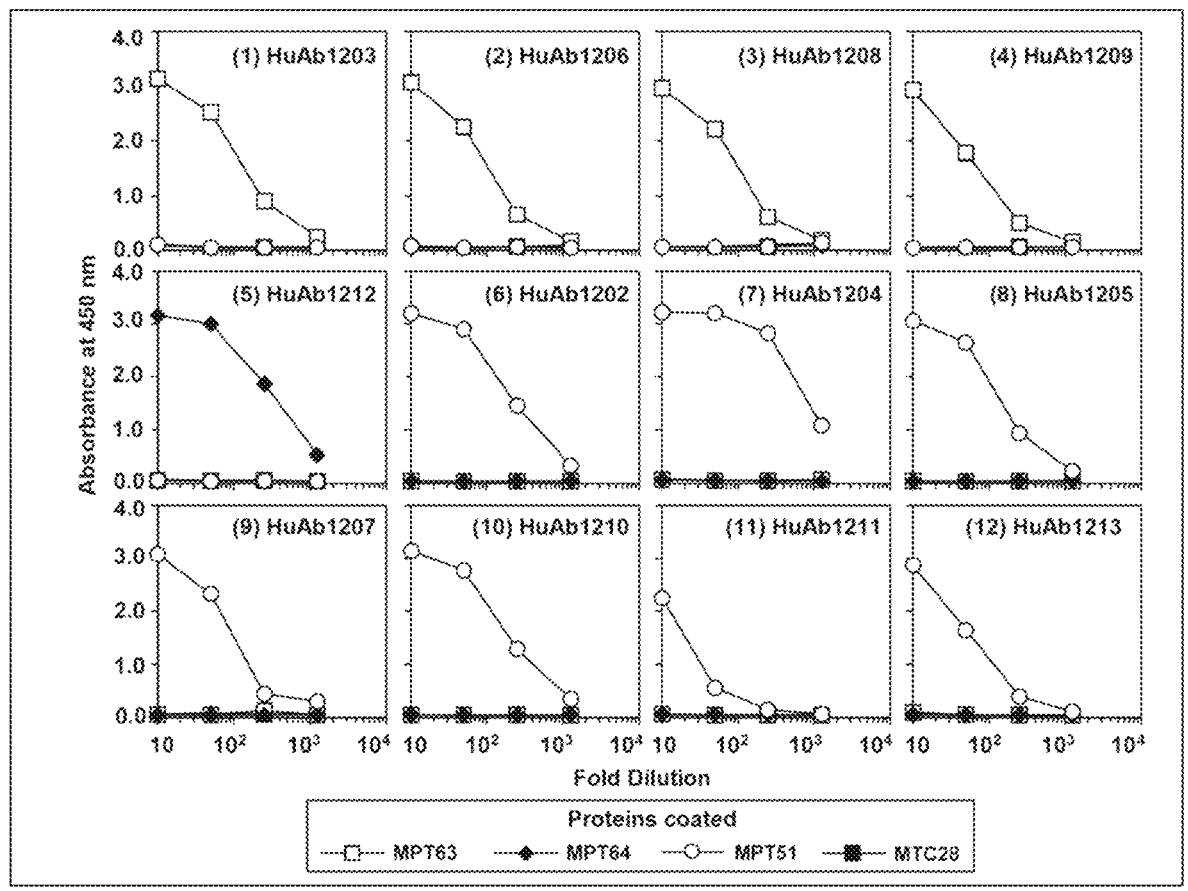

FIG. 18 depicts Phage ELISA reactivity of individual representative clones obtained after three rounds of affinity selection on a mixture of MPT63-Bio, MPT64-Bio, MPT51-Bio proteins and MTC28-Bio, in accordance with an embodiment of the present disclosure.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term naïve library refers to a collection of nucleic acid sequences encoding a naturally occurring antibody gene fragments ($V_H$, $V_L$, and $V_\kappa$) from a non-immunized source.

cDNA refers to a double stranded DNA synthesised from a single stranded RNA template in a reaction catalysed by the enzyme reverse transcriptase.

Phagemid vector refers to a DNA expression system, which can be replicated as a plasmid, and also be packaged as a single stranded DNA in viral particles. Phagemid is used to accommodate the whole repertoire of antibody genes wherein post infection to bacteria it requires additional proteins provided by helper phage to create phage particles that display recombinant protein of interest.

The term 'specific binder' refers to a molecule which can be scFv fragment, Fab fragment, or any other antibody fragment that is obtained by the method for isolating specific binder from the antibody fragment library as disclosed in the present disclosure. The binder is isolated against the target molecule as disclosed in the present disclosure.

The term 'single cell fragment variable' (scFv) refers to an antibody fragment where the variable light and heavy chain domains are linked to each other via a 15-18 amino acid linker.

The term 'antibody fragment' refers to the portion of full-length antibody, which is capable of binding to the antigen. This could be scFv or Fab.

As per the present disclosure, 'restriction enzyme free insert preparation' refers to a method for preparing amplified nucleic acid inserts with cohesive ends without the use of any restriction enzyme.

As per the present disclosure, 'common primers' refers to the primers that anneal to a region present in all the template molecules and 'specific primers' refers to the primers that anneal to a region whose sequence is different in different template molecules and hence are template specific.

The term 'short clones' refer to recombinants that carry partial/incomplete antibody gene fragments. They could be missing either variable light or heavy chain gene. Semi-synthetic antibody library consists of a population of antibodies in which the CDR (complementarity determining region) has been replaced by synthetic amino acid sequence of varying length and composition. Synthetic antibody library consists of antibody sequences in which both framework sequences and CDR are synthetic and CDR has varied composition and different length of sequences.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

Naive or immunized antibody libraries can be constructed by cloning the antibody repertoires encoded in the RNA isolated from B-cells of non-immunized or immunized individuals, respectively (Hoogenboom, H. R. (2005). "Selecting and screening recombinant antibody libraries." Nat Biotechnol 23(9): 1105-1116). Structure-based semi-synthetic or synthetic libraries containing diversified Complementarity Determining Regions (CDRs) and few selected optimal Framework regions (FRs) have also become available (Knappik, A., L. Ge, A. Honegger, P. Pack, M. Fischer, G. Wellnhofer, A. Hoess, J. Wolle, A. Pluckthun and B. Virnekas (2000). "Fully synthetic human combinatorial antibody libraries (HuCAL) based on modular consensus frameworks and CDRs randomized with trinucleotides." J Mol Biol 296(1): 57-86; Hoogenboom 2005). Such libraries also alleviate the need for humanization of mouse/rabbit monoclonal antibodies before they can be employed for therapeutic applications.

It is often noted that antibodies retrieved from naive human libraries have relatively lower affinities and may require an additional and tedious step of affinity-maturation to achieve desired range of affinities. However, large library size can serve as solution to this problem. Large library size would allow better access to diverse antibody repertoires thereby improving chances of finding target specific antibodies within desired range of affinities. Human antibody libraries with size in the range of $1 \times 10^{10-11}$ have led to isolation of antibodies with affinities in sub-nanomolar range. But, construction of such large libraries is a huge effort and may require large number of electroporations to obtain the target size.

Naïve human antibody libraries provide an excellent opportunity to explore the immaculate natural human antibody repertoire, which in itself is highly competent to generate immune response against almost every antigen. Hence, such libraries tend to be universal in nature and in principle contain binders to every possible antigen.

The present disclosure describes a novel combination of recombinant DNA technologies that has enabled construction of phage displayed naive human antibody libraries of superior quality. Rationally designed emulsion-based SOE-PCR (SOE-ePCR) has been employed for the assembly for antibody variable gene repertoire to produce clean and accurate scFv fragments. These PCR amplicons are compatible with the restriction enzyme-free cloning strategy that has been employed for seamless cloning of scFv fragments in a specially designed antibody phage display vector to produce a naive human scFv library comprising of approximately 10 billion clones. Furthermore, use of 'Blue-light' during all the DNA manipulations involving agarose-gels has led to improved ligation and transformation efficiencies making the construction of such a large library a simplified task. The performance of library has been demonstrated by selection of large number of different yet specific scFv binders against several recombinant *Mycobacterium tuberculosis* proteins. The method described, holds tremendous potential for the streamlined construction of antibody libraries with significantly improved quality and performance during affinity-selection against target antigens.

Also described in the present disclosure, is validation of the naïve human antibody library obtained by the methods as disclosed herein. Next-generation sequencing has been employed to characterize the library at genome-scale. The functional validation of the large phage displayed naïve human antibody library has been performed using 6 biotinylated mycobacterial proteins carrying single biotin residue at the C-terminus via 15 amino acid Biotin acceptor peptide tag as a bait.

The present disclosure is not to be limited in scope by the specific embodiments described herein, which are intended for the purposes of exemplification only. Functionally-equivalent products, compositions, and methods are clearly within the scope of the disclosure, as described herein.

In an embodiment of the present disclosure, there is provided a method for generating an antibody fragment library, said method comprising: (a) obtaining a sample from a subject for isolating nucleic acid; (b) amplifying the nucleic acid to yield amplicons covering all antibody gene fragments, wherein the amplification is performed using specific primers for antibody fragments; (c) assembling antibody gene fragments from the amplicons using emulsion-based splicing by Overlap Extension PCR (SOE-ePCR) to obtain antibody fragments, wherein the SOE-ePCR is performed using common primers; and (d) inserting the antibody fragments in a display vector to obtain recombinant clones, wherein the recombinant clones are used to transform *E. coli* to obtain the antibody fragment library.

In an embodiment of the present disclosure, there is provided a method for generating an antibody fragment library as described herein, wherein the nucleic acid in step (b) optionally refers to a mixture of nucleic acid obtained from plurality of the subject. It is contemplated that similar method can be followed for constructing the antibody fragment library from a nucleic acid sample, which is a mixture of nucleic acid sample from more than one subject. In an embodiment of the present disclosure, there is provided a method for generating an antibody fragment library as described herein, wherein the sample is selected from the group consisting of peripheral blood mononuclear cells (PBMC), spleen, lymph nodes, bone marrow, tonsils, Gut-associated lymphoid tissue (GALT), peyers patches, and Hybridoma.

In an embodiment of the present disclosure, there is provided a method for generating an antibody fragment library as described herein, wherein the sample optionally refers to cells or a single cell derived from the sample selected from a group consisting of spleen, lymph nodes, bone marrow, tonsils, Gut-associated lymphoid tissue (GALT), peyers patches, and Hybridoma. It can be contemplated that the sample refers to single cells isolated from the samples (spleen, lymph nodes, bone marrow, tonsils, Gut-associated lymphoid tissue (GALT), peyers patches, and Hybridoma) by FACS sorting. This is a currently used technology for isolating antibodies from immunized or infected people or animals that using different kind of antibodies and labelled antigen, the antigen specific B cells are sorted as single cells. Then the RNA is extracted, cDNA made and VL and VH can be assembled into scFv or any other format).

In an embodiment of the present disclosure, there is provided a method for generating an antibody fragment library as described herein, wherein the subject is selected from the group consisting of human, mouse, rabbits, chicken, llama, camel, horse, sheep, cow, monkey, baboon, rat, hamster, guinea pig, dog, goat, ferret, shark, alligator, and porcine.

In an embodiment of the present disclosure, there is provided a method for generating an antibody fragment library as described herein, wherein the method generates either a naïve antibody fragment library, or an immunized antibody fragment library.

In an embodiment of the present disclosure, there is provided a method for generating an antibody fragment library as described herein, wherein the method described is also be applicable to constructing synthetic, semi-synthetic, or any kind of antibody library from any kind of cells.

In an embodiment of the present disclosure, there is provided a method for generating an antibody fragment library as described herein, wherein the subject is human, and the method generates a naïve human antibody fragment library.

In an embodiment of the present disclosure, there is provided a method for generating an antibody fragment library as described herein, wherein amplifying the nucleic acid to yield amplicons covering all antibody gene fragments is performed by emulsion-based PCR.

In an embodiment of the present disclosure, there is provided a method for generating an antibody fragment library as described herein, wherein the assembling of the antibody gene fragments is performed using emulsion-based splicing by Overlap Extension PCR (SOE-ePCR) to obtain the antibody fragments.

In an embodiment of the present disclosure, there is provided a method for generating an antibody fragment library as described herein, wherein the method does not use ultra-violet (UV) based visualization for the preparation of the amplicons, related fragments, and linearized vector.

In an embodiment of the present disclosure, there is provided a method for generating an antibody fragment library as described herein, wherein the assembly of antibody genes in obtained by splicing of variable antibody light chain genes ($V_\kappa$ and $V_L$) and variable antibody heavy chain genes ($V_H$).

In an embodiment of the present disclosure, there is provided a method for generating an antibody fragment library as described herein, wherein the antibody fragments are either scFv (single cell fragment variable) fragments or Fab fragments. In another embodiment of the present disclosure, the antibody fragments are scFv.

In an embodiment of the present disclosure, there is provided a method for generating an antibody fragment library as described herein, wherein the scFv fragment comprises at least one of $V_\kappa$-Linker-$V_H$ fragments, or $V_L$-Linker-$V_H$ fragments, or $V_H$-Linker-$V_L$ fragments, or combinations thereof.

In an embodiment of the present disclosure, there is provided a method for generating an antibody fragment library as described herein, wherein the display vector is selected from a group consisting of phagemid-based phage vector, phage vector, yeast display vector, mammalian display vector, bacterial display vector, and ribosome display vector. In another embodiment of the present disclosure, the display vector is phagemid-based phage vector.

In an embodiment of the present disclosure, there is provided a method for generating an antibody fragment library as described herein, wherein the method is independent of restriction enzyme in steps of preparing amplified nucleic acid inserts, assembling of antibody gene fragments from the amplicon, and cloning of antibody gene fragments.

In an embodiment of the present disclosure, there is provided a method for generating an antibody fragment library as described herein, wherein the phagemid based phage display vector is pVCHuscFvSacBclo36006. It can be contemplated that any other phagemid vector modified for restriction enzyme free cloning can be used. In the strategy of the present disclosure, the display vector is digested with BsaI, which produces 4 base 5' overhangs. However, other Type IIs enzymes that produce 4 base overhangs can also be used for doing the same thing. Further other Type IIs enzymes that produce shorter or longer overhangs can also be used.

In an embodiment of the present disclosure, there is provided an antibody fragment library obtained by a method, said method comprising: (a) obtaining a sample from a subject for isolating nucleic acid; (b) amplifying the nucleic acid to yield amplicons covering all antibody gene fragments, wherein the amplification is performed using specific primers for antibody fragments; (c) assembling antibody gene fragments from the amplicons using emulsion-based splicing by Overlap Extension PCR (SOE-ePCR) to obtain antibody fragments, wherein the SOE-ePCR is performed using common primers; and (d) inserting the antibody fragments in a display vector to obtain recombinant clones, wherein the recombinant clones are used to transform E. coli to obtain the antibody fragment library.

In an embodiment of the present disclosure, there is provided a method for selecting specific binders against a target molecule using an antibody fragment library, wherein the antibody fragment library is obtained by a method comprising: (a) obtaining a sample from a subject for isolating nucleic acid; (b) amplifying the nucleic acid to yield amplicons covering all antibody gene fragments, wherein the amplification is performed using specific primers for antibody fragments; (c) assembling antibody gene fragments from the amplicons using emulsion-based splicing by Overlap Extension PCR (SOE-ePCR) to obtain antibody fragments, wherein the SOE-ePCR is performed using common primers; and (d) inserting the antibody fragments in a display vector to obtain recombinant clones, wherein the recombinant clones are used to transform E. coli to obtain the antibody fragment library, said method comprising: (i) obtaining an antibody fragment library as described herein; (ii) performing phage rescue from the antibody fragment library using a helper phage to yield phage libraries, wherein the phage libraries represent entire antibody fragment library; (iii) contacting the phage libraries to the target molecule; and (iv) selecting the specific binders against the target molecule.

In an embodiment of the present disclosure, there is provided a method for selecting specific binders against a target molecule using an antibody fragment library as described herein, wherein the target molecule is selected from the group consisting of Mycobacterium sp. proteins, malarial parasite proteins, rabies virus proteins, Chikungunya virus proteins, dengue virus proteins, influenza virus proteins, Ebola virus proteins, Zika virus proteins, Nipah virus proteins, Hendra Virus proteins, West Nile virus proteins, Japanese Encephalitis Virus proteins, Chandipura Virus proteins, Hepatitis B virus proteins, Hepatitis C virus proteins, Human papilloma virus proteins, HIV proteins, snake venom proteins, thyroid hormones, CD20, EGFR (epidermal growth factor receptor), VEGFA (vascular endothelial growth factor A), TNFα (Tumor necrosis factor), CD (Cluster of differentiation)52 CD25, CD3, IgE (Immunoglobulin E), IIb/IIIa integrin receptor, EPO-R (Erythropoietin), G-CSF (granulocyte colony stimulating factor) receptor, GM-CSF receptor, testosterone, p-estradiol, IL-2, BSA (bovine serum albumin), lymphotoxin-β (LT-β), E-selectin ligand-1 (ESL-1), prostate specific antigen, chymotrypsin, human chorio gonadotropin (hCG), enzymes, cell-lines, lysozyme, Tetanus toxoid, attenuated rabies virus, Chikungunya virus, dengue virus, influenza virus, Ebola virus, Zika virus, Nipah virus, Hendra Virus, West Nile virus, Japanese Encephalitis Virus, Chandipura Virus, Hepatitis B virus, Hepatitis C virus, Human papilloma virus, HIV, rabies Virus like particles (VLP), Chikungunya VLP, dengue VLP, influenza VLP, Ebola VLP, Zika VLP, Nipah VLP, Hendra VLP, West Nile VLP, Japanese Encephalitis VLP, Chandipura VLP, Hepatitis B VLP, Hepatitis C VLP, Human papilloma VLP, HIV VLP, HIV, haptens, cytokines, non-protein Ags, chimeric proteins, interleukins, snake venom metalloproteinases (SVMPs), phospholipases, snake venom serine proteases, three finger toxins, dendrotoxins, L-amino acid oxidase, cysteine-rich secretory protein (CRISP), C-type lectin-like protein, low molecular mass myotoxin, disintegrins, Hyaluronidase, bacteria, bacterial products, bacterial toxins, bacterial cell surface proteins, bacterial secretory proteins, and combinations thereof.

In an embodiment of the present disclosure, there is provided a method for selecting specific binders against a target molecule using an antibody fragment library as described herein, wherein the target molecule is selected from a group consisting of MTC28, Ag85A, Ag85B, MPT63, MPT64, MPT51, and combinations thereof.

In an embodiment of the present disclosure, there is provided a method for selecting specific binders against a target molecule using an antibody fragment library as described herein, wherein the phage rescue is done using a helper phage.

In an embodiment of the present disclosure, there is provided a method for selecting specific binders against a target molecule using an antibody fragment library as described herein, wherein the phage rescue is done using a helper phage, and wherein the helper phage is selected from a group consisting of AGM13, M13KO7, VCSM13, KM13, Hyperphage, and their derivatives.

In an embodiment of the present disclosure, there is provided a specific binder selected by a method, said method comprising: (i) obtaining an antibody fragment library as described herein; (ii) performing phage rescue from the antibody fragment library using a helper phage to yield phage libraries, wherein the phage libraries represent entire antibody fragment library; (iii) contacting the phage libraries to the target molecule; and (iv) selecting the specific binders against the target molecule.

In an embodiment of the present disclosure, there is provided a method for generating a naïve human antibody fragment library, said method comprising: (a) obtaining a RNA sample from PBMCs of a human subject; (b) obtaining a first strand of cDNA from the RNA sample; (c) amplifying the first strand of cDNA using primers K1-K7 with C1 to yield amplicons comprising Signal sequence*-$V_\kappa$-$C_\kappa$* (*denotes partial sequence of gene encoding Signal sequence or $C_k$) fragments, and purifying the amplicons using non-ethidium bromide based stained gel for visualizing the amplicons using a blue light; (d) amplifying the first strand of cDNA using primers L1-L11 with C2 to yield amplicons comprising Signal sequence*-$V_L$-$C_L$* (*denotes partial sequence of gene encoding Signal sequence or $C_L$) fragments, and purifying the amplicons using non-ethidium bromide based stained gel for visualizing the amplicons using a blue light; (e) amplifying the first strand of cDNA using primers H1-H9 with HuJM32 to yield amplicons comprising L*-$V_H$-M-$C_{H1}$* (*denotes partial sequence of gene encoding Linker or CH1 gene of IgM isotype) fragments, and purifying the amplicons using non-ethidium bromide based stained gel for visualizing the amplicons using a blue light; (f) amplifying the amplicons of step (c) using primers K8-K13 with KS1-KS4 to yield amplicons comprising Signal sequence#-$V_\kappa$-Linker (L)* (#denotes partial sequence of gene encoding Signal sequence longer than step (c) and *denotes partial sequence of gene encoding Linker) fragments, pooling of the 24 amplicons obtained from 28 reactions and purifying the pool of amplicons using non-ethidium bromide based stained gel for visualizing the amplicons using a blue light; (g) amplifying the amplicons of step (d) using primers L12-L22 with LS1-LS3 to yield amplicons comprising Signal sequence #-$V_L$-Linker (L)* (#denotes partial sequence of gene encoding Signal sequence longer than step (d) and *denotes partial sequence of gene encoding Linker) fragments, pooling of all the 33 amplicons, and purifying the pool of amplicons using non-ethidium bromide based stained gel for visualizing the amplicons using a blue light; (h) amplifying the amplicons of step (e) using primers H10-H18 with HuJG-33 to yield amplicons comprising L-L-L-$V_H$-G-$C_{H1}$* (*denotes partial sequence of CH1 gene of IgG isotype) fragments, pooling of all the 9 amplicons, and purifying the pool of amplicons using non-ethidium bromide based stained gel for visualizing the amplicons using a blue light; (i) pooling equimolar concentrations of the amplicons of steps (f) and (h), and performing emulsion-based splicing by Overlap Extension PCR (SOE-ePCR) using primers PelBclo-51 and HuJGclo-34 to obtain spliced scFv comprising #Signal sequence-$V_\kappa$-L-L-L-$V_H$-G-$C_{H1}$* [*denotes partial sequence of gene encoding Signal sequence as in step (f) and *denotes partial sequence of CH1 gene of IgG isotype as in step (h)] fragments, and purifying amplicons using non-ethidium bromide based stained gel for visualizing the amplicons using a blue light; (j) pooling equimolar concentrations of the amplicons of steps (g) and (h), and performing emulsion-based splicing by Overlap Extension PCR (SOE-ePCR) using primers PelBclo-51 and HuJGclo-34 to obtain spliced scFv comprising #Signal sequence-$V_L$-L-L-L-$V_H$-$GC_{H1}$* [#denotes partial sequence of gene encoding Signal sequence as in step (g) and *denotes partial sequence of CH1 gene of IgG isotype as in step (h)] fragments, and purifying amplicons using non-ethidium bromide based stained gel for visualizing the amplicons using a blue light; (k) treatment of spliced scFv of step (i) and (j) with T4 DNA polymerase in the presence of dTTP to generate 4 base 5' overhangs, TGGC at the 5' end and CGCT at the 3' end; (l) digesting pVCHuscFvSacBclo36006 phagemid vector with BsaI restriction enzyme to produce linearized vector with 4 base 5' overhangs, GCCA at the 5' end and AGCG at the 3' end; (m) ligating the scFv products of step (k) individually to BsaI linearized phagemid vector of step (l) to obtain recombinant vector and transforming the recombinant vector in a E. coli cell to obtain the naïve human antibody fragment library, wherein the naïve human antibody fragment library comprises two libraries, and wherein the two libraries consists of a first library comprising scFv of $V_\kappa$-L-L-L-$V_H$ products and a second library comprising scFv of $V_L$-L-L-L-$V_H$ products; and (n) storage of antibody libraries as 16 mini-libraries comprising scFv in $V_\kappa$-L-L-L-$V_H$ format and 20 mini-libraries comprising scFv in $V_L$-L-L-L-$V_H$ format, wherein the signal sequence is PelB, and wherein the method leads to generation of the naïve human antibody fragment library and the library comprises at least 8 billion clones.

Although, the present disclosure discloses a process for preparing the library from RNA (obtained from PBMC) obtained from a single human subject, however, it can be contemplated that similar process can be applied for constructing the library from RNA mixture comprising RNA from more than one human subject.

In an embodiment of the present disclosure, there is provided a method for generating a naïve human antibody fragment library as described herein, wherein the blue light indicates light of wavelength in the range of 470 nm to 490 nm.

In an embodiment of the present disclosure, there is provided a method for generating a naïve human antibody fragment library as described herein, wherein the linker molecule is an amino acid chain ranging from 15-18 amino acids.

In an embodiment of the present disclosure, there is provided a naïve human antibody fragment library obtained by a method, said method comprising: (a) obtaining a RNA sample from PBMCs of a human subject; (b) obtaining a first strand of cDNA from the RNA sample; (c) amplifying the first strand of cDNA using primers K1-K7 with C1 to yield amplicons comprising Signal sequence*-$V_\kappa$-C* (*denotes partial sequence of gene encoding Signal sequence or Ck) fragments, and purifying the amplicons using non-ethidium bromide based stained gel for visualizing the amplicons using a blue light; (d) amplifying the first strand of cDNA using primers L1-L11 with C2 to yield amplicons comprising Signal sequence*-$V_L$-$C_L$* (*denotes partial sequence of gene encoding Signal sequence or $C_L$) fragments, and purifying the amplicons using non-ethidium bromide based stained gel for visualizing the amplicons using a blue light; (e) amplifying the first strand of cDNA using primers H1-H9 with HuJM32 to yield amplicons comprising L*-$V_H$-M-$C_{H1}$* (*denotes partial sequence of gene encoding Linker or CH1 gene of IgM isotype) fragments, and purifying the amplicons using non-ethidium bromide based stained gel for visualizing the amplicons using a blue light; (f) amplifying the amplicons of step (c) using primers K8-K13 with KS1-KS4 to yield amplicons comprising Signal sequence#-$V_\kappa$-Linker (L)* (#denotes partial sequence of gene encoding Signal sequence longer than step (c) and *denotes partial sequence of gene encoding Linker) fragments, pooling of the 24 amplicons obtained from 28 reactions and purifying the pool of amplicons using non-ethidium bromide based stained gel for visualizing the amplicons using a blue light; (g) amplifying the amplicons of step (d) using primers L12-L22 with LS1-LS3 to yield amplicons comprising Signal sequence#-$V_L$-Linker (L)* (#denotes partial sequence of gene encoding Signal sequence longer than step (d) and *denotes partial sequence of gene encoding Linker) fragments, pooling of all the 33 amplicons, and purifying the pool of amplicons using non-ethidium bromide based stained gel for visualizing the amplicons using a blue light; (h) amplifying the amplicons of step (e) using primers H10-H18 with HuJG-33 to yield amplicons comprising L-L-L-$V_H$-G-$C_{H1}$* (*denotes partial sequence of CH1 gene of IgG isotype) fragments, pooling of all the 9 amplicons, and purifying the pool of amplicons using non-ethidium bromide based stained gel for visualizing the amplicons using a blue light; (i) pooling equimolar concentrations of the amplicons of steps (f) and (h), and performing emulsion-based splicing by Overlap Extension PCR (SOE-ePCR) using primers PelBclo-51 and HuJGclo-34 to obtain spliced scFv comprising #Signal sequence-$V_\kappa$-L-L-L-$V_H$-G-$C_{H1}$* [#denotes partial sequence of gene encoding Signal sequence as in step (f) and *denotes partial sequence of CH1 gene of IgG isotype as in step (h)] fragments, and purifying amplicons using non-ethidium bromide based stained gel for visualizing the amplicons using a blue light; (j) pooling equimolar concentrations of the amplicons of steps (g) and (h), and performing emulsion-based splicing by Overlap Extension PCR (SOE-ePCR) using primers PelBclo-51 and HuJGclo-34 to obtain spliced scFv comprising #Signal sequence-$V_L$-L-L-L-$V_H$-$GC_{H1}$* [*denotes partial sequence of gene encoding Signal sequence as in step (g) and *denotes partial sequence of CH1 gene of IgG isotype as in step (h)] fragments, and purifying amplicons using non-ethidium bromide based stained gel for visualizing the amplicons using a blue light; (k) treatment of spliced scFv of step (i) and (j) with T4 DNA polymerase in the presence of dTTP to generate 4 base 5' overhangs, TGGC at the 5' end and CGCT at the 3' end; (l) digesting pVCHuscFvSacBclo36006 phagemid vector with BsaI restriction enzyme to produce linearized vector with 4 base 5' overhangs, GCCA at the 5' end and AGCG at the 3' end; (m) ligating the scFv products of step (k) individually to BsaI linearized phagemid vector of step (1) to obtain recombinant vector and transforming the recombinant vector in a E. coli cell to obtain the naïve human antibody fragment library, wherein the naïve human antibody fragment library comprises two libraries, and wherein the two libraries consists of a first library comprising scFv of $V_\kappa$-L-L-L-$V_H$ products and a second library comprising scFv of $V_L$-L-L-L-$V_H$ products; and (n) storage of antibody libraries as 16 mini-libraries comprising scFv in $V_\kappa$-L-L-L-$V_H$ format and 20 mini-libraries comprising scFv in $V_L$-L-L-L-$V_H$ format, wherein the signal sequence is PelB, and wherein the method leads to generation of the naïve human antibody fragment library and the library comprises at least 8 billion clones.

In an embodiment of the present disclosure, there is provided a method for generating a naïve human antibody fragment library as described herein, wherein the signal sequence is selected from the group consisting of PelB, OmpA, Beta-lactamase, DsbA, gIII, gVIII, PhoA, and their modifications/derivatives.

In an embodiment of the present disclosure, there is provided a method for generating a naïve human antibody library as described herein, wherein the signal sequence is added based on specific primers for respective signal sequence.

In an embodiment of the present disclosure, there is provided a method for isolating specific binders from a naïve human antibody fragment library against a target molecule, said method comprising: (a) obtaining the naïve human antibody fragment library as described herein; (b) performing phage rescue in at least 8 batches and each batch comprising at least 5 mini-libraries from the antibody library using a helper phage to yield phage libraries, wherein the phage libraries represent entire naïve human antibody fragment library and the phage libraries comprise mini-libraries; (c) Pre-adsorption of the antibody displaying phages on streptavidin-coated beads; (d) linking the target molecule to biotin to obtain biotinylated target molecules; and (e) contacting the preadsorbed phage libraries to the biotinylated target molecules, allowing binding between antibody displaying phages and the biotinylated target, followed by the capture of the biotinylated target using streptavidin-coated beads, washing of non-specific phages and elution of specific binders, wherein the method isolates specific binders from the naïve human antibody fragment library.

In an embodiment of the present disclosure, there is provided a method for isolating specific binders from a naïve human antibody fragment library against a target molecule as described herein, wherein the target molecule is selected from the group consisting of Mycobacterium sp. proteins, rabies virus proteins, Chikungunya virus proteins, dengue virus proteins, influenza virus proteins, Ebola virus proteins, Zika virus proteins, Nipah virus proteins, Hendra Virus proteins, West Nile virus proteins, Japanese Encephalitis Virus proteins, Chandipura Virus proteins, Hepatitis B virus proteins, Hepatitis C virus proteins, Human papilloma virus proteins, HIV proteins, snake venom proteins, thyroid hormones, CD20, EGFR (epidermal growth factor receptor), VEGFA (vascular endothelial growth factor A), TNFα (Tumor necrosis factor), CD (Cluster of differentiation)52 CD25, CD3, IgE (Immunoglobulin E), IIb/IIIa integrin receptor, EPO-R (Erythropoietin), G-CSF (granulocyte colony stimulating factor) receptor, GM-CSF receptor, testosterone, β-estradiol, IL-2, BSA (bovine serum albumin), lymphotoxin-β(LT-β), E-selectin ligand-1 (ESL-1), prostate specific antigen, chymotrypsin, human chorio gonadotropin (hCG), enzymes, cell-lines, lysozyme, tetanus toxoid, attenuated rabies virus, Chikungunya virus, dengue virus, influenza virus, Ebola virus, Zika virus, Nipah virus, Hendra Virus, West Nile virus, Japanese Encephalitis Virus, Chandipura Virus, Hepatitis B virus, Hepatitis C virus, Human papilloma virus, HIV, rabies (Virus Like Particle) VLP, Chikungunya VLP, dengue VLP, influenza VLP, Ebola VLP, Zika VLP, Nipah VLP, Hendra VLP, West Nile VLP, Japanese Encephalitis VLP, Chandipura VLP, Hepatitis B VLP, Hepatitis C VLP, Human papilloma VLP, HIV VLP, HIV, haptens, cytokines, non-protein Ags, chimeric proteins, interleukins, snake venom metalloproteinases (SVMPs), phospholipases, snake venom serine proteases, three finger toxins, dendrotoxins, L-amino acid oxidase, cysteine-rich secretory protein (CRISP), C-type lectin-like protein, low molecular mass myotoxin, disintegrins, Hyaluronidase, bacteria, bacterial products, bacterial toxins, bacterial cell surface proteins, bacterial secretory proteins, and combinations thereof.

In an embodiment of the present disclosure, there is provided a method for isolating specific binders from a naïve human antibody fragment library against a target molecule as described herein, wherein the target molecule is selected from a group consisting of MTC28, Ag85A, Ag85B, MPT63, MPT64, MPT51, MTBLIB42C02-F1, MTBLIB42C02-F2, MTBLIB42C02-F4, MTBLIB42C02-F6, MTBLIB42C02-F7, MTBLIB42C02-F8, MTBLIB42C02-F10, MTBLIB42C02-F11, MTBLIB42C02-F12, and combinations thereof.

In an embodiment of the present disclosure, there is provided a method for isolating specific binders from a naïve human antibody fragment library against a target molecule as described herein, wherein the non-ethidium bromide based gel staining is done using a dye selected from the group consisting of SYBR Safe stain, SYBR gold, SYBR green, Gel-green, GelStar, SafeView stain, EZ-VISION® Blue Light DNA Dye, and Midori Green.

In an embodiment of the present disclosure, there is provided a specific binder isolated from the naïve human antibody fragment library using a method, said method comprising: (a) obtaining the naïve human antibody fragment library as described herein; (b) performing phage rescue in at least 8 batches and each batch comprising at least 5 mini-libraries from the antibody library using a helper phage to yield phage libraries, wherein the phage libraries represent entire naïve human antibody fragment library and the phage libraries comprise mini-libraries; (c) Pre-adsorption of the antibody displaying phages on streptavidin-coated beads; (d) linking the target molecule to biotin to obtain biotinylated target molecules; and (e) contacting the preadsorbed phage libraries to the biotinylated target molecules, allowing binding between antibody displaying phages and the biotinylated target, followed by the capture of the biotinylated target using streptavidin-coated beads, washing of non-specific phages and elution of specific binders, wherein the method isolates specific binders from the naïve human antibody fragment library.

In an embodiment of the present disclosure, there is provided a specific binder isolated from the naïve human antibody fragment library using a method as described herein, wherein the antibody displaying phages can be selected on targets, passively coated on solid surfaces. It is intended to depict that the process as described herein can be performed without the need of biotin-streptavidin chemistry or without the use of any directional cloning.

In an embodiment of the present disclosure, there is provided a use of emulsion-based PCR in constructing antibody fragment library, wherein the antibody fragment library is either naïve or immunized library.

In an embodiment of the present disclosure, there is provided a use of emulsion-based PCR in constructing either a semi-synthetic or synthetic antibody fragment library.

In an embodiment of the present disclosure, there is provided a use of restriction enzyme-free insert preparation in constructing antibody fragment library, wherein the antibody fragment library is either naïve or immunized library.

In an embodiment of the present disclosure, there is provided a use of restriction enzyme-free insert preparation in constructing either a semi-synthetic or synthetic antibody fragment library.

In an embodiment of the present disclosure, there is provided a use of emulsion-based PCR in constructing human antibody fragment library, wherein the antibody fragment library is either naïve or immunized library.

In an embodiment of the present disclosure, there is provided a use of emulsion-based PCR in amplification of $V_L$ and $V_H$ gene and splicing of $V_L$ and $V_H$ gene.

In an embodiment of the present disclosure, there is provided a use of T4 DNA polymerase in constructing the antibody fragment library as described herein.

In an embodiment of the present disclosure, there is provided a use of Klenow fragment of DNA polymerase in constructing the antibody fragment library as described herein.

In an embodiment of the present disclosure, there is provided a use of TOP 10F' cells in obtaining the antibody fragment library as described herein.

In an embodiment of the present disclosure, there is provided a use of TG1 cells in obtaining the antibody fragment library as described herein.

In an embodiment of the present disclosure, there is provided a use of XL-1 Blue cells in obtaining the antibody fragment library as described herein.

In an embodiment of the present disclosure, there is provided an antibody fragment library as described in the present disclosure, wherein the antibody fragment library is devoid of short clones.

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

While the invention is broadly as defined above, it will be appreciated by those persons skilled in the art that it is not limited thereto and that it also includes embodiments of which the following description gives examples.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

The described Examples 1-2 depicts the method generating a naïve human antibody gene library. The Examples 3-8 describes the characterization of the library. Next-generation sequencing has been employed to characterize the library at genome-scale. A streamlined protocol has been optimized for the production of six highly pure biotinylated mycobacterial proteins carrying single biotin residue at the C-terminus via 15 amino acid biotin acceptor peptide tag, which have been employed as a bait for the isolation of specific binders during in-solution affinity selection. The library has successfully yielded a diverse range of binders against all the six target mycobacterial proteins and is expected to serve as an important source of human monoclonal antibodies against targets of interest.

Example 1

Amplification and assembly of variable genes of human antibody repertoire
Materials Used:
Phagemid Vector pVCHuscFvcloSacB36006 carries under the control of lacPO between HindIII and EcoRI sites, a DNA cassette comprising XbaI site, ribosome binding site (RBS), first 15 amino acids of Pectate lysase B signal sequence (PelBss), approximately 2.0 kb cassette encoding for SacB gene flanked by two BsaI restriction sites in appropriate orientation followed by codons for trypsin cleavage site (KDIR) and full length gIII (2-405 amino acid residues) with codons optimized for improved expression in *E. coli*, and appropriate spacers comprising glycine and serine residues. The vector backbone comprises the phage origin of replication (F+), beta-lactamase gene as a selection marker, and ColE1 ori. The scFv gene fragments are cloned in place of the 2.0 kb SacB stuffer using a restriction enzyme-free cloning strategy.

Strains, Enzymes and Chemicals

*Escherichia coli* strains TOP10F' (F' [lacI$^q$ Tn10 (letR)] mcrA Δ(mrr-hsdRMS-mcrBC) φ80lacZΔM15 ΔlacX74 deoR nupG recA1 araD139 Δ(ara-leu)7697 galU galK rpsL (Str$^R$) endA1 λ$^-$) was obtained from commercial sources. MAb 2911 and 30421 are monoclonal antibodies reactive against the gVIIIp and gIIIp coat protein of M13 phage (Bhardwaj, D., et al., (1995). "Monoclonal antibodies against a minor and the major coat proteins of filamentous phage M13: their application in phage display." J Immunol Methods 179(2): 165-75). Expand Long template PCR system and T4 DNA Ligase was obtained from Roche, Mannheim, Germany. SuperScript III First-Strand Synthesis System, SYBR Safe DNA gel stain and Safe Imager™ Blue-Light Transilluminator were obtained from Life Technologies, Regensburg, Germany. Reagents for emulsion PCR, Span 80, Triton X-100, Tween 80, mineral oil and diethyl ether were obtained from Sigma-Aldrich. All standard chemicals were obtained from Affymetrix, CA, USA. HPLC-purified primers used for antibody variable gene amplifications were obtained from IBA GmbH, Goettingen, Germany or Sigma-Aldrich, Bangalore, India. Restriction enzymes and T4 DNA polymerase was obtained from NEB, Ipswich, Mass., USA. Six *M. tuberculosis* proteins viz. MTC28, MPT63, MPT64, Ag85A, Ag85B, MPT51 were expressed in *E. coli* host BL21(DE3) RIL and purified by three step chromatography as C-terminal BAP tagged proteins and biotinylated in vitro using recombinant H10-BirA enzyme (Indian Patent Application No. 201711040047)

Lymphoid tissue and RNA

As a source of antibody genes, PBMCs (Peripheral Blood Mononuclear Cells), were taken from individuals who were tested negative for common infectious agents including HBsAg, HBcAb, HCV, HTLV I/II and STS by serology; as well as HIV I, HCV and WNV by NAT. A total of approximately $1.1 \times 10^9$ (~1100 million) PBMCs from 10 such individuals were used for RNA preparation using modified RNeasy (Qiagen) method.

Methods Employed for Amplification and Assembly of Variable 2Ene Pool of Human Antibody Repertoire PCR Reactions Random primed cDNA was synthesized using 48 µg of Total RNA using SuperScript III First-Strand Synthesis System (Life technologies) as per manufacturer's protocol. Oligonucleotides used for amplification of variable light and heavy genes $\{V_K/V_L$ and $V_H\}$ covering almost all the families of human antibody repertoire have been described in Table 1.

TABLE 1

Sequences of primers used for construction of Human naive scFv library

| S. No. | Primer name | Primer sequence (5' → 3') |
|---|---|---|
| A. VK5' sense primers (5' → 3') | | |
| K1 (SEQ ID NO: 1) | HuVK11-51 | GCTGACATCCAGATGACCCAGTCTCC |
| K2 (SEQ ID NO: 2) | HuVK12-51 | GCTGMCATCCRGWTGACCCAGTCTCC |
| K3 (SEQ ID NO: 3) | HuVK2-51 | GCTGATRTTGTGATGACYCAGWCTCC |
| K4 (SEQ ID NO: 4) | HuVK3-51 | GCTGAAATWGTGWTGACRCAGTCTCC |
| K5 (SEQ ID NO: 5) | HuVK4-51 | GCTGACATCGTGATGACCCAGTCTCC |
| K6 (SEQ ID NO: 6) | HuVK5-51 | GCTGAAACGACACTCACGCAGTCTCC |
| K7 (SEQ ID NO: 7) | HuVK6-51 | GCTGAWRTTGTGMTGACWCAGTCTCC |
| B. VK5' sense primers with PelBss extension (5' → 3') | | |
| K8 (SEQ ID NO: 8) | HuVK11-52 | TGGCAGCTCAGCCAGCGATGGCTG ACATCCAGATGACCCAGTCTCC |
| K9 (SEQ ID NO: 9) | HuVK12-52 | TGGCAGCTCAGCCAGCGATGGCTG MCATCCRGWTGACCCAGTCTCC |
| K10 (SEQ ID NO: 10) | HuVK2-52 | TGGCAGCTCAGCCAGCGATGGCTG ATRTTGTGATGACYCAGWCTCC |

TABLE 1-continued

Sequences of primers used for construction of Human naive scFv library

| S. No. | Primer name | Primer sequence (5' → 3') |
|---|---|---|
| K11 (SEQ ID NO: 11) | HuVK3-52 | TGGCAGCTCAGCCAGCGATGGCTGAAATWGTGWTGACRCAGTCTCC |
| K12 (SEQ ID NO: 12) | HuVK4-52 | TGGCAGCTCAGCCAGCGATGGCTGACATCGTGATGACCCAGTCTCC |
| K13 (SEQ ID NO: 13) | HuVK5-52 | TGGCAGCTCAGCCAGCGATGGCTGAAACGACACTCACGCAGTCTCC |
| K14 (SEQ ID NO: 14) | HuVK6-52 | TGGCAGCTCAGCCAGCGATGGCTGAWRTTGTGMTGACWCAGTCTCC |

C. VK3' reverse primers (5' → 3')

| C1 (SEQ ID NO: 15) | HuCK-31 | GATGAAGACAGATGGTGCAGCCACAGT |
| KS1 (SEQ ID NO: 39) | HuscFvJK140-31 | ACCGCCACCGGATCCACCCCCACCTTTGATYTCCACCTTGGTCCC |
| KS2 (SEQ ID NO: 40) | HuscFvJK20-31 | ACCGCCACCGGATCCACCCCCACCTTTGATCTCCAGCTTGGTCCC |
| KS3 (SEQ ID NO: 41) | HuscFvJK30-31 | ACCGCCACCGGATCCACCCCCACCTTTGATATCCACTTTGGTCCC |
| KS4 (SEQ ID NO: 42) | HuscFvJK50-31 | ACCGCCACCGGATCCACCCCCACCTTTAATCTCCAGTCGTGTCCC |

D. VL5' sense primers (5' → 3')

| L1 (SEQ ID NO: 16) | HuVL11-51 | GCTCAGTCTGTGYTGACGCAGCCGCC |
| L2 (SEQ ID NO: 17) | HuVL12-51 | GCTCAGTCTGTGCTGACTCAGCCACC |
| L3 (SEQ ID NO: 18) | HuVL2-51 | GCTCAGTCTGCCCTGACTCAGCCT |
| L4 (SEQ ID NO: 19) | HuVL31-51 | GCTTCCTATGWGCTGACWCAGCCACC |
| L5 (SEQ ID NO: 20) | HuVL32-51 | GCTTCTTCTGAGCTGACTCAGGACCC |
| L6 (SEQ ID NO: 21) | HuVL41-51 | GCTCTGCCTGTGCTGACTCAGCCC |
| L7 (SEQ ID NO: 22) | HuVL42-51 | GCTCAGCYTGTGCTGACTCAATCRYC |
| L8 (SEQ ID NO: 23) | HuVL5-51 | GCTCAGSCTGTGCTGACTCAGCC |
| L9 (SEQ ID NO: 24) | HuVL6-51 | GCTAATTTTATGCTGACTCAGCCCCA |
| L10 (SEQ ID NO: 25) | HuVL7/8-51 | GCTCAGRCTGTGGTGACYCAGGAGCC |
| L11 (SEQ ID NO: 26) | HuVL9/10-51 | GCTCAGSCWGKGCTGACTCAGCCACC |

E. VL5' sense primers with PelBss extension (5' → 3')

| L12 (SEQ ID NO: 27) | HuVL11-52 | TGGCAGCTCAGCCAGCGATGGCTCAGTCTGTGYTGACGCAGCCGCC |
| L13 (SEQ ID NO: 28) | HuVL12-52 | TGGCAGCTCAGCCAGCGATGGCTCAGTCTGTGCTGACTCAGCCACC |
| L14 (SEQ ID NO: 29) | HuVL2-52 | TGGCAGCTCAGCCAGCGATGGCTCAGTCTGCCCTGACTCAGCCT |
| L15 (SEQ ID NO: 30) | HuVL31-52 | TGGCAGCTCAGCCAGCGATGGCTTCCTATGWGCTGACWCAGCCACC |
| L16 (SEQ ID NO: 31) | HuVL32-52 | TGGCAGCTCAGCCAGCGATGGCTTCTTCTGAGCTGACTCAGGACCC |
| L17 (SEQ ID NO: 32) | HuVL41-52 | TGGCAGCTCAGCCAGCGATGGCTCTGCCTGTGCTGACTCAGCCC |
| L18 (SEQ ID NO: 33) | HuVL42-52 | TGGCAGCTCAGCCAGCGATGGCTCAGCYTGTGCTGACTCAATCRYC |
| L19 (SEQ ID NO: 34) | HuVL5-52 | TGGCAGCTCAGCCAGCGATGGCTCAGSCTGTGCTGACTCAGCC |
| L20 (SEQ ID NO: 35) | HuVL6-52 | TGGCAGCTCAGCCAGCGATGGCTAATTTTATGCTGACTCAGCCCCA |
| L21 (SEQ ID NO: 36) | HuVL7/8-52 | TGGCAGCTCAGCCAGCGATGGCTCAGRCTGTGGTGACYCAGGAGCC |
| L22 (SEQ ID NO: 37) | HuVL9/10-52 | TGGCAGCTCAGCCAGCGATGGCTCAGSCWGKGCTGACTCAGCCACC |

F. VL3' reverse primers (5' → 3')

| C2 (SEQ ID NO: 38) | HuCL-31 | GACCGAGGGGGCAGCCTTGGGCTGACC |
| LS1 (SEQ ID NO: 43) | HuscFvJL1236-31 | ACCGCCACCGGATCCACCCCCACCTAGGACGGTCASCTTGGTSCC |
| LS2 (SEQ ID NO: 44) | HuscFvJL4-31 | ACCGCCACCGGATCCACCCCCACCTAAAATGATCAGCTGGGTTCC |

TABLE 1-continued

Sequences of primers used for construction of Human naive scFv library

| S. No. | Primer name | Primer sequence (5' → 3') |
|---|---|---|
| LS3 (SEQ ID NO: 45) | HuscFvJL57-31 | ACCGCCACCGGATCCACCCCCACCG AGGACGGTCAGCTSGGTSCC |

G. VH5' sense primers (5' → 3')

| S. No. | Primer name | Primer sequence (5' → 3') |
|---|---|---|
| H1 (SEQ ID NO: 46) | HuscFvVH1-51 | GGAAGCCAGGTBCAGCTGGTGCAG TCTGG |
| H2 (SEQ ID NO: 47) | HuscFvVH1/7-51 | GGAAGCCARRTSCAGCTGGTRCART CTGG |
| H3 (SEQ ID NO: 48) | HuscFvVH2-51 | GGAAGCCAGRTCACCTTGAAGGAG TCTGG |
| H4 (SEQ ID NO: 49) | HuscFvVH31-51 | GGAAGCSARGTGCAGCTGGTGCAGT CTGG |
| H5 (SEQ ID NO: 50) | HuscFvVH32-51 | GGAAGCGAGGTGCAGCTGKTGGAG WCYSG |
| H6 (SEQ ID NO: 51) | HuscFvVH41-51 | GGAAGCCAGGTGCARCTGCAGGAG TCGGG |
| H7 (SEQ ID NO: 52) | HuscFvVH42-51 | GGAAGCCAGSTGCAGCTRCAGSAGT SSGG |
| H8 (SEQ ID NO: 53) | HuscFvVH5-51 | GGAAGCGARGTGCAGCTGGTGCAG TCTGG |
| H9 (SEQ ID NO: 54) | HuscFvVH6-51 | GGAAGCCAGGTACAGCTGCAGCAG TCAGG |

H. VH5' sense primers with linker extension (5' → 3')

| S. No. | Primer name | Primer sequence (5' → 3') |
|---|---|---|
| H10 (SEQ ID NO: 55) | HuscFvVH1-52 | GGTGGGGGTGGATCCGGTGGCGGT GGCTCTGGAGGCGGTGGAAGCCAG GTBCAGCTGGTGCAGTCTGG |
| H11 (SEQ ID NO: 56) | HuscFvVH1/7-52 | GGTGGGGGTGGATCCGGTGGCGGT GGCTCTGGAGGCGGTGGAAGCCAR RTSCAGCTGGTRCARTCTGG |
| H12 (SEQ ID NO: 57) | HuscFvVH2-52 | GGTGGGGGTGGATCCGGTGGCGGT GGCTCTGGAGGCGGTGGAAGCCAG RTCACCTTGAAGGAGTCTGG |
| H13 (SEQ ID NO: 58) | HuscFvVH31-52 | GGTGGGGGTGGATCCGGTGGCGGT GGCTCTGGAGGCGGTGGAAGCSAR GTGCAGCTGGTGCAGTCTGG |
| H14 (SEQ ID NO: 59) | HuscFvVH32-52 | GGTGGGGGTGGATCCGGTGGCGGT GGCTCTGGAGGCGGTGGAAGCGAG GTGCAGCTGKTGGAGWCYSG |
| H15 (SEQ ID NO: 60) | HuscFvVH41-52 | GGTGGGGGTGGATCCGGTGGCGGT GGCTCTGGAGGCGGTGGAAGCCAG GTGCARCTGCAGGAGTCGGG |
| H16 (SEQ ID NO: 61) | HuscFvVH42-52 | GGTGGGGGTGGATCCGGTGGCGGT GGCTCTGGAGGCGGTGGAAGCCAG STGCAGCTRCAGSAGTSSGG |
| H17 (SEQ ID NO: 62) | HuscFvVH5-52 | GGTGGGGGTGGATCCGGTGGCGGT GGCTCTGGAGGCGGTGGAAGCGAR GTGCAGCTGGTGCAGTCTGG |
| H18 (SEQ ID NO: 63) | HuscFvVH6-52 | GGTGGGGGTGGATCCGGTGGCGGT GGCTCTGGAGGCGGTGGAAGCCAG GTACAGCTGCAGCAGTCAGG |

I. VH3' reverse (5' → 3')

| S. No. | Primer name | Primer sequence (5' → 3') |
|---|---|---|
| SEQ ID NO: 64 | HuJM-32 | GGGGCGGATGCACTCCCTGAGGAG ACGGTGACC |
| SEQ ID NO: 65 | HuJG-33 | GGGCCCTTTGTACTCGCTGAGGAGA CGGTGACC |

J. Primers for final splicing (5' → 3')

| S. No. | Primer name | Primer sequence (5' → 3') |
|---|---|---|
| SEQ ID NO: 66 | PelBclo-51 | TGGCAGCTCAGCCAGCGATGGCT |
| SEQ ID NO: 67 | HuJGclo-34 | CGCTAGGGCCCTTTGTACTCGCTGA GGAGAC |

First Step of PCR Reactions

Figure 1:
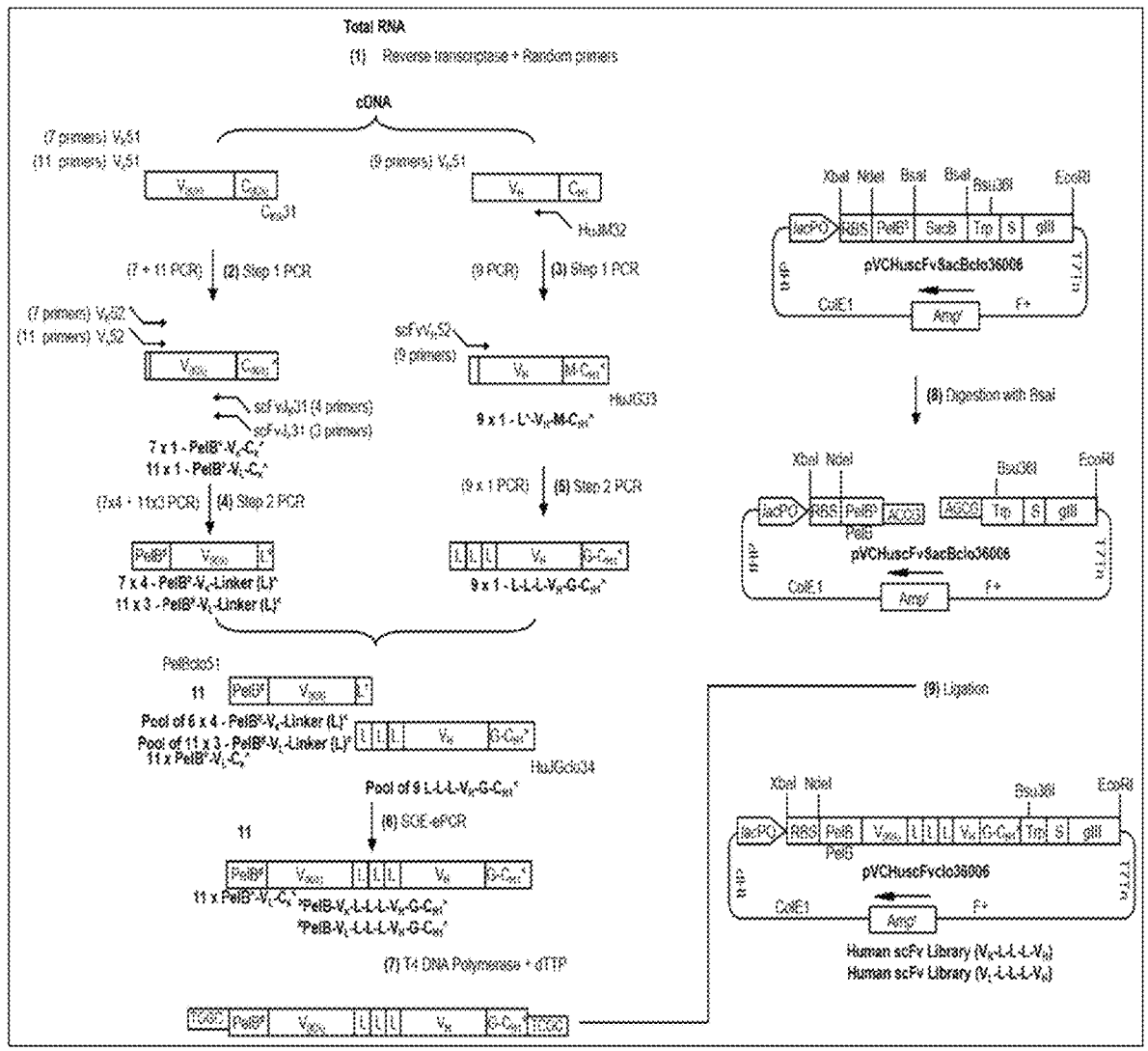

Variable genes were amplified using two-step PCR described in FIG. 1. The primers are referred to by their names and correspond to the S. No. as mentioned in the Table 1. A detailed listing of the primers has been mentioned in the sequence listing. For first step of PCR, 27 reactions were set up for amplification of $V_K/V_L$ and $V_H$ antibody repertoire. Each first step PCR was performed using Expand long template PCR system (Roche) in total reaction volume of 40 μl, containing 4 μl of cDNA (equivalent to 1.6 μg total RNA) as template and 20 pmoles each of the forward and reverse primers, 200 μM dNTPs with initial heating at 95° C. for 3 min followed by 30 cycles of denaturation at 95° C. for 30 sec, annealing at 55° C. for 30 sec and polymerization at 68° C. for 30 sec with 2 sec extension in each cycle. Final polymerization was carried out at 68° C. for 5 min. The PCR products were purified by SYBR Safe stained-agarose gel based extraction, using QIAquick gel extraction kit (Qiagen, Hilden, Germany) and eluted in 60 μl EB. Individual 27 PCR products obtained from first reaction were used as template for second step PCR, to add respective cloning sites on 5' and 3' ends.

Referring to FIG. 1, First strand cDNA (randomly primed) was synthesized from the total RNA of PBMCs obtained from naïve individuals (1). First step PCR to amplify antibody variable light chain genes was performed using 7 forward Vk-51 primers and 1 reverse Ck-31 primer to obtain 7 PelB*-$V_K$-$C_K$* amplicons (*denotes partial sequence of gene encoding PelB or $C_k$), and using 11 forward VL-51 primers and 1 reverse CL-31 primer to obtain 11 PelB*-$V_L$-$C_K$* amplicons (*denotes partial sequence of gene encoding PelB or $C_k$) (2). Similarly, first step PCR to amplify antibody variable heavy chain genes was performed using 9 forward VH-51 primers and 1 reverse HuJM-32 primer to obtain 9 L*-$V_H$-$C_{H1}$* amplicons (*denotes partial sequence of gene encoding Linker or CH1 gene of IgM isotype) (3). The first-step PCR amplicons were purified from non-ethidium bromide-stained gel for visualizing the amplicons using a blue light. The purified first-step amplicons were used as template for second-step PCR.

Second Step of PCR Reactions

For second step of PCR, 70 reactions (FIG. 1) were set up using Expand long template PCR system with 5 ng each of purified first step PCR products in a total reaction volume of 50 μl containing 25 pmoles each of the forward and reverse primers and 200 μM dNTPs with initial heating at 95° C. for 3 min followed by 25 cycles of denaturation at 95° C. for 30 sec, annealing at 55° C. for 30 sec and polymerization at 68° C. for 30 sec with 2 sec extension in each cycle. Final polymerization was carried out at 68° C. for 5 min.

Second step PCR products obtained from 24/28 reactions for $V_K$, 33 reactions for $V_L$ and 9/9 reactions for $V_H$ (total 66) were pooled separately and purified by SYBR Safe stained-agarose gel based extraction using QIAquick gel extraction kit and eluted in total volume of 60 μl.

Referring to FIG. 1, in second-step of PCR, variable kappa light chains were amplified using 6 forward VK-52 primers and 4 scFv-JK-31 primers to obtain 24 (6×4) PelB-$V_K$-Linker (L)* (#denotes partial sequence of gene encoding PelB and *denotes partial sequence of gene encoding Linker) amplicons, and variable lambda light chains were amplified using 11 forward VL-52 primers and 3 scFv-JL-31 primers to obtain 33 (11×3) PelB#-$V_L$-Linker (L)* amplicons (4). Similarly, second-step PCR to amplify antibody variable heavy chain genes was performed using 9 forward $V_H$-52 primers and 1 reverse HuJG-33 primer to obtain 9 L-L-L-$V_H$-G-$C_{H1}$* amplicons (*denotes partial sequence of CH1 gene of IgG isotype) (5). The respective kappa, lambda and heavy chain amplicons from second-step PCR were pooled and purified from non-ethidium bromide-stained gel for visualizing the amplicons using a blue light.

Emulsion-based Splicing by Overlap Extension-PCR (SOE-ePCR)

$V_K/V_L$ and $V_H$ genes were assembled using emulsion-based Splicing by Overlap Extension-PCR (SOE-ePCR). For initial optimizations, three different template concentrations were employed. Equimolar mix of gel purified $V_K/V_L$ and $V_H$ was prepared and diluted to a concentration of 1 ng/μl. Of this 2, 3, and 4 μl (equivalent to 2, 3 and 4 ng of variable genes) was used for setup of SOE-ePCR reaction for 25, 30 and 35 cycles of PCR. The reaction was setup in a volume of 260 μl containing 20 U Expand long template enzyme blend, 78 pmoles each of forward and reverse primers PelBclo51 and HuJGClo34, respectively, 200 μM dNTPs and 2.6 mg BSA with appropriate volumes of the template. Of this, 200 μl was emulsified in 400 μl oil-surfactant mix (Williams, R. S. G. Peisajovich, O. J. Miller, S. Magdassi, D. S. Tawfik and A. D. Griffiths (2006), "Amplification of complex gene libraries by emulsion PCR." Nat Methods 3(7):540-50). The emulsion was distributed in 50 μl aliquots and overlaid with mineral oil and subjected to initial heating at 95° C. for 3 min followed by 25, 30 or 35 cycles of denaturation at 95° C. for 30 sec, annealing at 55° C. for 30 sec and polymerization at 68° C. for 30 sec in each cycle. Final polymerization was carried out at 68° C. for 5 min. The emulsified product was purified using extraction with diethyl ether followed by concentration using QIAquick PCR purification kit (Qiagen, Hilden, Germany). Simultaneously, conventional PCR was setup under same conditions with the remaining 60 μl PCR mix. An aliquot was analyzed on 1.2% agarose gel to estimate the quality of the spliced scFv fragments.

Referring to FIG. 1, Equimolar concentrations of the second step PCR kappa amplicon pool PelB#-$V_K$-Linker (L)* and heavy chain amplicon pool L-L-L-$V_H$-G-$C_{H1}$*, [#denotes partial sequence of gene encoding PelB and *denotes partial sequence of CH1 gene of IgG isotype] or equimolar concentrations of the second step PCR lambda amplicon pool PelB#-$V_L$-Linker (L)* and heavy chain amplicon pool L-L-L-$V_H$-G-$C_{H1}$*, were mixed and subjected to emulsion-based splicing by Overlap Extension PCR (SOE-ePCR) using primers PelBclo-51 and HuJGclo-34 to obtain spliced scFv comprising #PelB-$V_K$-L-L-L-$V_H$-G-$C_{H1}$* or #PelB-$V_L$-L-L-L-$V_H$-G-$C_{H1}$* (6). The spliced scFv DNA were purified from non-ethidium bromide-stained gel for visualizing the amplicons using a blue light and treated with T4 DNA polymerase in presence of dTTP to generate 4 base 5' overhangs, TGGC at the 5' end and CGCT at the 3' end (7). The phagemid vector pVCHus-cFvSacBclo36006 was digested with BsaI restriction enzyme to produce linearized vector with 4 base 5' overhangs, GCCA at the 5' end and AGCG at the 3' end (8). The treated scFv DNA from step (7) were ligated individually to BsaI linearized phagemid vector to obtain the recombinants for two naïve human antibody fragment libraries, comprising scFv of $V_K$-L-L-L-$V_H$ products and a second library comprising scFv of $V_L$-L-L-L-$V_H$ products (9).

For preparative scale SOE-ePCR to obtain ~10 μg spliced products viz. $V_K$-linker-$V_H$ and $V_L$-linker-$V_H$, the above described aqueous reaction was scaled up to 1040 μl under optimized conditions and additional cleanup was performed using SYBR Safe stained-agarose gel based extraction with QIAquick gel extraction kit.

Results Obtained

Amplification of Variable Genes of Human Antibody Repertoire

Total RNA was obtained from PBMCs of 10 healthy human donors tested negative for common infectious pathogens. cDNA was synthesized using random hexamers and used as a template for amplification of the variable genes from human antibody repertoire represented in the PBMCs. A total of 67 oligonucleotides were designed for amplification to ensure coverage of almost all the antibody gene families.

Variable genes were amplified using two-step PCR, followed by their assembly using emulsion-based Splicing by Overlap Extension PCR (SOE-ePCR) as described in FIG. 1. It should be noted, that at every amplification step or assembly, sufficient numbers of DNA molecules were taken in the reaction to ensure maintenance of the variability/diversity in the library.

Primers used for amplification have been mentioned in Table 1.

Figure 2:
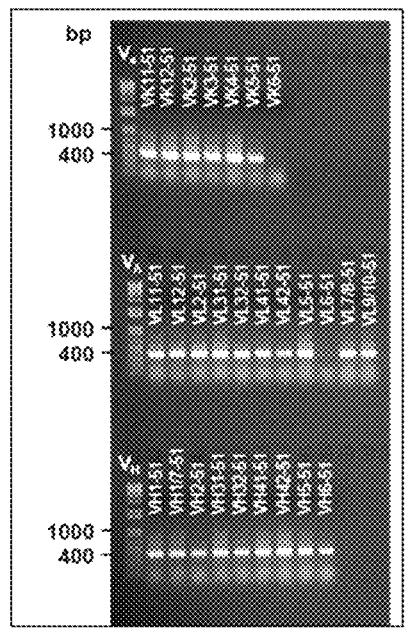
FIG. 2 depicts the amplification results of first step of PCR, in accordance with an embodiment of the present disclosure.

During first step PCR (FIG. 1), a total of 27 PCRs were setup wherein, $V_K$ was amplified using seven 5' and one 3' primers, $V_L$ using eleven 5' and one 3' primers and $V_H$ using nine 5' primers and one 3' primer HuJM-32 located in the first constant domain of IgM isotype to amplify naïve VH segments. As can be inferred from FIG. 2, all primers except HuVK6-51 works whereas primer HuVL6-51 gives poor amplification. The analysis of coverage by HuVK6-51 primer revealed that gene families amplified by this could also be amplified by rest of the primers. Irrespective of amplification, the PCR products were purified and used as template for second step PCR.

Figure 3:
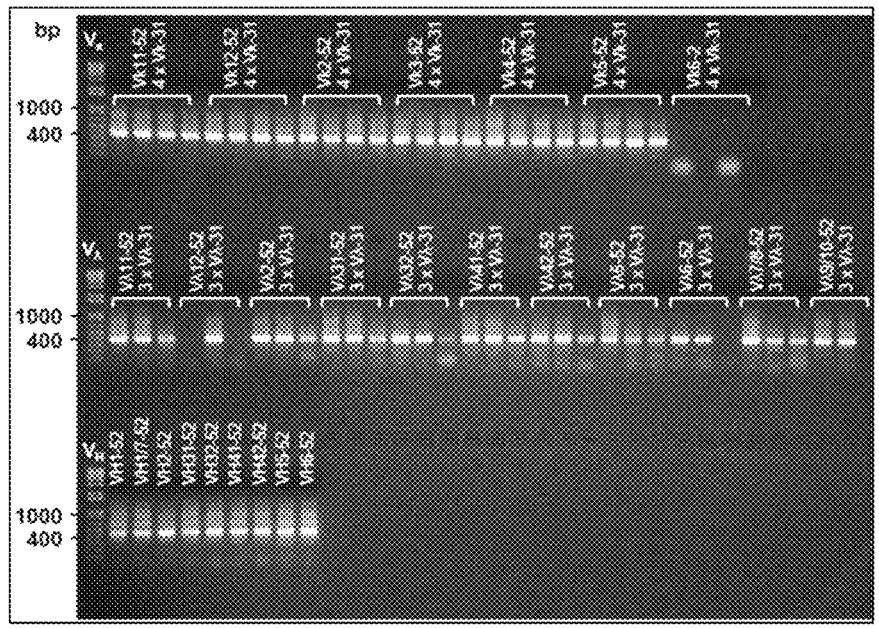
FIG. 3 depicts the amplification results of second step of PCR, in accordance with an embodiment of the present disclosure.

For second PCR (FIG. 1), a total of 70 reactions were setup using first step PCR products as template. From FIG. 3, it can be inferred that $V_K$ is amplified in 28 reactions using seven 5'-VK-52 primers (corresponding to seven VK-51 with an extension of additional 20 bases encoding last 7 codons of PelB signal sequence), and four 3'-J region specific primers (HuscFvJK-31). $V_L$ is amplified in total 33 reactions using eleven 5'-VL-52 primers (corresponding to eleven VL-51 with an extension of additional 20 bases encoding last 7 codons of PelB signal sequence) with three 3'-J region (chain) specific primers (scFvJL-31). $V_H$ is amplified in 9 reactions, using nine 5' VH-52 primers (corresponding to VH-51 with an extension of additional 39 bases encoding for the linker region) with 3' primer HuJG-33.

24/28 $V_K$ and 9 $V_H$ reactions show good amplifications. Although, most of the reactions for $V_L$ amplification worked, a few of the primers did not lead to efficient amplifications. However, all primers should not amplify to equal extent and amount amplified would depend on the template concentration carrying sequence corresponding to that J region.

Assembly of Variable Gene Fragments to Produce scFv Fragments Using SOE-ePCR

For assembly of scFv fragment, variable light chain gene was spliced to variable heavy chain gene in $V_{Light}$-$V_{Heavy}$ format with a 15-amino acid linker encoding glycine-serine residues, separating the two domains. The primers HuPelB-clo51 and HuJGclo34 primers anneal to PelB and CH1 sequences respectively, already appended during second PCR. These primers do not add these sequences at this stage. To obtain kappa and lambda libraries containing scFv fragments encoding $V_K$-Linker-$V_H$ and $V_L$-Linker-$V_H$, 2 different splicing reactions were set up using purified second step PCR products as template in a conventional Splicing by Overlap Extension-PCR (SOE-ePCR). However, during splicing of $V_K/V_L$ and $V_H$, significant amount of smearing and non-specific amplification was observed (FIG. 4A).

Hence, emulsion-based PCR (ePCR) was optimized for splicing of variable genes to obtain scFv preparations that are as clean and pure as any regular PCR product obtained in a standard laboratory. An oil-surfactant mixture comprising SPAN-80 (4.5% v/v), Tween-80 (0.4% v/v) and Triton X-100 (0.05% v/v) in mineral oil was prepared and used for emulsification of the aqueous PCR. The emulsified reaction was then subjected to thermo-cycling under appropriate conditions. Initially, splicing of variable genes was performed using 3 concentrations of the equimolar mix of purified second step PCR products $V_K/V_L$ and $V_H$ for 25, 30 and 35 cycles of PCR. Simultaneously, conventional PCR was setup under same conditions. SOE-ePCR led to clean and distinct band of the desired spliced product up to 35 cycles of PCR with a template concentration of 2 ng (FIG. 4B; Lane 3). Whereas, conventional PCR showed completely smeared product with non-specific amplification even at the lowest template concentration and number of PCR cycles (FIG. 4A; Lane 1-9). Based on the results of analytical SOE-ePCR, preparatory scale production of spliced scFv was performed for both $V_K$-$V_H$ and $V_H$-$V_L$, using 2 ng equimolar template mix/260 ul aqueous PCR and 35 cycles of PCR.~10 µg spliced $V_K$-$V_H$ (FIG. 4C) and $V_H$-$V_L$ (FIG. 4D) product was obtained from SOE-ePCR performed with 1040 µl aqueous PCR each.

Example 2

Construction of Naïve Human scFv Library in Phagemid Based Phage Display Vector

Method Used:

The spliced products (as described in Example 1), $V_K$-linker-$V_H$ and $V_L$-linker-$V_H$ were treated with T4 DNA polymerase under controlled conditions to obtain scFv fragments with non-compatible, non-palindromic 4 base long 5' overhangs TGGC and CGCT at 5' and 3' ends respectively. Briefly, 5 µg each of gel-purified $V_K$-linker-$V_H$ and $V_L$-linker-$V_H$ spliced products were treated with 4.5 U of T4 DNA polymerase in 1×NEB 2 buffer in a reaction volume of 100 µl in the presence of 500 µM dTTP and 100 µg/ml BSA at 15° C. for 60 min followed by purification using QIAquick PCR purification kit.

Phagemid based phage display vector pVCHuscFv-cloSacB36006, for cloning of scFv fragments was prepared by digesting ~20 µg plasmid DNA with 200 units of BsaI-HF in a total volume of 400 µl at 37° C. for 3 hrs. The digested DNA was purified using phenol: chloroform extraction followed by ethanol precipitation in presence of sodium acetate and pellet was re-suspended in 0.1×TE. The DNA was then resolved on 1.2% Sea Plaque GTG agarose (Lonza, Rockland, Me., USA) for purification of the linearized vector containing insert compatible 4-base 5' overhangs using the Qiaquick Gel Extraction kit.

Finally, preparative scale ligation was setup for construction of two libraries comprising scFv fragments $V_K$-linker-$V_H$ and $V_L$-linker-$V_H$. For each kappa/lambda scFv library, ~5 µg of BsaI digested vector pVCHuscFvSacBclo36006 was ligated to 3 µg of T4 DNA polymerase treated scFv fragments (molar ratio of ~1:3). For this, forty reactions of 10 µl each containing 1 µl 10× ligation buffer, 125 ng BsaI digested vector, 75 ng T4 DNA Polymerase treated purified inserts and 1.0 unit of T4 DNA ligase (Roche, Germany) were setup and incubated for 16 hours at 16° C. followed by 60 min at 37° C. and heat inactivation at 65° C. for 10 min. Ligation mixture was pooled (total 400 µl containing ~5 µg vector equivalent for each kappa/lambda library) and stored in 1.25 µg aliquots (4 aliquots for each kappa and lambda scFv library). Electroporations (Pulse at 2.5 kV voltage, 25 µF capacitance, and 200 ohm resistance) were performed in 0.2 cm Gene pulsar cuvettes (Biorad, Hercules, Germany) in 8 batches in electrocompetent TOP10F' cells prepared in-house with efficiency of ~1×10$^{10}$ per µg supercoiled pGEM-3Z DNA. For each batch comprising 1.25 µg ligated DNA, 25 electroporations were performed in total 5 sets. Cells from each set of 5 electroporations were regenerated in 20 ml SOC for one hour at 37° C., 250 rpm and plated on 20×150 mm plates containing LB agar with ampicillin (100 µg/ml) and glucose (1%) (LBAmp$_{100}$Glc$_{1\%}$) and incubated at 37° C. for 16 hrs. A small portion was appropriately diluted and plated on LBAmp$_{100}$Glc$_{1\%}$ plates to determine transformation efficiency. Each of the 5 sets was scraped into 40 ml 2×YT Glc$_{1\%}$ and primary transformants (C01) were stored at −80° C. in glycerol storage solution as 5 mini-libraries. The transformation efficiencies were found to be ~8-10×10$^8$/µg DNA. The mini-libraries were named as: HuscFvKLibC01 001-016 (~5×10$^9$ transformants) and HuscFvLLibC01 001-020 (~5×10$^9$ transformants).

Results Obtained

A large naive human scFv library comprising about 10 billion clones was constructed in a phagemid based phage display vector pVCHuscFvcloSacB36006 (FIG. 5). This gIIIp-based phagemid vector was exclusively designed for the seamless cloning and display of antibody variable genes in scFv format. The cloning strategy was modified to incorporate cloning site in the middle of PelB sequence (FIG. 5A) to eliminate addition of any extra amino-acid residues at the N-terminus of variable light chains (FIG. 5). Furthermore, this vector contains codon-optimized gIIIp sequence (SEQ ID NO: 101; corresponding amino acid sequence represented by SEQ ID NO: 102) to allow efficient expression of Fusion scFv-gIIIp protein and thereby improved display. It also contains ~2 kb SacB gene cassette (FIG. 5B) from B. subtilis as a stuffer fragment and allows for counter-selection of transformants on sucrose containing media, thereby ensuring selection of sucrose-resistant recombinants only.

Additionally, keeping in view, that visualization of DNA stained with ethidium-bromide under UV light damages the DNA thereby reducing ligation and transformation efficiencies, all the DNA manipulations described in this report for the purification of insert or vector fragments from agarose gels were carried out using SYBR Safe stain, which allows visualization under blue-light and hence prevents any DNA damage. Most importantly, to assemble scFv, the $V_L$ and $V_H$ chains were spliced using emulsion-based splicing by overlap extension PCR (SOE-ePCR). This step eliminates the chimerization of different antibody sequences, which are very similar. The spliced products ($V_K$-Linker-$V_H$ and $V_L$-Linker-$V_H$) were gel purified and treated with T4 DNA polymerase in the presence of dTTP to generate vector compatible 4-base 5' overhangs. These fragments were ligated to the BsaI digested pVCHuscFvSacBclo36006 for construction of two libraries viz. kappa and lambda scFv libraries.

For each library, 5 µg vector DNA was ligated to spliced scFv fragments and ligation reaction was electroporated in E. coli host TOP10F' in 4 batches. Each batch further comprised of 5 sets, which were referred as mini-libraries. Cleaner scFv preparations obtained using SOE-ePCR combined with use of blue-light for DNA manipulations, led to very high transformation efficiencies of ~8-10×10$^8$ per µg vector DNA with both kappa and lambda scFv libraries. In total, electroporation of 10 µg of ligated DNA sample yielded kappa and lambda scFv libraries comprising of approximately 10 billion primary transformants (C01). The mini-libraries each equivalent to approximately 250 ng DNA and comprising about 2.5×10$^8$ clones were named as HuscFvKLibC01 001-016 and HuscFvLLibC01 001-020. HuscFvKLibC01 was equal to 5 mini-libraries (1.25 µg DNA).

The phage-displayed naive human antibody library comprising 10 billion clones in scFv format in E. coli TOP10F' background was stored as 36 mini-libraries:
 (a). HuscFvKLibC01 001-016 mini-libraries (~5×10$^9$ clones)—These comprise the primary transformants (C01) encoding the human variable kappa light chain and variable heavy chain genes in $V_K$-Linker-$V_H$ format (HuscFvKLibC01 001 itself is equal to 5 mini-libraries, rest HuscFvKLibC01 002-16 represent 1 mini-library each).
 (b). HuscFvLLibC01 001-020 mini-libraries (~5×10$^9$ clones)—These comprise the primary transformants (C01) encoding the human variable lambda light chain and variable heavy chain genes in $V_L$-Linker-$V_H$ format.

Example 3

Characterization of Phage Displayed Naïve Human Antibody Library Using Sanger Sequencing and Next-Generation Sequencing on MiSeq Platform
Method Used:
Sanger Sequencing-Based Analysis of Naïve Human Antibody Library Clones Forty-eight randomly selected clones each from kappa and lambda naïve human antibody libraries were analyzed using colony PCR with 5' primer M13R (SEQ ID NO: 99) (5'-AGCGGATAACAATTTCACACAGGA-3') and 3' primer U251CO (SEQ ID NO: 100) (5'-GGTTTTAT-CATCTTTCCACACGT-3'). PCR products were analyzed on 1.2% analytical agarose gel and sequenced using 2 primers, namely, M13R and U251CO using BigDye terminator chemistry on ABI 3730 XL sequencing platform (Applied Biosystems, Thermo Fisher Scientific, Waltham, USA). The sequences were assembled using MacVector 12.5.1 and analyzed using IMGT V-quest (Brochet, X., M. P. Lefranc and V. Giudicelli (2008). "IMGT/V-QUEST: the highly customized and integrated system for IG and TR standardized V-J and V-D-J sequence analysis." Nucleic Acids Res 36(Web Server issue): W503-8).
Preparation of Dual-Indexed Variable Domain Libraries for Sequencing Using MiSeq (Illumina)

Approximately 1×10$^9$ cells from HuscFvKLibC01-015 and HuscFvLLibC01-010 mini-libraries were inoculated in 20 ml MDAGAmp$_{100}$ media (MDAG media containing 100 µg/ml ampicillin) and cultures were grown at 37° C. for 16 hr at 250 rpm. Plasmid DNA was purified from 3 ml culture using SureSpin plasmid miniprep kit (Genetix Biotech Asia Pvt. Ltd.) as per manufacturer's instructions and eluted in 60 µl 0.1×TE buffer.

Dual-indexed variable light chain (Kappa and Lambda) and variable heavy chain libraries were prepared separately by PCR amplification of the cloned variable genes from HuscFvKLibC01-015 and HuscFvLLibC01-010 mini-libraries using two-step emulsion PCR (ePCR). For first-step ePCR-based amplification of the variable light chain genes, the aqueous PCR mix was set up in a volume of 260 µl containing 10 mg/ml BSA (Roche), 200 µM dNTPs (Roche), 1% DMSO, 78 pmoles each of 5' primer HuPelBNextThio-52 and 3' primer HuG4SNextThio-31, 3×10$^9$ template DNA molecules (purified plasmid of HuscFvKLibC01-015 or HuscFvLLibC01-010 mini-libraries) and 6 U of PfuUltra II Fusion HS polymerase in 1×PfuUltra II Fusion HS polymerase buffer. 250 µl aqueous PCR was emulsified in 500 µl oil-surfactant mix. The emulsion was transferred to 0.2 ml PCR tubes (50 µl/tube; total 15 tubes), overlaid with 50 µl mineral oil and subjected to PCR with initial denaturation at 95° C. for 3 min followed by thermocycling for 30 cycles comprising of denaturation at 95° C. for 30 sec, annealing at 55° C. for 30 sec and polymerization at 72° C. for 9 sec followed by final polymerization at 72° C. for 2 min. Simultaneously, 10 µl of aqueous PCR (no emulsification) was also subjected to PCR under same conditions (Conventional PCR; cPCR). Following PCR, emulsion was pooled, broken with diethyl ether and purified using QIAquick PCR purification kit. The PCR product was eluted in 60 µl EB and quantified using Qubit Fluorometer 2.0 (Thermo Fisher Scientific, Waltham, USA) with Qubit dsDNA BR kit as per manufacturer's instructions.

For the first-step ePCR-based amplification of variable heavy chain genes, aqueous PCR mix was set up in a volume of 260 µl containing 10 mg/ml BSA (Roche), 200 µM dNTPs (Roche), 1% DMSO, 78 pmoles each of 5' primer HuG4SNextThio-51 and 3' primer HuCH1NextThio-31, 3×10$^9$ template DNA molecules (purified plasmid of HuscFvKLibC01-015 or HuscFvLLibC01-010 mini-libraries) and 6 U of PfuUltra II Fusion HS polymerase in 1×PfuUltra II Fusion HS polymerase buffer. Remaining emulsion PCR and purification protocol was same as described above.

For the second-step ePCR-based amplification of variable light and heavy chain genes, aqueous PCR mix was set up in a volume of 260 µl containing 10 mg/ml BSA (Roche), 200 µM dNTPs (Roche), 1% DMSO, 78 pmoles each of 5' indexing primer P5N502NextE-51 (Light chain)/P5 N503NextEThio-51 (Heavy chain) and 3' primer P7 N702NextE-31 (Light chain)/P7N703NextEThio-31 (Heavy chain), 3×10$^9$ template DNA molecules [purified light or heavy chain amplicon (~460-480 bp) from first-step ePCR] and 6 U of PfuUltra II Fusion HS polymerase in 1×PfuUltra II Fusion HS polymerase buffer. Remaining emulsion PCR and purification protocol was same as described above.

Next-Generation Sequencing of Dual-Indexed Variable Light and Heavy Chain Libraries Using MiSeq Sequencer (Illumina)

The dual-indexed variable light and heavy chain libraries were sequenced together in a single run for each mini-library. For sequencing the variable light and heavy chain gene libraries derived from HuscFvKLib-015 mini-library, the two libraries carrying separate indices were mixed in equimolar ratio and loaded at 6 µM concentration further spiked with 15% PhiX high-diversity control library (cat no. FC-110-3001, Illumina). For this, the PCR amplified dual-indexed variable light and heavy chain libraries were diluted separately to 4 nM concentration in Qiagen EB (10 mM Tris-HCl, pH 8.0) and 10 µl of each was pooled. 5 µl of the pooled library mix was denatured by mixing with 5 µl freshly prepared 0.2 N NaOH followed by incubation at RT (~25° C.) for 5 min. The denatured library was neutralized with 990 µl ice-cold HT1 buffer (Illumina), and the resultant 20 µM denatured library was further diluted to 6 µM in the ice-cold HT1 buffer. PhiX control library (FC-110-3001) was similarly denatured and diluted to 6 µM. To obtain the "final library mix" containing 6 µM equimolar mix of variable light and heavy chain libraries with 15% PhiX, 850 µl of the 6 µM denatured library was mixed with 150 µl of 6 µM denatured PhiX library. The sequencing was performed using MiSeq Nano v2 reagent kit (MS-103-1003, Illumina) for 2×250 cycles of paired-end sequencing. The reagent cartridge and flow-cell were prepared as per manufacturer's instructions and 600 µl of final library mix was loaded in the empty sample well 17 of the pre-filled sequencing reagent cartridge. Sequencing run was started and comprised of 518 sequencing cycles in total, with 2×251 cycles of paired-end sequencing and 2×8 cycles of index sequencing, followed by generation of reads in the Fastq format as defined in the sample sheet. The variable light and heavy chain gene libraries derived from HuscFvLLib-010 mini-library were also sequenced using same protocol as described above.

Analysis of the Next-Generation Sequencing Data Using Bioinformatics

MiSeq sequencing run generated de-multiplexed reads in fastq.gz format (R1.fastq.gz and R2.fastq.gz). The fastq.gz files were unzipped and the paired-end reads were merged using SeqPrep-master tool available at Github. The sequences at 5' and 3' ends encoding part PelB sequence and CH1 spacer, respectively were trimmed using cutadapt tool (version 1.2.1) (Martin 2011. "Cutadapt removes adapter sequences from high-throughput sequencing reads." EMB-.net Journal 17(1): 10-12). The merged and trimmed fastq format file was converted into fasta file, which was further split into smaller files containing 1,50,000 sequences for analysis using IMGT/HighV-QUEST (Brochet et al., 2008, "IMGT/V-QUEST: the highly customized and integrated system for IG and TR standardized V-J and V-D-J sequence analysis". Nucl. Acids Res, 36, W503-508). The files obtained after statistical analysis of data on IMGT/HighV-QUEST were analyzed using Microsoft Excel to extract relevant information.

Results Obtained

Characterization of the Phage-Displayed Naïve Human Antibody Library Using Next-Generation Sequencing and Sanger Sequencing The availability of technologies for massively parallel sequencing provides an opportunity to characterize the large libraries at genome-scale, which was not possible before using Sanger-based sequencing. In this example, MiSeq platform based on Sequencing By Synthesis (SBS; Illumina) chemistry was employed to sequence and characterize a portion of the naïve human antibody library available in the laboratory. Since the library is available in scFv format, which are typically ~750 bp in size, the entire scFv sequence cannot be determined by NGS using MiSeq, which currently allows a maximum of 2×300 base paired-end sequencing. Hence, the variable light and heavy chain genes of the scFv were amplified separately for sequencing (FIG. 6). The only limitation of this method is that the original pairing of variable light and heavy chain genes cannot be determined.

Next-Generation Sequencing of the Dual-Indexed Variable Light and Heavy Chain Gene Libraries The dual-indexed variable light and heavy chain libraries were prepared by two-step emulsion PCR-based amplification of the cloned variable genes from one mini-library each of kappa and lambda scFv libraries (FIG. 6 and FIG. 7). The details of the primer have been listed in Table 2.

TABLE 2

| Primer | Length | Sequence (5'-3')# |
|---|---|---|
| HuPelBNextThio-42 (SEQ ID NO: 103) | 58 | TCGTCGGCAGCGTCAGATGTGTATAAGAGACAGGCTACTGATGACAGCTCAGCCAGC*G |
| HuG4SNextThio-31 (SEQ ID NO: 104) | 57 | GTCTCGTGGGCTCGGAGATGTGTATAAGAGACAGGCCTCCAGAGCCACCGCCACCGGA*T |
| HuG4SNextThio-51 (SEQ ID NO: 105) | 57 | TCGTCGGCAGCGTCAGATGTGTATAAGAGACAGGCGGTGGCTCTGGAGGCGGTGGA*A |
| HuCH1NextThio-31 (SEQ ID NO: 106) | 57 | GTCTCGTGGGCTCGGAGATGTGTATAAGAGACAGCTTTGTACTCGCTGAGGAGACGG*T |
| P5N502NextE-51 (SEQ ID NO: 107) | 58 | AATGATACGGCGACCACCGAGATCTACACCTCTCTATTCGTCGGCAGCGTCAGATGT*G |
| P7N702NextE-31 (SEQ ID NO: 108) | 55 | CAAGCAGAAGACGGCATACGAGATCTAGTACGGTCTCGTGGGCTCGGAGATGTG*T |
| P5N503NextEThio-51 (SEQ ID NO: 109) | 58 | AATGATACGGCGACCACCGAGATCTACACTATCCTCTTCGTCGGCAGCGTCAGATGT*G |
| P7N703NextEThio-31 (SEQ ID NO: 110) | 55 | CAAGCAGAAGACGGCATACGAGATTTCTGCCTGTCTCGTGGGCTCGGAGATGTG*T |

The primer sequences have been modified from the sequence provided by Illumina, Inc.
Oligonucleotide sequences © 2016 Illumina, Inc. "All rights reserved.
Derivative works created by Illumina customers are authorized for use with Illumina instruments and products only.
All other uses are strictly prohibited".
*denotes phosphorothioate modification before the last base at 3' end of all the primers.

The variable light and heavy chain gene libraries derived from kappa/lambda scFv libraries carried different indices and hence, were mixed in equimolar ratio for sequencing together in a single run. Following the MiSeq sequencing primer-binding site, all the fragments in the variable light and heavy chain gene library carried a common DNA sequence at 5' and 3' ends, which was employed as the primer binding site in first-step ePCR (FIG. 6). These common sequences make these libraries 'low-diversity' and can cause failure in cluster identification, as all the clusters would read identical base in a given cycle during sequencing of these adapters. Hence, to address this issue, the variable light and heavy chain library mix was loaded at 6 µM concentration further spiked with 15% PhiX high-diversity control library on MiSeq Nano v2 reagent kit for 2×250 cycles of paired-end sequencing. The sequencing runs were very successful and yielded high quality sequencing data in fastq.gz format.

Analysis of Variable Light and Heavy Chain Sequences Using IMGT

The analysis of variable light ($V_L$) and heavy chain ($V_H$) genes encoded in the kappa antibody library revealed that approximately 72.5% and 90.6% of the variable light and heavy chains, respectively, carried unique sequences in the kappa antibody library (Table 3).

TABLE 3

| Library | Sequence subset | Total No. of Sequences Analyzed | No. of Unique Sequences | % Unique sequences | Average % Unique sequences |
|---|---|---|---|---|---|
| Kappa VL | 1 | 150000 | 109234 | 72.8% | 72.5% |
|  | 2 | 142294 | 102922 | 72.3% |  |
| Kappa VH | 1 | 128574 | 116514 | 90.6% | 90.6% |
| Lambda VL | 1 | 150000 | 104505 | 69.6% | 70.9% |
|  | 2 | 112261 | 81080 | 72.2% |  |
| Lambda VH | 1 | 150000 | 133819 | 89.2% | 92.2% |
|  | 2 | 1931 | 1842 | 95.3% |  |

Similarly, 70.9% and 92.2% of the variable light and heavy chains, respectively, carried unique sequences in the lambda antibody library. Since, the scFv sequences are a result of the combination of light and heavy chain genes, it should be noted that even though the diversity at variable light chain gene level is relatively low as compared to variable heavy chain genes (Table 3), the total number of possibilities after random splicing of genes greatly exceeds the size of total library described here, pointing towards the vast diversity of the scFv sequences in the library.

The number of productive variable light and heavy chain sequences was found to be 90.5% and 95%, respectively, for kappa antibody libraries and 89.4% and 94.7%, respectively, for lambda antibody libraries (Table 4). The efficiency of obtaining more productive $V_L$ and $V_H$ can be increased if the initial PCR of individual $V_L$ and $V_H$ is also carried out using emulsion PCR.

TABLE 4

| | Kappa | | Lambda | |
|---|---|---|---|---|
| Functionality | $V_L$ | $V_H$ | $V_L$ | $V_H$ |
| Productive | 264621 (90.5%) | 122174 (95%) | 234418 (89.4%) | 143844 (94.7%) |
| Unproductive | 24106 (8.2%) | 5439 (4.2%) | 19964 (7.6%) | 7331 (4.8%) |
| Unknown | 3167 (1.1%) | 502 (0.4%) | 7476 (2.9%) | 329 (0.2%) |
| No results | 400 (0.1%) | 459 (0.4%) | 403 (0.2%) | 427 (0.2%) |
| Total | 292294 | 128574 | 262261 | 151931 |

As per IMGT, "*A rearranged immunoglobulin or T cell receptor (genomic or cDNA) entity is productive if the coding region has an open reading frame, with no stop codon and no defect described in the initiation codon, splicing sites and/or regulatory elements, and an in-frame junction*" (Lefranc et al., 1999). According to these numbers, after variable gene assembly, the number of clones carrying scFv in the correct reading frame should be approximately 85.9% (90.5%×95%) and 84.6% (89.4%×94.7%) in kappa and lambda antibody libraries, respectively. On the other hand, the Sanger sequencing-based analysis of 48 randomly selected clones from both kappa and lambda antibody libraries revealed that 100% clones were recombinant, and all carried full-length scFv, but only ~75% and ~60% of the clones from kappa and lambda libraries, respectively, carried scFv sequence in correct reading frame. However, it should be noted that approximately 10% of the sequenced clones were off-frame because they carried deletions/mutations in the 15-amino acid linker region between the variable light and heavy chain genes, which is also the site for gene splicing during PCR-based scFv assembly. This is likely due to the mis-priming events occurring during PCR between the highly similar codons of glycine in the (Gly4Ser3)3 linker. However, this linker region is not sequenced during next-generation sequencing (FIG. 6). Thus, after taking into account the number of clones that become off-frame due to defective linker sequence, the effective numbers of productive scFv sequences obtained by Sanger's method-based sequencing are concordant with the next-generation sequencing data and the data reported for other libraries constructed using PCR-based variable gene amplification and scFv assembly (Hust et al., 2011 "A human scFv antibody generation pipeline for proteome research." J Biotechnol 152(4): 159-70; Schwimmer et al., 2013). In other words, the human naïve antibody library comprises of nearly $7×10^9$ clones with unique in-frame scFv sequences capable of being displayed on the phage surface.

The variable light and heavy chain gene family representation across the kappa and lambda antibody libraries was also found to be largely concordant with the already reported variable gene usage based on a database of 1006 rearranged sequences found in vivo (Knappik et al., 2000 "Fully synthetic human combinatorial antibody libraries (HuCAL) based on modular consensus frameworks and CDRs randomized with trinucleotides." J Mol Biol 296(1): 57-86) and based on the sequencing of 154 scFv sequences from naïve HAL8 (kappa) library and 200 scFv sequences from naïve HAL8 (Lambda) library (Hust et al., 2011, "A human scFv antibody generation pipeline for proteome research." J Biotechnol 152(4): 159-70), with few variations (FIG. 8, A-D). The VK3 gene family (41.96%) was found to be the most abundant kappa light chain family followed by VK1 (38.76%) and VK4 (10.46%), which is concordant with reported data (FIG. 8A). In case of variable lambda light chain families, VL3 family (28%) was found to be most abundant gene family followed by VL1 (20.36%) and VL2 (18.12%) (FIG. 8C). In case of heavy chain gene families, VH1 was found to be most abundant gene family in both kappa and lambda antibody libraries in contrast to VH3 family, which is reported to be most abundant by Knappik et al., 2000 and Hust et al., 2011 (FIGS. 8B and 8D). Such differences in the gene representation are likely to be present due to the variations introduced by PCR-based amplification of antibody genes, the source of RNA, primer design, and the method of pooling the genes before assembly.

The analysis of data obtained from Sanger sequencing of scFv genes from kappa and lambda antibody libraries for their match to the antibody germline sequences further revealed that most of the sequences were >96% identical to germline sequences, with several clones carrying 100% identical sequences (twelve representative clones are shown in Table 5 and 6). This is an important feature reflecting towards the naïve-ness of the antibody library, which is highly desirable to ensure that the library is not majorly primed against any specific targets and will likely yield specific binders against a wide range of targets.

Table 5: Sequence analysis of randomly selected naïve Human Antibody Kappa library clones using IMGT. Randomly selected clones from naïve Human Antibody Kappa library were screened using colony PCR and sequenced using Sanger based sequencing. The variable light and heavy chain sequences were analyzed using IMGT V-Quest and data of 12 representative clones is summarized in the table.

TABLE 5

| Clone | FR1 | CDR1 | FR2 | CDR2 | FR3 | CDR3 | Germline | Amino acid different from germline | Family | Percentage Identity (at nucleotide level) |
|---|---|---|---|---|---|---|---|---|---|---|
| 3 | DIRLTQSPD SLAVSLGER ATINCKSS | QSVLY SSNNK NY | LAWYQQKP GHPPKLLI Y | WAS | ARESGVPDRF SGSGSGTDFT LTINSLQAED VAVYYC | QQCYST PPT | IGKV4-1*01 F | 6 | VK4 | 96.97% |
| | QITLKESGP TLVKPTQTL TLTCTFS | GYTFT SYG | VGWIRQPP GKALEWLA L | IYWDD DK | RYSPSLKSRL TITKDTSKNQ VVLTMTNMDP VDTATYYC | AHARWY FDY | IGHV2-5*02 F | 0 | VH2 | 100.00% |
| 5 | ETTLTQSPG TLSLSPGER ATLSCRAS | QSVSS SY | LAWYQQKP GQAPRLLI Y | GAS | SRATGIPDRF SGSGSGADFT LTISRLEPED FAVYYC | QQTGSS PL | IGKV3-20*01 F | 3 | VK3 | 97.16% |
| | QMQLVQSGA EVKKPGASV KVSCKAS | GDSVS SDSAA A | ISWVRQAP GQGLEWMG R | IIPIL GIA | NYAQKFQGRV TITADKSTST AYMEKSSLRS EDTAVYYC | ARDFQD GELLWY FDL | IGHV1-69*09 F | 5 | VH1 | 95.83% |
| 7 | DIMMTQSPS SLSASVGDR VTITCRAS | QSISS Y | LNWYQQKP GKAPKLLI Y | AAS | SLQSGVPSRF SGSGSGTDFT LTISSLQPED FATYYC | QQSYS | IGKV1-39*01 F | 1 | VK1 | 99.28% |
| | QITLKESGP ALVKPTQTL TLTCTFS | GFSLS TSGVG | VGWIRQPP GKALEWLA L | IYWDD DK | RYSPSLKSRL TITKDTSKNQ VVLTMTNMDP VDTATYYC | ALTATA FDI | IGHV2-5*02 F | 2 | VH2 | 99.31% |
| 8 | DIVMTQSPD SLAVSLGER ATINCKSS | QSVLY SSNNK NY | LAWYQQKP GQPPKLLI Y | WAS | TRESGVPDRF SGSGSGTDFT LTISSLQAED VAVYYC | QQYYST PRT | IGKV4-1*01 F | 0 | VK4 | 99.66% |
| | KVTLKESGP ALVKPTQTL TLTCTFS | GFSLS TSGMR | ASWIRQPP GKALEWLA R | IDWDD DK | YYSTSLKTRL TISKDTSKNQ VVLTMTNMDP VDTATYYC | ARIPSC ITMMEG FDP | IGHV2-70*10 F | 3 | VH2 | 98.63% |
| 9 | DIQMTQSPS SLSASVGDR VTITCRAS | QSISS S | LNWYQQKP GKAPKLLI Y | AAS | TLQSGVPSRF SGSGSGTDFT LTISSLQPED FATYYC | QQSYST PIT | IGKV1-39*01 F | 2 | VK1 | 98.57% |
| | EVQLVQSGA EVKKPGASV KVSCKAS | GYIFT SYY | INAGNGNT | INAGN GNT | EYSQKFQGRV TITRDTSAST AYMELSSLRS EDTAVYYC | ARETGD AFDI | IGHV1-3*01 F | 4 | VH1 | 96.53% |
| 10 | ETTLTQSPG TLSLSPGER ATLSCRAS | QSVSS SY | LAWYQQKP GQAPRLLI Y | GAS | SRATGIPDRF SGSGSGTDFT LTISRLEPED FAVYYC | QQYGSS PRT | IGKV3-20*01 F | 2 | VK3 | 97.52% |
| | QVQLVQSGA EVKKPGESL RISCKGS | GYSFT SYW | ISWVRQPP GKGLEWMG R | IDPSD SYT | NYSPSFQGHV TISADLSIST AYLQWSSLKA SATAMYYC | ARLNWK SEYFQH | IGHV5-10-1*01 F | | VH5 | 99.31% |

TABLE 5-continued

| Clone | FR1 | CDR1 | FR2 | CDR2 | FR3 | CDR3 | Germline | Amino acid different from germline | Family | Percentage Identity (at nucleotide level) |
|---|---|---|---|---|---|---|---|---|---|---|
| 13 | DIVMTQSPD SLAVSLGER ATINCKSS | QSVLY SSNNK NY | LAWYQQKP GQPPKLLI Y | WAS | ARESGVPDRF SGSGSGTDFT LTISSLQAED VAVYYC | QQYYST PFT | IGKV4-1*01 F | 1 | VK4 | 99.33% |
|  | EVQLVQSGA EVKKPGASV KVSCKAS | GYTFT SYD | INWVRQAT GQGLEWMG W | MNPNS GNT | GYAQKFQGRV TMTRNTSIST AYMELSSLRS EDTAEYYC | ARAVAG TGDI | IGHV1-8*01 F | 2 | VH1 | 98.61% |
| 15 | ETTLTQSPG TLSLSPGER ATLSCRAS | QSVSS SY | LAWYQQKP GQAPRLLI Y | GAS | TRATGIPARF SGSGSGTEFT LTISSLQSED FAVYYC | QQYNNM PPIT | IGKV3-15*01 F | 6 | VK3 | 96.42% |
|  | QVQLQQSGA GLLKPSETL SLTCAVY | GGSFS GYY | WSWIRQPP GKGLEWIG E | INHSG ST | DYAVSVKSRI TNPDTSKNQ FSLQLNSVTP EDTAVYYC | ARACSS TSCYDY | IGHV4-34*01 F | 1 | VH4 | 98.60% |
| 16 | EIVMTQSPG TLSLSPGER ATLSCRAS | QSVSS Y | LAWYQQKP GQAPRLLI Y | DAS | NRATGIPARF SGSGSGTDFT LTISSLEPED EDTAVYYC | QQRSSW IT | IGKV3-11*01 F | 3 | VK3 | 98.57% |
|  | QVQLVQSGA EVKKPGASV KVSCKAS | GYTFT SYY | MHWVRQAP GQGLEWMG I | INPSG GST | SYAQKFQGRV TMTRDTSTST VYMELSSLRS EDTAVYYC | AREKSV YSSPLS VHYYGM DV | IGHV1-46*01 F | 0 | VH1 | 99.65% |
| 17 | DIQLTQSPS SLSASVGDR VTITCRAS | QSISS Y | LNWYQQKP GKAPKLLI Y | AAS | SLQSGVPSRF SGSGSGTDFT LTISSLQPED FATYYC | QQSYST PRT | IGKV1-39*01 F | 1 | VK1 | 99.64% |
|  | QVQLQESGAG-GLVKPGGSL RLSCAAS | GFTFN SYS | MNWVRQAP GKGLEWVS S | ISSSS SYI | YYADSVKGRF TISRDNAKNS LNLQMNSLRA EDTAVYYC | ARYSSG WYLPY | IGHV3-21*02 F | 4 | VH3 | 97.57% |
| 24 | EIVLTQSPA TLSLSPGER ATLSCRAS | QSVSS Y | LAWYQQKP GQAPRLLI Y | DAS | NRATGIPARF SGSGSGTDFT LTISSLEPED FAVYYC | QQRSNW PPIT | IGKV3-11*01 F | 0 | VK3 | 100.00% |
|  | QVTLKESGP TLVKPTQTL TLTCTFS | GFSLS TSGVG | VGWIRQPP GKALEWLA L | IYWDD DK | RYSPSLKSRL TITKDTSKNQ VVLTMTNMDP EDTAVYYC | ARFPGI PNFDY | IGHV2-5*02 F | 1 | VH2 | 99.66% |
| 27 | ETTLTQSPA FMSATPGDK VINSCKAS | QDIDD D | MNWYQQKP GEAAIFII Q | EAT | LVPGIPPRF SGSGYGTDFT LTNNIESED AAYYFC | LQHDNF PLQ | IGKV5-2*01 F | 0 | VK5 | 100.00% |
|  | SELVQSGPG LVKPSQTLS LTCAIS | GDSVS SNSAA A | WNWIRQSP SRGLEWLG R | TYYRS KWYN | DYAVSVKSRI TNPDTSKNQ FSLQLNSVTP EDTAVYYC | ARETGD IDGYFD Y | IGHV6-1*01 F | 3 | VH6 | 96.96% |

Table 6: Sequence analysis of randomly selected naïve Human Antibody Lambda library clones using IMGT. Randomly selected clones from naïve Human Antibody Lambda library were screened using colony PCR and sequenced using Sanger based sequencing. The variable light and heavy chain sequences were analyzed using IMGT V-Quest and data of 12 representative clones is summarized in the table.

| Clone | FR1 | CDR1 | FR2 | CDR2 | FR3 | CDR3 | Germline | Amino acid different from germline | Family | Percentage Identity |
|---|---|---|---|---|---|---|---|---|---|---|
| 53 | LPVLTQPHSVSESPGKTVTISCTRS | SGSIASNY | VQWYQQRPGSAPTTVIY | EDN | QRPSGVPDRFSGSIDSSSNSASLTISGLKTEDEADYYC | QSYDSSNVV | IGLV6-57*01 F | 4 | VL6 | 97.59% |
|  | QITLKESGPALVKPTQTLTLTCTFS | GFSLSTSGVG | VGWIRQPPGKALEWLAL | IYWNDDK | RYSPSLKSRLTITKDTSKNQVVLTMTSMDPVDTATYYC | AHRMVTAIYSIFDY | IGHV2-5*01 F | 2 | VH2 | 99.31% |
| 58 | QAVVTQEPSFSVSPGGTVTLTCGLS | SGSVSTSYY | PSWYQQTPGQAPRTLIY | STN | TRSSGVPDRFSGSILGNKAALTITGAQADDESDYYC | VLYMGSGILV | IGLV8-61*01 F | 1 | VL8 | 99.31% |
|  | EVQLVQSGPGLVKPSQTLSLTCAIS | GDSVSSNSAA | WNWIRQSPSRGLEWLGR | TYYRSKWYN | DYAVSVKSRITINPDTSKNQFSLQLNSVTPEDTAVYYC | ARYSSSWYWFDP | IGHV6-1*01 F | 2 | VH6 | 97.98% |
| 59 | SYVLTQPPSASGTPGQRVTISCSGS | SSNIESNY | VYWYQQLPGTAPKLLIY | RNN | QQPSGVPDRFSGSKSGTSASLAISGLQSEDEADYYC | AAWDDSLSGPV | IGLV1-47*01 F | 5 | VL1 | 96.84% |
|  | QVQLQECGAEVKKPGESLKISCKGS | GYSFTSYW | IGWVRQMPGKGLEWMGI | IYPGDSDT | RYSPSFQGQVTISADKSISTAYLQWSSLKASDTAMYYC | ARSNSSGWHDAFDI | IGHV5-51*01 F | 4 | VH5 | 97.57% |
| 62 | LPVLTQPHSVSESPGKTVTISCTRS | SGSIASNY | VQWYQQRRGSAPTTVIY | EDN | QRPSGVPDRFSGSIDSSSNSASLTISGLKTEDEADYYC | QSYDSSNHGV | IGLV6-57*01 F | 5 | VL6 | 97.25% |
|  | QVQLQQSGAGLLKPSETLSLTCAVY | GGSFSGYY | WSWIRQPPGKGLEWIGE | INHSGST | NYNPSLKSRVTISVDTSKNQFSLKLSSVTAADTAVYYC | ARWGQNWVFDI | IGHV4-34*01 F | 1 | VH4 | 98.60% |
| 63 | QPVLTQPPSVSVSPGQTASITCSGD | KLGDKY | ACWYQQKPGQSPVLVIY | QDS | KRPSGIPERFSGSNSGNTATLTISGTQAMDEADYYC | QAWDSSTVV | IGLV3-1*01 F | 3 | VL3 | 97.85% |
|  | QVTLKESGPTLVKPTQTLTLTCTFS | GFSLSTSGVG | VGWIRQPPGKALEWLAL | IYWNDDK | RYSPSLRSRLTITKDTSKNQVVLTMTNMDPVDTATYYC | ALLNWGLENWFDP | IGHV2-5*01 F | 2 | VH2 | 99.31% |
| 66 | QPVLTQSPSASGTPGQRVTISCSGS | SSNIGSNY | VYWYQQLPGTAPKLLIY | RNN | QRPSGVPDRFSGSESGTSASLAISGLRSEDEADYYC | AAWDDSLSGPV | IGLV1-47*01 F | 3 | VL1 | 97.89% |
|  | EVQLVQSGPGLVKPSGTLSLTCAVY | GGSFSGYY | WSWIRQPPGKGLEWIGE | INHSGST | NYNPSLKSRVTISVDTSKNQFFLKLRSVTAADTAVYYC | ARFRKKGSYADY | IGHV4-34*01 F | 8 | VH4 | 95.79% |
| 68 | NFMLTQPHSVSESPGKTVTISCTRS | SGSIASNY | VQWYQRRPGSAPTTVIY | EDN | QRPSGVPDRFSGSIDSSSNSASLTISGLKTEDEADYYC | QSYDSRNVV | IGLV6-57*01 F | 3 | VL6 | 98.97% |
|  | EVQLVQSAPEVKKPGASVKVSCKAS | GYTFTGYY | MHWVRQAPGQGLEWMGW | INPNSGGT | NYAQKFQGRVTMTRDTSISTAYMELSRLRSDDTAVYYC | ARPLTAFDY | IGHV1-2*02 F | 3 | VH1 | 98.96% |
| 74 | QSVLTQPPSVSVAPGKTARITCGGN | NIGSKS | VHWYQQKPGQAPVLVVY | GDS | DRPSGIPERFSGSNSGNTATLTISRVEAGDEADYYC | QVWDSSSDHVV | IGLV3-21*03 F | 3 | VL3 | 97.85% |
|  | QVTLKESGPTLVKPTQTLTMTCTFS | GFSLRTSGVG | VGWIRQPPGKALEWLAL | IYWNDDK | RYSPSLKSRLTITKDTSKDQVVLTMTNMDPVDTATYYC | ARIGGDNGLDY | IGHV2-5*01 F | 4 | VH5 | 96.56% |

| Clone | FR1 | CDR1 | FR2 | CDR2 | FR3 | CDR3 | Germline | Amino acid different from germline | Family | Percentage Identity |
|---|---|---|---|---|---|---|---|---|---|---|
| 79 | SSELTQDP AVSVALGQ TVKITCQG D | SLRSYY | ASWYQQKP GQAPVLVI Y | GEN | NRPSGIPDRF SGSSSGSTAS LIITGAQAED EADYYC | NCRDSS SSHVL | IGLV3-19*01 F | 7 | VL3 | 97.49% |
|  | QITLKESG PALVKPTQ TLTLTCTF S | GFSLST SGMC | VSWIRQPP GKTLEWLA L | IYWDD DK | RYSPSLKSRL TITKDTSKNQ VVLTMTNMDP VDTATYYC | AHFTTY YYDSSG YYYFDY | IGHV2-5*08 F | 3 | VH2 | 98.63% |
| 80 | LPVLTQPH SVSESPGK TVTISCTR S | SGSIAS NY | VQWYQQRP GSSPTTVI Y | EDN | QRPSGVPDRF SGSIDSSSNS ASLTISGLKT GDEADYYC | QSYDSS NHWV | IGLV6-57*01 F | 4 | VL6 | 97.25% |
|  | QVQLQESG PGLVKPSQ TLSLTCTV S | GGSISS GDYY | WSWIRQPP GKGLEWIG Y | IYYSG ST | YYNPSLKSRV TISVDTSKNQ FSLKLSSVTA ADTAVYYC | ARGLRW NHNWFD P | IGHV4-30-4*01 F | 0 | VH4 | 100.00% |
| 82 | QSALTQPP SASGSPGQ SVTISCTG T | SSDVGG YNY | VSWYQQHP GKAPKLMI Y | EVS | KRPSGVPDRF SGSKSGNTAS LTVSGLQAED EADYYC | SSYAGS NNLV | IGLV2-8*01 F | 0 | VL2 | 100.00% |
|  | EVQLVQSG PGLVKPSQ TLSLTCAI S | GDSVSS NSAA | WNWIRQSP SRGLEWLG R | TYYRS KWYN | DYAVSVKSRI TINPDTSKNQ FSLQLNSVTP EDTAVYYC | ARVRGE QWLPTD DAFDI | IGHV6-1*01 F | 2 | VH6 | 98.32% |
| 83 | SSELTQDP AVSVALGQ TVRITCQG D | SLRSYY | ASWYQQKP GQAPVLVI Y | GKN | NRPSGIPDRF SGSSSGNTAS LTITGAQAED EADYYC | NSRDSS GNHVV | IGLV3-19*01 F | 0 | VL3 | 100.00% |
|  | QMQLVQSG AEVKKPGE SLKISCKG S | GYSFTS YW | IGWVRQMP GKGLEWMG I | ICPGD SDT | RYSPSFQGQV TISADKSIST AYLQWSSLKA SDTAMYYC | ARQGLN DAFDI | IGHV5-51*01 F | 3 | VH5 | 97.57% |

The length of CDRs, especially CDR3 was found to highly variable in both the variable light and heavy chain genes (FIGS. 9-12). In kappa antibody library, the length of KVL-CDR3 was found to be between 8-10 amino acids for greater than 95% sequences, and approximately 70.75% sequences carried CDR3 with a length of 9 amino acids (FIG. 9C). In lambda antibody library, the length of LVL-CDR3 was found to be between 9-11 amino acids for greater than 93% sequences, however, unlike KVL-CDR3, the clones with CDR3 length of 9, 10, and 11 amino acids were almost equally represented (~28-36%; FIG. 11C). The length of heavy chain CDR3 varied between 2-35 amino acids and greater than 50% of the sequences carried CDR3 with length ranging between 11-14 amino acids in both kappa and lambda antibody libraries (FIGS. 10 and 12C). Glanville et al. (Glanville, J., W. Zhai, J. Berka, D. Telman, G. Huerta, G. R. Mehta, I. Ni, L. Mei, P. D. Sundar, G. M. Day, D. Cox, A. Rajpal and J. Pons (2009). "Precise determination of the diversity of a combinatorial antibody library gives insight into the human immunoglobulin repertoire." Proc Natl Acad Sci USA 106(48): 20216-21) also performed the next-generation sequencing of a naïve human antibody library and observed the HCDR3 length ranging between 1-31 amino acids. This wide range of heavy chain CDR3 length distribution is expected to contribute to a large number of structures in the antibody's paratope region, (Glanville et al., 2009) which can facilitate the isolation of binders against a wide-range of targets.

Example 4

Rescue of the Naïve Human Antibody Library Using AGM13 Helper Phage

Method Used:

Phages were rescued in 8 batches, each comprising of 5 mini-libraries. For every batch, one aliquot each of the 5 mini-libraries (total equivalent to ~1.25×10$^9$ transformants) was thawed and pooled. For HuscFvKlib-001 (which itself is equivalent to 5 mini-libraries derived from ~1.25 μg DNA and is equal to ~1.25×10$^9$ binders) only 1 vial was thawed. An aliquot containing a total of ~5×10$^{10}$ cells (40-fold excess) were diluted in 2×600 ml 2×YT Glu$_{1\%}$ (2×YT media containing 1% glucose) and grown at 37° C., 250 rpm for 30 min. Ampicillin was added to a final concentration of 100 μg/ml and culture was grown at 37° C., 220 rpm till OD$_{600nm}$~0.4-0.5 was obtained. After this, the culture was kept for slow shaking at 100 rpm for 30 min. The cells were subjected to infection with helper phage AGM13 at MOI of 20 for 30 min at 37° C. (without shaking), followed by growth at 37° C., 100 rpm for 30 min. The infected culture was harvested at 5000 rpm, 10 min, RT and the cell pellet from 1.2 liter culture was re-suspended in 6×400 ml of 2×YT Amp$_{100}$Kan$_{50}$ (2×YT media containing 100 μg/ml ampicillin and 50 sg/ml kanamycin) and grown at 25° C., 220 rpm for 18 hr in Erlenmeyer flask. Following day, the cell-free phage supernatant was collected by centrifugation at 12,000 rpm for 15 min at 4° C. and the phages were purified using double PEG-NaCl precipitation to obtain purified phage library (P01) (Total ~$2\times10^{14}$ phages at $2\times10^{13}$/ml in 1×PBS; total 10 ml for each batch derived from 5 mini libraries, where 2.4 liter phage supernatant was reduced to 10 ml). The purified phages were stored as aliquots of $4\times10^{12}$ phages (200 µl volume) at −80° C.

Results Obtained

The phages from 36 mini-libraries were rescued in 8 batches (each batch representing ~$1.25\times10^9$ clones) using helper phage AGM13. The 8 phage sub-libraries representing the entire naïve human antibody library were purified using double PEG-NaCl precipitation-based method and named as:
  (a). HuscFvKLibPO1 001-004—These comprise primary phages (P01) rescued from HuscFvKLibC01 001-016 mini-libraries encoding the human variable kappa light chain and variable heavy chain genes in $V_K$-Linker-$V_H$ format.
  (b). HuscFvLLibP01 001-004—These comprise primary phages (P01) rescued from HuscFvLLibC01 001-016 mini-libraries encoding the human variable lambda light chain and variable heavy chain genes in $V_L$-Linker-$V_H$ format.

Example 5

Western Blot Analysis of Phage Sub-Libraries to Determine scFv Display Density

Method Used

The display of scFv-gIIIp fusion protein was evaluated using western blot with anti-gIIIp MAb 30421 IgG. Sample containing $1.5\times10^{11}$ P01 phages and its two-fold dilutions were prepared in 1×Laemmli buffer under reducing conditions and resolved on 0.1% SDS-10% PAG for each of the 8 phage sub-libraries. Post electrophoresis, the proteins were transferred to 0.45 PVDF membrane (IPVH00010, Millipore, Merck) at 65 mA for 16 hr. After transfer, the blots were washed with 1×PBST (1×PBS with 0.05% Tween 20) and blocked with 2% SM-PBST for 1 hr at RT and washed thrice with PBST. The blots were incubated with 1 µg/ml purified mouse anti-gIIIp MAb (30421 IgG) for 1 hr at RT and washed thrice with 1×PBST. Finally, the blots were incubated with HRP conjugated Goat anti-mouse IgG (H+L) (diluted 1:5000 fold in 1% SM-PBST; Jackson ImmunoResearch, PA, USA) for 1 hr at RT followed by 3 washes with 1×PBST and 3 washes with 1×PBS, and developed using 1 mg/ml DAB solution (3,3'-diaminobenzidine; Cat no. D-5837, Sigma, St. Louis, Mo.) containing 0.03% $NiCl_2$ and 0.03% $H_2O_2$ in 1×PBS.

Result Obtained

One of the key features that determine the suitability of an antibody library for isolation of specific binders against any target antigens is the display density of the scFv-gIIIp fusion protein. This was analyzed using western blot of the eight phage sub-libraries representing the naïve human antibody library using mouse anti-gIIIp MAb 30421 IgG. Significant amount of scFv-gIIIp fusion protein (1-3% of total gIIIp) was observed in all the eight phage sub-libraries indicating towards the presence of a large number of in-frame scFv expressing clones in the libraries (FIG. 13, A-D). Furthermore, the production of phages at lower temperature (25° C.) could also have contributed in the improved display of scFv-gIIIp fusion protein by promoting its solubility.

Example 6

Functional Validation of the Phage-Displayed Naïve Human Antibody Library

Method Used

In-Solution Affinity Selection of Phage-Displayed Naïve Human Antibody Library Against 6 Mycobacterial Proteins The phage-displayed naïve human antibody library comprising of 10 billion clones was validated by in-solution affinity selection-based isolation of specific antibody binders against 6 biotin-tagged proteins. The antibodies were selected against three sets of proteins in three different experiments, namely, MTC28-Bio (SEQ ID NO: 68) (100 nM), an equimolar mixture of Ag85A-Bio (SEQ ID NO: 74) and Ag85B-Bio (SEQ ID NO: 76) (50 nM each), and an equimolar mixture of MPT63 (SEQ ID NO: 70), MPT64-Bio (SEQ ID NO: 72) and MPT51-Bio (SEQ ID NO: 78) proteins (33 nM each). The proteins used for this purpose was tagged with Biotin Acceptor Peptide (BAP) and the sequences have been mentioned in the document along with the BAP tag. The sequence of the BAP tag has been represented by SEQ ID NO: 98. The DNA sequences of the proteins MTC28-Bio, MPT63-Bio, MPT64-Bio, Ag85A-Bio, Ag85B-Bio, and MPT51-Bio are represented by SEQ ID NO: 69, SEQ ID NO: 71, SEQ ID NO: 73, SEQ ID NO: 75, SEQ ID NO: 77, and SEQ ID NO: 79 respectively. For affinity selection against MTC28-Bio, $4\times10^{12}$ phages from each of the eight phage sub-libraries were pooled, and the total of $3.2\times10^{13}$ phages (~3200-fold excess of the library) in a volume of 1.6 ml was mixed with 1.6 ml 4% BSA-PBS. The phage library (3.2 ml) was divided into three tubes (2 ml, click cap, clear, round bottom microtubes, Treff Lab, Switzerland), and preadsorbed on pre-washed MyOne streptavidin T1 beads (100 µl per tube) for 1 hr at RT on vertical rotator at 5 rpm for end-to-end mixing. After separation of streptavidin beads using magnetic particle concentrator, the pre-adsorbed library was collected in fresh tubes, and MTC28-Bio protein was added (at a final concentration of 100 nM per tube), followed by incubation for 2 hr at RT with rotation at 5 rpm. To each tube, 100 µl of pre-washed M280 streptavidin beads were added, followed by incubation for 30 min at RT with rotation at 5 rpm to capture biotinylated antigens along with bound phages. The beads were washed 10 times with PBST (1×PBS with 0.05% Tween 20), and 10 times with 1×PBS. Finally, the beads were incubated with 100 mM triethylamine (500 µl per tube) for 10 min at RT with rotation at 5 rpm, and phage eluate from 3 tubes was pooled. The eluate (total 1.5 ml) was neutralized with 750 dl 1 M Tris-HCl, pH 7.5 and an aliquot was used to determine the phage titer by infecting *E. coli* TOP10F' cells. The remaining pool was used for infecting 20 ml *E. coli* TOP10F' cells at 37° C. for 30 min. After infection, the cells were harvested by centrifugation at 5000 rpm for 5 min at RT and re-suspended in 4 ml LB media. The cells were plated on 4×150 mm $LBAmp_{100}Glu_{1\%}$ plates (LB media containing 100 µg/ml ampicillin and 1% glucose) to select for phage transductants (Pan I transductants). Following day, the cells from 150 mm $LBAmp_{100}Glu_{1\%}$ plates were scraped in fresh $2\times YTGlu_{1\%}$ media, mixed with equal volume of 2×glycerol storage solution (65% glycerol, 0.1 M Tris-HCl, pH 8.0, 25 mM $MgSO_4$), and stored at −80° C. An aliquot of cells (~$5\times10^{10}$ cells) was used for rescue of phages using AGM13 helper phage in 1200 ml volume as described in Example 5. The phages were harvested and purified using double PEG-NaCl precipitation, and employed for the next round of panning. In total, three rounds of panning were performed using the same protocol as described for the first round with appropriate changes.

For affinity selection against the second set of proteins comprising a mixture of Ag85A-Bio and Ag85B-Bio (50 nM each) and the third set of proteins comprising a mixture of MPT63-Bio, MPT64-Bio and MPT51-Bio (33 nM each), same protocol was followed as described above. For the third set of proteins, the protein concentration was reduced by 3.3-fold in third round of affinity selection.

Phage ELISA with Purified Pan I and Pan II Phage Preparations Obtained after Affinity Selection Pan I and Pan II phages refer to the phages rescued from the transductants obtained after I and II round of panning, respectively. To determine the enrichment of specific phages, the purified Pan I and Pan II phages obtained during selection against each of the three sets of proteins were tested on 6 biotin-tagged proteins and anti-gIIIp MAb (30421 IgG) using phage ELISA. For phage ELISA, 384 well Nunc Maxisorp plate (Thermo Fisher Scientific, Waltham, US) was coated with 2 μg/ml of each of the 6 biotin-tagged proteins and anti-gIIIp MAb 30421 IgG in 1×PBS at 4° C. for 16 hr. One lane was coated with only 1×PBS as No Coat control. The wells were washed thrice with PBST and blocked with 2% SM-PBST (2% skimmed milk in PBST) for 1 hr at RT. After blocking, the wells were probed with 11-point 3-fold dilutions of the purified Pan I and Pan II phages (~1:10 to 1:1 million-fold) prepared in 1% SM-PBST for 1 hr at RT. The plates were washed thrice with PBST and the bound phages were probed with HRP-conjugated anti-gVIIIp MAb 2911 IgG in 1% SM-PBST for 1 hr at RT. Finally, the plates were washed thrice each with PBST and 1×PBS and the reaction was revealed by adding 25 μl TMB as substrate. Following the incubation for 15 min at RT, the reaction was terminated with 25 μl 1 N $H_2SO_4$ and the absorbance was measured at 450 nm using ELISA plate reader (SpectraMax M5; Molecular Devices, Sunnyvale, Calif., USA).

Sequence Analysis of Transductants Obtained after Affinity Selection

The transductants obtained after second or third round of affinity selection were screened using colony PCR with 5' primer M13R (SEQ ID NO: 99) (5'-AGCGGATAACAAT-TTCACACAGGA-3') and 3' primer U251CO (SEQ ID NO: 100) (5'-GGTTTTATCATCTTTCCACACGT-3'). The PCR products were analyzed on 1.2% analytical agarose gel and sequenced using 2 primers, namely, M13R and U251CO using BigDye terminator chemistry on ABI 3730 XL sequencing platform (Applied Biosystems, Thermo Fisher Scientific, Waltham, USA). The sequences were analyzed using MacVector 12.5.1.

Rescue of Phages from Individual Clones Obtained after Affinity Selection and Analysis of Binding Specificity Using Phage ELISA Selected individual clones obtained after affinity selection were grown in 3 ml MDAGAmp$_{100}$ media at 37° C. for 16 hr at 250 rpm. The cultures were diluted 100-fold in 1.5 ml 2×YT Amp$_{100}$Glu$_{1\%}$ media in 10 ml round bottom 24 well culture plate (Whatman, USA) and grown till OD$_{600nm}$~0.4-0.5 at 37° C., 250 rpm. The cultures were infected with AGM13 helper phage at MOT 20 for 30 min at 37° C. without shaking and 30 min at 37° C. with slow shaking at 100 rpm. The infected cells were harvested at 3000 rpm, 10 min, RT and the cell pellet was re-suspended in 2.5 ml 2×YT Amp$_{100}$Kan$_{50}$ media by gentle shaking. The cultures were grown at 25° C., 220 rpm for 18 hr. The cell-free phage supernatant was collected after centrifugation of culture at 3000 rpm, for 15 min at 4° C. and tested using phage ELISA on respective biotin-tagged proteins to determine the binding specificity of the phages.

For phage ELISA of binders obtained against MTC28 or a mixture of MPT63, MPT64 and MPT51, 384 well Nunc Maxisorp plate (Thermo Fisher Scientific, Waltham, US) was coated with 2 μg/ml of respective biotin-tagged proteins in 1×PBS at 4° C. for 16 hr. The wells were washed thrice with PBST and blocked with 2% SM-PBST for 1 hr at RT. After blocking, the wells were probed with 4-point 5-fold dilutions of the crude phage supernatant (~1:10 to 1:1250 fold) prepared in 1% SM-PBST for 1 hr at RT. Remaining ELISA was performed same as described previously in this Example. For phage ELISA of binders obtained against a mixture of Ag85A and Ag85B, 384 well streptavidin-coated Nunc Immobilizer plate (Thermo Fisher Scientific, Waltham, US) was coated with 2 μg/ml of respective biotin-tagged proteins in 1×PBS at RT for 2 hr. The wells were washed thrice with PBST and blocked with 2% BSA-PBST for 1 hr at RT. After blocking, the wells were probed with 7-point 5-fold dilutions of the crude phage supernatant (~1:10 to 1:156250 fold) prepared in 0.1% BSA-PBST for 1 hr at RT. The plates were washed thrice with PBST and the bound phages were probed with HRP-conjugated anti-gVIIIp MAb 2911 IgG in 0.1% BSA-PBST for 1 hr at RT. Remaining ELISA was performed same as described previously in this Example.

Results Obtained

The affinity selection was performed with an aim to validate the human antibody library for its potential to yield specific binders against multiple targets. After achieving a good quality large library of naïve antibody sequences in the form of phage displayed scFvs, it was imperative to validate its utility in selecting specific binders. For this, 6 recombinant antigens of Mycobacteria with biotin attached to their C-terminus through BAP tag were employed. The use of 6 antigens was split into 3 different experiments where 1 antigen or 2 antigens or 3 antigens were simultaneously used as a bait to select for specific binders. The first, second and third set comprised of one (MTC28-Bio), two (Mixture of Ag85A-Bio and Ag85B-Bio), and three (mixture of MPT63-Bio, MPT64-Bio, and MPT51-Bio) proteins, respectively (Table 7).

TABLE 7

Table 7: Summary of three rounds of in-solution affinity selection of naïve Human antibody library on three sets of target proteins.

| Antigen coated | Set 1 MTC28 | | | Set 2 Ag85A and Ag85B | | | Set 3 MPT63 + MPT64 + MPT51 | | |
|---|---|---|---|---|---|---|---|---|---|
| Round | I | II | III | I | II | III | I | II | III |
| Antigen conc. | 100 nM | 100 nM | 100 Nm | 50 nM (each P) | 50 nM (each P) | 50 nM (each P) | 33 nM (each P) | 33 nM (each P) | 10 nM (each P) |
| Total Binding Reaction Volume | 3 ml | 3 ml | 3 ml | 3 ml | 3 ml | 3 ml | 3 ml | 3 ml | 1 ml |
| No. of washes (PBST + PBS) | 10 + 10 | 10 + 10 | 15 + 15 | 10 + 10 | 15 + 15 | 15 + 15 | 10 + 10 | 15 + 15 | 15 + 15 |

TABLE 7-continued

Table 7: Summary of three rounds of in-solution affinity selection of naïve Human antibody library on three sets of target proteins.

| Antigen coated | Set 1 MTC28 | | | Set 2 Ag85A and Ag85B | | | Set 3 MPT63 + MPT64 + MPT51 | | |
|---|---|---|---|---|---|---|---|---|---|
| Round | I | II | III | I | II | III | I | II | III |
| Total input phage | $1.5 \times 10^{13}$ | $3 \times 10^{12}$ | $6 \times 10^{11}$ | $6 \times 10^{12}$ | $6 \times 10^{12}$ | $6 \times 10^{11}$ | $6 \times 10^{12}$ | $3 \times 10^{12}$ | $2 \times 10^{12}$ |
| Total output phage | $5.4 \times 10^{7}$ | $6.3 \times 10^{7}$ | $4.5 \times 10^{8}$ | $4.3 \times 10^{6}$ | $4.5 \times 10^{8}$ | $4.5 \times 10^{8}$ | $4 \times 10^{6}$ | $9 \times 10^{8}$ | $1.5 \times 10^{8}$ |
| No. of clones analyzed in ELISA | — | 20 | 24 | — | — | 16 | — | — | 16 |
| Positive clones based on ELISA | NA | 15 (75%) | 24 (100%) | NA | NA | 15 (93.7%) | NA | NA | 14 (87.5%) |
| Clones reactive specifically against each antigen out of positive clones | — | MTC28 - 15 | MTC28 - 24 | — | — | Ag85A - 3 Ag85B - 4 Ag85A + Ag85B - 8 | — | — | MPT63-4 MPT64-1 MPT51-9 |
| Frequency of different clones[b] | NA | 1 (2), 12 (1) | 2 (2), 16 (1) | NA | NA | 16 (1) | NA | NA | 1 (5), 2 (2), 1 (3), 10 (1) |

[a]Streptavidin M-280 Dynabeads were used for specific capture of biotin-tagged proteins for affinity selection;
[b]The data represents the number of times different clones were isolated during screening as "Number of clones (Frequency of clones)";
ND, Not Determined; P, Protein; NA, Not applicable.

A pool of eight phage sub-libraries representing the entire diversity of the available naïve human antibody library was prepared and employed for the isolation of specific antibody binders. Three iterative rounds of in-solution affinity selection were performed on each set of target proteins. For the first set comprising of a single protein MTC28-Bio, the selections were performed at 100 nM protein concentration (~3 μg/ml). Phage ELISA-based analysis of the Pan I and Pan II phages, which refer to the phages rescued from the transductants obtained after I and II round of panning, respectively, revealed approximately 27 (Pan I) and 729 (Pan II) fold increase in the specific signal with MTC28 protein over the non-specific proteins, indicating that two rounds of affinity selection are sufficient for the enrichment of specific binders against the target proteins (FIGS. 14, A and B). Nevertheless, third round of affinity selection was performed and individual transductants obtained after second and third round of affinity selection were rescued with AGM13 helper phage and analyzed using phage ELISA. Approximately 75% (15/20) and 100% clones were found to be reactive to the target MTC28-Bio protein, with no cross-reactivity on non-specific MPT64-Bio protein (Table 7). The ELISA reactivity of eight representative clones against specific (MTC28-Bio) and non-specific (MPT64-Bio) proteins is shown in FIG. 15. It can be clearly seen that different clones exhibit variable reactivity towards the specific protein. Sequence analysis of the 14 MTC28-Bio reactive clones obtained after second round of selection revealed that only 1 clone was represented twice, and rest 12 clones were unique. Similarly, the sequence analysis of 20 clones obtained after third round of selection revealed that only 2 clones were represented twice and rest 16 clones were unique (Table 7). The clone represented twice after the second round was represented only once in screening after third round of selection and no other sequences were found to be common between the two rounds. These results clearly indicate towards the quality of the library in terms of its diversity, which led to the selection of a large number of unique reactive clones. The analysis of CDR sequences of eight representative clones using IMGT revealed that CDRs were highly diverse and the reactive clones carried combinations of variable light and heavy chain genes belonging to different gene families, which can possibly recognize different epitopes on the protein (FIG. 16A). Availability of a large diversity of specific clones also provides an opportunity to select lead clones with variable gene family combinations and CDR3 lengths that have been reported to have higher solubility or other desirable characteristics (Ewert, S., T. Huber, A. Honegger and A. Pluckthun (2003). "Biophysical properties of human antibody variable domains." J Mol Biol 325(3): 531-53).

The second set comprised a mixture of two biotin-tagged mycobacterial proteins, namely Ag85A-Bio and Ag85B-Bio. It should be noted that Ag85A and Ag85B proteins have highly similar sequences at amino-acid level (>80%). The selections were performed on an equimolar mixture containing each protein at 50 nM concentration. Phage ELISA-based analysis of the amplified phage pools obtained after first and second round of affinity selection (Pan I and Pan II), revealed approximately 27 and 100-fold increase, respectively, in the specific signal with Ag85A-Bio protein over the non-specific proteins (FIG. 14, C-D). However, the increase in specific signal was approximately 3-fold less for Ag85B-Bio as compared to Ag85A-Bio protein (FIG. 14, C-D). Sequence analysis of the 16 clones obtained after third round of affinity selection revealed that all clones were unique. Phage ELISA-based analysis of these 16 clones carrying different sequences revealed that approximately 15/16 (93.7%) clones were reactive to the target proteins Ag85A-Bio and Ag85B-Bio, with negligible cross-reactivity on non-specific MPT51-Bio protein (Table 7 and FIG. 17). Interestingly, 3 clones were reactive to Ag85A-Bio, 4 clones were reactive to Ag85B-Bio and 8 clones were reactive to both Ag85A and Ag85B-Bio proteins. This clearly underscores the fact that the library is highly diverse and can yield specific as well common binders against two highly similar proteins, which differ in sequence by few amino acids. The ELISA reactivity of a few representative clones specific to Ag85A-Bio (Panel 1-3), Ag85B-Bio (Panel 4-5), and both Ag85A-Bio and Ag85B-Bio proteins (Panel 6-9) is shown in FIG. 17. It can be clearly noted that different clones exhibit variable reactivity profile against respective antigens. The analysis of the CDR sequences of the representative clones specific to Ag85A-Bio, Ag85B-Bio, and both Ag85A-Bio and Ag85B-Bio proteins using IMGT revealed that CDRs were highly diverse and the reactive clones carried different combinations of variable light and heavy chain genes belonging to different gene families, further indicating towards the ability of library to yield diverse range of binders (FIG. 16, B-D).

The third set comprised a mixture of three mycobacterial proteins, namely MPT63-Bio, MPT64-Bio, and MPT51-Bio. The first and second rounds of selections were performed on an equimolar mixture containing each protein at 33 nM concentration, whereas the concentration was reduced by 3.3-fold in third round of selection. Phage ELISA-based analysis of the amplified phage pools obtained after first and second round of affinity selection (Pan I and Pan II), revealed significant increase in the specific signal with all three proteins over the non-specific proteins, however, MPT63-Bio and MPT51 showed more increase as compared to MPT64-Bio (FIG. 14, E-F). Sequence analysis of the 22 clones obtained after third round of affinity selection revealed that 1 set of 5 clones contained similar CDRs, but the framework sequences of 1 clone were different from the other 4 clones by 5 amino acids in frame work regions, 2 clones were represented twice, 1 set of 3 clones contained similar CDRs, but the framework sequences of 1 clone were different from the other 2 clones by 6 amino acids, and rest 10 clones were unique. Phage ELISA-based analysis of the unique 16 clones revealed that approximately 87.5% (14/16) clones were reactive to one of target proteins MPT63-Bio, MPT64-Bio, or MPT51-Bio, with negligible cross-reactivity on within this group or the non-specific MTC28-Bio protein (Table 7 and FIG. 18). This again proves that the library is highly diverse and can yield specific binders to each protein present in a mixture of three proteins. The ELISA reactivity of the representative clones specific to MPT63-Bio (Panel 1-4), MPT64-Bio (Panel 5), and MPT51-Bio proteins (Panel 6-12) is shown in FIG. 18. It can be clearly seen that different clones exhibit variable reactivity profile against respective antigens. The analysis of the CDR sequences of the representative clones specific to MPT63-Bio, MPT64-Bio, and MPT51-Bio proteins using IMGT further revealed that CDRs were highly diverse and the reactive clones carried different combinations of variable light and heavy chain genes belonging to different gene families, again indicating towards the ability of library to yield diverse range of binders (FIG. 16, E-G).

In addition to the functional validation of the naïve human antibody fragment library as disclosed in the present document, the present library was screened for binders against fragments derived from *Mycobacterium tuberculosis* MTBLIB42C02 gene fragment library. A pool of binders was obtained after third round of panning against 9 protein fragments (target molecules) of MTBLIB42C02 gene fragment library. The amino acid and nucleotide sequences of the 9 target molecules have been disclosed in the present description. The BAP tagged amino acid sequences of recombinant peptides for fragments MTBLIB42C02-F1, MTBLIB42C02-F2, MTBLIB42C02-F4, MTBLIB42C02-F6, MTBLIB42C02-F7, MTBLIB42C02-F8, MTBLIB42C02-F10, MTBLIB42C02-F11, MTBLIB42C02-F12 are represented by SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96, respectively. The nucleotide sequences for the 9 fragments MTBLIB42C02-F1, MTBLIB42C02-F2, MTBLIB42C02-F4, MTBLIB42C02-F6, MTBLIB42C02-F7, MTBLIB42C02-F8, MTBLIB42C02-F10, MTBLIB42C02-F11, MTBLIB42C02-F12 are represented by SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, and SEQ ID NO: 97 respectively.

Overall, the present data in the present disclosure asserts that the naïve human antibody library as disclosed herein is a well-balanced and highly diverse library that holds potential to yield large numbers of highly specific binders against diverse range of target proteins, even when present in a mixture. More importantly, it can yield specific as well as common binders reactive to proteins that carry highly similar sequences. This library is expected to serve as a rich source of specific antibodies against a diverse set targets including proteins encoded by mycobacterial genome. Although the data is only shown for 6 mycobacterial proteins, considering the quality of the antibody fragment library of the present disclosure, it can be contemplated that the library will be useful in isolating binders against a variety of targets like rabies virus proteins, Chikungunya virus proteins, dengue virus proteins, influenza virus proteins, HIV proteins, snake venom proteins, thyroid hormones, CD20, EGFR (epidermal growth factor receptor), VEGFA (vascular endothelial growth factor A), TNFα (Tumor necrosis factor), CD (Cluster of differentiation)52 CD25, CD3, IgE (Immunoglobulin E), IIb/IIIa integrin receptor, EPO-R (Erythropoietin), G-CSF (granulocyte colony stimulating factor) receptor, GM-CSF receptor, testosterone, β-estradiol, IL-2, BSA (bovine serum albumin), lymphotoxin-β (LT-β), E-selectin ligand-1 (ESL-1), prostate specific antigen, chymotrypsin, human chorio gonadotropin (hCG), enzymes, cell-lines, lysozyme, Tetanus toxoid, attenuated rabies virus, Chikungunya virus, dengue virus, influenza virus, HIV, haptens, cytokines, non-protein Ags, chimeric proteins, and interleukins and more. Further, the process disclosed in the document can also be used to construct an immunized human library, additionally a naïve or an immunized antibody gene library can also be constructed from any subject selected from the group consisting of mouse, rabbits, chicken, llama, camel, horse, sheep, and porcine and more. Also, the cloning strategy can be used beyond antibodies to construct libraries because this teaches us restriction enzyme-free seamless cloning strategy, avoidance of chimerization during splicing of multiple genes using emulsion PCR, high-quality vector and insert preparation using blue-light.

Advantages of the Present Disclosure

The highly optimized antibody library construction technique as disclosed in the present document involves use of high efficiency restriction enzyme-free cloning strategy. Unlike other antibody gene cloning strategies described in the literature, which employ restriction enzymes that cut rarely in the antibody genes, the cloning strategy described herein does not require any restriction enzyme digestion of the insert, thereby ensuring cloning of the entire spectrum of the antibody repertoire, which may get eliminated upon digestion. The cloning strategy has been designed in a manner to make it entirely seamless with no extra amino acid residues at the N or C-terminus of variable light or heavy chain genes that may affect binding of the antibody fragments. Furthermore, for the assembly of variable genes, use of emulsion-based SOE-PCR (SOE-ePCR) has been optimized to alleviate most of the commonly observed but largely overlooked PCR artifacts. SOE-ePCR allows PCR based splicing and amplification in small water-in-oil emulsion compartments thereby preventing homogeneous mixing of all the template molecules and generation of spurious PCR products due to chimerization events between highly similar antibody gene sequences. Using SOE-ePCR, highly pure and accurate spliced scFv fragments were obtained that enhanced the quality of the library to huge extent. Patent Application WO 2013/188872 provides a method for high-throughput sequencing of two or more genes expressed in a single cell. The process uses emulsion PCR for linking of two transcripts arising from a single cell so that their pairing is not lost, and the transcripts can be sequenced in a high-throughput format using next-generation sequencing (NGS) techniques. However, this process does not involve cloning of antibody genes and the $V_L$ and $V_H$ genes are linked in opposite orientations. The present disclosure discloses emulsion-based PCR for cloning of antibody genes.

A key feature of libraries is the percentage of clones encoding full-length antibody genes. Based on the libraries described in the literature, the number of clones carrying full-length insert varies between 66-96%. The short clones (carrying only one antibody chain or incomplete PCR product) have been reported to persist even after the phage rescue (WO 2018/002952 A2) necessitating the use of elaborate steps for their removal during the selection of binders. (de Bruin et al., 1999, "Selection of high-affinity phage antibodies from phage display libraries." Nat Biotechnol 17(4): 397-9) have shown that while the number of short clones was less than 1% in the original unselected library, the number of such short insert clones increased to about 60% after two rounds of panning making the selection of binders very difficult. In this regard, the library described in the present disclosure has 100% recombinants and most importantly has no short clones (~100% clones have full-length scFv genes) and such short clones have never been isolated even after three rounds of panning. This has been possible due to the use of emulsion PCR, which gives clean amplifications during splicing without any non-specific bands and the highly efficient restriction enzyme-free cloning strategy. Another important feature of the libraries is the ability to yield specific binders against any target. The review of literature reveals that although most of the libraries yield binders against different target antigens, the percentage of positive clones obtained after 2-5 rounds of panning can be generally in the range of 9-95% with as low as 1%. However, if it is 95% or 1%, it is for 1-2 targets out of average 10 targets. As reported by (Schwimmer et al., 2013), even with a very large library of >$10^{11}$ clones, after three rounds of selection, 16-88% (scFv library) and 10-48% (Fab library) of the clones were found to be positive against different targets. (Schofield et al., 2007, "Application of phage display to high throughput antibody generation and characterization." Genome Biol 8(11): R254) evaluated their library against 404 targets and obtained specific antibodies against 292 targets (72%). In this, the primary analysis of 38,164 antibodies revealed that only 9,384 antibodies (24.6%) were positive in the primary screen after two rounds of selection. In this regard, the library described in the present disclosure yield a large number of positive clones after third round of selection (87.5-100%; Table 7). This underscores the robustness of the panning protocol along with the quality of the library in terms of diversity and thus the potential to yield antibodies against diverse range of targets.

Finally, the use of 'Blue-Light' instead of UV light during all the DNA manipulations involving agarose gels to prevent any damage to the DNA, which could reduce ligation efficiencies. Put together, with this novel combination of different technologies, very high efficiencies have been achieved in terms of high transformation efficiencies in the range of $1\times10^9$/µg DNA in a standard laboratory set-up and have further exemplified the use of these strategies for the construction of a much superior and reasonably large human naïve scFv library comprising of approximately 10 billion clones.

The present study clearly underscores the large diversity of the library and its potential to yield specific as well common binders against two highly similar proteins, which differ in sequence by just few amino acids. The presence of a large variety of binders present in the library is an important aspect which has been highlighted in the present study. The availability of such a large set of specific binders reactive against any target molecule is very essential and provides an opportunity to choose binders with desired characteristics depending on the downstream application. For example, binders that are relatively more soluble can be chosen for production of antibodies in large amounts. Since the library is naïve and the affinity of the specific antibodies may not be very high, access to a large number of specific yet different clones can also improve the success rate of the downstream protocols like affinity maturation.

We claim:

1. A method for generating a naïve human antibody fragment library, said method comprising:
   a) Obtaining an RNA sample from PBMCs of a human subject;
   b) obtaining a first strand of cDNA from the RNA sample;
   c) amplifying the first strand of cDNA using primers K1 as set forth in SEQ ID NO: 1—K7 as set forth in SEQ ID NO: 7 with C1 as set forth in SEQ ID NO: 15 to yield amplicons comprising Signal sequence*-$V_\kappa$-$C_\kappa$ fragments, and purifying the amplicons using non-ethidium bromide based stained gel for visualizing the amplicons using a blue light;
   d) amplifying the first strand of cDNA using primers L1 as set forth in SEQ ID NO: 16—L11 as set forth in SEQ ID NO: 26 with C2 as set forth in SEQ ID NO: 38 to yield amplicons comprising Signal sequence*-$V_L$-$C_L$ fragments, and purifying the amplicons using non-ethidium bromide based stained gel for visualizing the amplicons using the blue light;
   e) amplifying the first strand of cDNA using primers H1 as set forth in SEQ ID NO: 46—H9 as set forth in SEQ ID NO: 54 with HuJM32 as set forth in SEQ ID NO: 64 to yield amplicons comprising L*-$V_H$-M-$C_{H1}$ fragments, and purifying the amplicons using non-ethidium bromide based stained gel for visualizing the amplicons using the blue light;
   f) amplifying the amplicons of step (c) using primers K8 as set forth in SEQ ID NO: 8-K13 as set forth in SEQ ID NO: 13 with KS1 as set forth in SEQ ID NO: 39-KS4 as set forth in SEQ ID NO: 42 to yield 24 amplicons comprising Signal sequence#-$V_\kappa$-Linker (L) fragments, pooling of the 24 amplicons obtained from 28 reactions and purifying the pool of amplicons using non-ethidium bromide based stained gel for visualizing the amplicons using the blue light;
   g) amplifying the amplicons of step (d) using primers L12 as set forth in SEQ ID NO: 27-L22 as set forth in SEQ ID NO: 37 with LS1 as set forth in SEQ ID NO: 43-LS3 as set forth in SEQ ID NO: 45 to yield 33 amplicons comprising Signal sequence#-$V_L$-Linker (L) fragments, pooling of all the 33 amplicons, and purifying the pool of amplicons using non-ethidium bromide based stained gel for visualizing the amplicons using the blue light;
   h) amplifying the amplicons of step (e) using primers H10 as set forth in SEQ ID NO: 55—H18 as set forth in SEQ ID NO: 63 with HuJG-33 as set forth in SEQ ID NO: 65 to yield 9 amplicons comprising L-L-L-$V_H$-$G_{CH1}$ fragments, pooling of all the 9 amplicons, and purifying the pool of amplicons using non-ethidium bromide based stained gel for visualizing the amplicons using the blue light;
   i) pooling equimolar concentrations of the amplicons of steps (f) and (h), and performing emulsion-based splicing by Overlap Extension PCR (SOE-ePCR) using primers PelBclo-51 as set forth in SEQ ID NO: 66 and HuJGclo-34 as set forth in SEQ ID NO: 67 to obtain spliced scFv comprising #Signal sequence-$V_\kappa$-L-L-$V_H$-G-$C_{H1}$* fragments, and purifying amplicons using non-ethidium bromide based stained gel for visualizing the amplicons using the blue light;

j) pooling equimolar concentrations of the amplicons of steps (g) and (h), and performing emulsion-based splicing by Overlap Extension PCR, denoted as SOE-ePCR using primers PelBclo-51 as set forth in SEQ ID NO: 66 and HuJGclo-34 as set forth in SEQ ID NO: 67 to obtain spliced scFv comprising Signal sequence-$V_L$-L-L-$V_H$-$G_{CH1}$ fragments, and purifying amplicons using non-ethidium bromide based stained gel for visualizing the amplicons using the blue light;

k) restriction enzyme-free treatment of spliced scFv of step (i) and (j) with T4 DNA polymerase in the presence of dTTP to generate 4 base 5' overhangs for insertion in phage display vector;

l) digesting pVCHuscFvSacBclo36006 phagemid vector with BsaI restriction enzyme to produce linearized vector with 4 base 5' overhangs;

m) ligating the scFv products of step (k) individually to BsaI linearized phagemid vector of step (l) to obtain recombinant vector and transforming the recombinant vector in a E. coli cell to obtain the naïve human antibody fragment library, wherein the naïve human antibody fragment library comprises two libraries, and wherein the two libraries consists of a first library comprising scFv of $V_\kappa$-L-L-L-$V_H$ products and a second library comprising scFv of $V_L$-L-L-L-$V_H$ products;

n) storage of antibody libraries as mini-libraries comprising scFv in $V_\kappa$-L-L-L-$V_H$ format and mini-libraries comprising scFv in $V_L$-L-L-L-$V_H$ format, wherein the signal sequence is PelB; and wherein the method leads to generation of the naïve human antibody fragment library and the library comprises at least 8 billion clones.

2. The method as claimed in claim 1, wherein the blue light indicates light of wavelength in the range of 470 nm to 490 nm.

3. The method as claimed in claim 1, wherein the linker is an amino acid chain ranging from 15-18 amino acids.

4. A method for isolating specific binders from a naïve human antibody fragment library, said method comprising:

a) obtaining the naïve human antibody fragment library by a method as claimed in claim 1;

b) performing phage rescue in at least 8 batches, each batch comprising at least 5 mini-libraries from the antibody library using a helper phage to yield phage libraries, wherein the phage libraries represent an entire naïve human antibody fragment library and the phage libraries comprise mini-libraries;

c) pre-adsorption of the antibody displaying phage libraries on streptavidin-coated beads to obtain pre-adsorbed phage libraries;

d) linking the target molecule to biotin to obtain biotinylated target molecules; and e) contacting the pre-adsorbed phage libraries of step (c) to the biotinylated target molecules of step (d), allowing binding between antibody displaying phages and the biotinylated target, followed by capture of the biotinylated target using streptavidin-coated beads, washing of non-specific phages and elution of specific binders, wherein the method isolates specific binders from the naïve human antibody fragment library.

5. The method as claimed in claim 4, wherein the target molecule is selected from a group consisting of *Mycobacterium* sp. proteins, rabies virus proteins, Chikungunya virus proteins, dengue virus proteins, influenza virus proteins, Ebola virus proteins, Zika virus proteins, Nipah virus proteins, Hendra Virus proteins, West Nile virus proteins, Japanese Encephalitis Virus proteins, Chandipura Virus proteins, Hepatitis B virus proteins, Hepatitis C virus proteins, Human papilloma virus proteins, HIV proteins, snake venom proteins, thyroid hormones, CD20, EGFR (epidermal growth factor receptor), VEGFA (vascular endothelial growth factor A), TNFα (Tumor necrosis factor), CD (Cluster of differentiation)52 CD25, CD3, IgE (Immunoglobulin E), IIb/IIIa integrin receptor, EPO-R (Erythropoietin), G-CSF (granulocyte colony stimulating factor) receptor, GM-CSF receptor, testosterone, β-estradiol, IL-2, BSA (bovine serum albumin), lymphotoxin-β (LT-β), E-selectin ligand-1 (ESL-1), prostate specific antigen, chymotrypsin, human chorio gonadotropin (hCG), enzymes, cell-lines, lysozyme, tetanus toxoid, attenuated rabies virus, Chikungunya virus, dengue virus, influenza virus, Ebola virus, Zika virus, Nipah virus, Hendra Virus, West Nile virus, Japanese Encephalitis Virus, Chandipura Virus, Hepatitis B virus, Hepatitis C virus, Human papilloma virus, HIV, rabies (Virus Like Particle) VLP, Chikungunya VLP, dengue VLP, influenza VLP, Ebola VLP, Zika VLP, Nipah VLP, Hendra VLP, West Nile VLP, Japanese Encephalitis VLP, Chandipura VLP, Hepatitis B VLP, Hepatitis C VLP, Human papilloma VLP, HIV VLP, HIV, haptens, cytokines, non-protein Ags, chimeric proteins, interleukins, snake venom metalloproteinases (SVMPs), phospholipases, snake venom serine proteases, three finger toxins, dendrotoxins, L-amino acid oxidase, cysteine-rich secretory protein (CRISP), C-type lectin-like protein, low molecular mass myotoxin, disintegrins, Hyaluronidase, bacteria, bacterial products, bacterial toxins, bacterial cell surface proteins, bacterial secretory proteins, and combinations thereof.

6. The method as claimed in claim 5, wherein the target molecule is selected from a group consisting of MTC28, Ag85A, Ag85B, MPT63, MPT64, MPT51, MTBLIB42C02-F1, MTBLIB42C02-F2, MTBLIB42C02-F4, MTBLIB42C02-F6, MTBLIB42C02-F7, MTBLIB42C02-F8, MTBLIB42C02-F10, MTBLIB42C02-F11, MTBLIB42C02-F12, and combinations thereof.

7. The method as claimed in claim 1, wherein the non-ethidium bromide based gel staining is done using a dye selected from the group consisting of SYBR Safe stain SYBR gold, SYBR green, Gel-green, GelStar, SafeView stain, EZ-VISION® Blue Light DNA Dye, and Midori Green.

* * * * *